(12) United States Patent
Singh et al.

(10) Patent No.: US 11,986,341 B1
(45) Date of Patent: May 21, 2024

(54) METHODS FOR ACCESSING SPINAL COLUMN USING B-MODE IMAGING TO DETERMINE A TRAJECTORY WITHOUT PENETRATING THE THE PATIENT'S ANATOMY

(71) Applicant: Tissue Differentiation Intelligence, LLC, Chicago, IL (US)

(72) Inventors: Kern Singh, Chicago, IL (US); Sachin Gupta, Hinsdale, IL (US)

(73) Assignee: Tissue Differentiation Intelligence, LLC, Chicago, IL (US)

( * ) Notice: Subject to any disclaimer, the term of this patent is extended or adjusted under 35 U.S.C. 154(b) by 201 days.

(21) Appl. No.: 15/606,814

(22) Filed: May 26, 2017

Related U.S. Application Data

(60) Provisional application No. 62/341,966, filed on May 26, 2016.

(51) Int. Cl.
*A61B 8/08* (2006.01)
*A61B 8/00* (2006.01)
*A61B 8/12* (2006.01)
*A61B 17/00* (2006.01)

(52) U.S. Cl.
CPC ............... *A61B 8/085* (2013.01); *A61B 8/12* (2013.01); *A61B 8/4494* (2013.01); *A61B 8/5223* (2013.01); *A61B 17/00234* (2013.01)

(58) Field of Classification Search
CPC ......... A61B 8/085; A61B 8/5223; A61B 8/12; A61B 8/4494; A61B 17/00234; A61B 17/1671; A61B 17/1757
USPC ........................................................ 600/439
See application file for complete search history.

(56) References Cited

U.S. PATENT DOCUMENTS

| | | | |
|---|---|---|---|
| 5,224,480 A | 7/1993 | Yamada et al. |
| 5,361,767 A | 11/1994 | Yukov |
| 5,935,074 A | 8/1999 | Mo et al. |
| 6,048,311 A | 4/2000 | Washburn et al. |

(Continued)

FOREIGN PATENT DOCUMENTS

| | | |
|---|---|---|
| CN | 102940510 A | 2/2013 |
| CN | 105030279 A | 11/2015 |

(Continued)

OTHER PUBLICATIONS

KR 10-1586977 B1 (Gil Medical Ct; Univ Gachon Ind Acad Coop Found). Translated by Espacenet. Jan. 21, 2016 [retrieved on Jul. 1, 2021]. (Year: 2016).

(Continued)

*Primary Examiner* — Christopher Koharski
*Assistant Examiner* — Richmond J Van Winter
(74) *Attorney, Agent, or Firm* — Banner & Witcoff, Ltd.

(57) ABSTRACT

Devices, systems, and methods are disclosed for use in contexts such as minimally invasive surgery (MIS). A device having an ultrasound transducer and methods for using the device are disclosed. A patient's anatomy may be scanned by use of the device and various target anatomy located. Trajectory information which corresponds to a path free of the various target anatomy may be presented to an operator of the device. By scanning the tissue, identifying the anatomy, and presenting the results to the operator, unnecessary damage to elements of the patient's anatomy may be avoided or lessened.

16 Claims, 50 Drawing Sheets

(56) References Cited

U.S. PATENT DOCUMENTS

| | | |
|---|---|---|
| 6,120,445 A | 9/2000 | Grunwald |
| 6,126,601 A | 10/2000 | Gilling |
| 6,135,961 A | 10/2000 | Pflugrath et al. |
| 6,181,810 B1 | 1/2001 | Zhang et al. |
| 6,213,958 B1 | 4/2001 | Winder |
| 6,248,072 B1 | 6/2001 | Murkin |
| 6,248,073 B1 | 6/2001 | Gilbert et al. |
| 6,251,073 B1 | 6/2001 | Imran et al. |
| 6,287,259 B1 | 9/2001 | Grunwald |
| 6,325,759 B1 | 12/2001 | Pelissier |
| 6,358,206 B1 | 3/2002 | Cohen-Bacrie |
| 6,379,304 B1 | 4/2002 | Gilbert et al. |
| 6,383,139 B1 | 5/2002 | Hwang et al. |
| 6,413,217 B1 | 7/2002 | Mo |
| 6,416,475 B1 | 7/2002 | Hwang et al. |
| 6,450,959 B1 | 9/2002 | Mo et al. |
| 6,475,149 B1 | 11/2002 | Sumanaweera |
| 6,491,636 B2 | 12/2002 | Chenal et al. |
| 6,514,202 B2 | 2/2003 | Grunwald |
| 6,530,888 B2 | 3/2003 | Smith et al. |
| 6,537,217 B1 | 3/2003 | Bjærum et al. |
| 6,544,181 B1 | 4/2003 | Buck et al. |
| 6,569,101 B2 | 5/2003 | Quistgaard et al. |
| 6,572,547 B2 | 6/2003 | Miller et al. |
| 6,579,239 B1 | 6/2003 | Avinash et al. |
| 6,579,244 B2 | 6/2003 | Goodwin |
| 6,679,843 B2 | 1/2004 | Ma et al. |
| 6,741,895 B1 | 5/2004 | Gafni et al. |
| 6,746,402 B2 | 6/2004 | Ustuner |
| 6,849,047 B2 | 2/2005 | Goodwin |
| 6,875,176 B2 | 4/2005 | Mourad et al. |
| 6,896,658 B2 | 5/2005 | Ji et al. |
| 6,945,938 B2 | 9/2005 | Grunwald |
| 7,074,188 B2 | 7/2006 | Nair et al. |
| 7,141,020 B2 | 11/2006 | Poland et al. |
| 7,175,597 B2 | 2/2007 | Vince et al. |
| 7,215,802 B2 | 5/2007 | Klingensmith et al. |
| 7,347,821 B2 | 3/2008 | Skyba et al. |
| 7,463,759 B2 | 12/2008 | Klingensmith et al. |
| 7,466,256 B2 | 12/2008 | Brueske et al. |
| 7,472,597 B2 | 1/2009 | Zhang et al. |
| 7,481,769 B2 | 1/2009 | Karasawa |
| 7,680,307 B2 | 3/2010 | Sathyanarayana |
| 7,682,309 B2 | 3/2010 | Ji et al. |
| 7,686,766 B2 | 3/2010 | Quistgaard et al. |
| 7,729,533 B2 | 6/2010 | Sathyanarayana |
| 7,804,990 B2 | 9/2010 | Kiraly et al. |
| 7,815,572 B2 | 10/2010 | Loupas |
| 7,823,453 B2 | 11/2010 | Zhang et al. |
| 7,876,934 B2 | 1/2011 | Georgescu et al. |
| 7,920,922 B2 | 4/2011 | Gharib et al. |
| 8,010,181 B2 | 8/2011 | Smith et al. |
| 8,041,413 B2 | 10/2011 | Barbagli et al. |
| 8,105,237 B2 | 1/2012 | Waters et al. |
| 8,105,239 B2 | 1/2012 | Specht |
| 8,219,177 B2 | 7/2012 | Smith et al. |
| 8,219,178 B2 | 7/2012 | Smith et al. |
| 8,265,355 B2 | 9/2012 | Zhao et al. |
| 8,568,317 B1 | 10/2013 | Gharib et al. |
| 8,663,116 B2 | 3/2014 | Hamilton, Jr. |
| 8,679,018 B2 | 3/2014 | McLaughlin et al. |
| 8,715,187 B2 | 5/2014 | Landberg Davis et al. |
| 8,715,292 B2 | 5/2014 | Glazer |
| 8,754,888 B2 | 6/2014 | Virtue et al. |
| 8,870,773 B2 | 10/2014 | Narouze |
| 8,876,721 B2 | 11/2014 | Nakamura |
| 8,983,567 B1 | 3/2015 | Miles et al. |
| 9,058,649 B2 | 6/2015 | Harrison et al. |
| 9,086,474 B2 | 7/2015 | Li et al. |
| 9,125,589 B2 | 9/2015 | Sornes |
| 9,251,593 B2 | 2/2016 | Villain et al. |
| 9,277,902 B2 | 3/2016 | Mullick et al. |
| 9,324,155 B2 | 4/2016 | Mendonca et al. |
| 9,592,027 B2 | 3/2017 | Nair |
| 9,597,054 B2 | 3/2017 | Kudavelly et al. |
| 9,655,592 B2 | 5/2017 | Schroecker et al. |
| 10,154,826 B2* | 12/2018 | Singh ............... A61B 42/10 |
| 2003/0045797 A1 | 3/2003 | Christopher et al. |
| 2003/0125629 A1 | 7/2003 | Ustuner |
| 2004/0097801 A1 | 5/2004 | Mesallum |
| 2004/0152983 A1* | 8/2004 | Vince ............... A61B 5/7264 |
| | | 600/454 |
| 2004/0240715 A1 | 12/2004 | Wicker et al. |
| 2005/0101866 A1 | 5/2005 | Goodwin |
| 2005/0149035 A1 | 7/2005 | Pimenta et al. |
| 2005/0245822 A1 | 11/2005 | Dala-Krishna et al. |
| 2006/0155169 A1 | 7/2006 | Bastia et al. |
| 2006/0235338 A1 | 10/2006 | Pacheco |
| 2006/0253107 A1* | 11/2006 | Hashimshony ....... A61B 34/20 |
| | | 606/1 |
| 2007/0078342 A1 | 4/2007 | Jago |
| 2007/0116338 A1 | 5/2007 | Fidrich et al. |
| 2007/0167802 A1 | 7/2007 | Rigby et al. |
| 2007/0238953 A1 | 10/2007 | Lucassen et al. |
| 2007/0276397 A1 | 11/2007 | Pacheco |
| 2008/0009738 A1 | 1/2008 | Li et al. |
| 2008/0015439 A1 | 1/2008 | Raju et al. |
| 2008/0077010 A1 | 3/2008 | Cohen-Solal et al. |
| 2008/0119727 A1 | 5/2008 | Barbagli et al. |
| 2008/0183076 A1 | 7/2008 | Witte et al. |
| 2008/0188749 A1 | 8/2008 | Rasche et al. |
| 2008/0195102 A1* | 8/2008 | Glazer ............. A61B 17/1757 |
| | | 606/80 |
| 2008/0267499 A1 | 10/2008 | Deischinger et al. |
| 2009/0131791 A1 | 5/2009 | Clark |
| 2009/0171205 A1 | 7/2009 | Kharin et al. |
| 2009/0264757 A1 | 10/2009 | Yang et al. |
| 2010/0010367 A1 | 1/2010 | Foley et al. |
| 2010/0111389 A1 | 5/2010 | Strobel et al. |
| 2010/0204567 A1* | 8/2010 | Narouze ............ A61B 8/0833 |
| | | 600/424 |
| 2010/0286518 A1 | 11/2010 | Lee et al. |
| 2010/0286519 A1 | 11/2010 | Lee et al. |
| 2011/0098531 A1* | 4/2011 | To ................ A61B 17/0218 |
| | | 600/114 |
| 2011/0208226 A1* | 8/2011 | Fatone ............. A61B 17/025 |
| | | 607/117 |
| 2011/0213250 A1 | 9/2011 | Vion et al. |
| 2011/0263985 A1 | 10/2011 | Gauthier et al. |
| 2011/0319765 A1 | 12/2011 | Gertner et al. |
| 2012/0116218 A1 | 5/2012 | Martin et al. |
| 2012/0152021 A1 | 6/2012 | Ma et al. |
| 2012/0184853 A1 | 7/2012 | Waters |
| 2012/0197124 A1 | 8/2012 | Nakamura |
| 2012/0232407 A1 | 9/2012 | Fisher et al. |
| 2012/0310064 A1 | 12/2012 | McGee |
| 2012/0310087 A1 | 12/2012 | Miyaki et al. |
| 2013/0023767 A1 | 1/2013 | Mammone |
| 2013/0060146 A1 | 3/2013 | Yang et al. |
| 2013/0085394 A1 | 4/2013 | Corbett, III et al. |
| 2013/0090554 A1 | 4/2013 | Zvuloni et al. |
| 2013/0172742 A1 | 7/2013 | Rankin et al. |
| 2013/0197357 A1 | 8/2013 | Green et al. |
| 2013/0211254 A1 | 8/2013 | Aase et al. |
| 2013/0331706 A1* | 12/2013 | Hossack ............ A61B 8/4461 |
| | | 600/467 |
| 2014/0005530 A1 | 1/2014 | Liu et al. |
| 2014/0018668 A1* | 1/2014 | Zheng ............... A61B 8/085 |
| | | 600/424 |
| 2014/0051999 A1 | 2/2014 | Gharib et al. |
| 2014/0155748 A1 | 6/2014 | Pernisa et al. |
| 2014/0163369 A1* | 6/2014 | Nair ............... A61B 8/5223 |
| | | 600/407 |
| 2014/0163375 A1 | 6/2014 | Wasielewski |
| 2014/0187925 A1 | 7/2014 | Corl |
| 2014/0213905 A1 | 7/2014 | Saad et al. |
| 2014/0221838 A1 | 8/2014 | Loupas et al. |
| 2014/0270430 A1 | 9/2014 | Nair |
| 2014/0288427 A1* | 9/2014 | Wall ............... A61B 8/0841 |
| | | 600/439 |
| 2015/0088183 A1 | 3/2015 | Vipperman et al. |
| 2015/0223903 A1 | 8/2015 | Bell et al. |
| 2016/0007858 A1 | 1/2016 | Hendriks et al. |

(56) References Cited

U.S. PATENT DOCUMENTS

| | | | |
|---|---|---|---|
| 2016/0098621 | A1 | 4/2016 | Tahmasebi Maraghoosh et al. |
| 2016/0166328 | A1* | 6/2016 | De Vries ............... A61B 90/30 600/7 |
| 2016/0174934 | A1 | 6/2016 | Cong et al. |
| 2016/0238568 | A1 | 8/2016 | Feleppa et al. |
| 2016/0317035 | A1 | 11/2016 | Hendriks et al. |
| 2016/0317119 | A1 | 11/2016 | Tahmasebi Maraghoosh et al. |
| 2016/0324584 | A1 | 11/2016 | Tahmasebi Maraghoosh et al. |
| 2016/0338673 | A1 | 11/2016 | Imai |
| 2016/0350620 | A1 | 12/2016 | Rao et al. |
| 2017/0007161 | A1 | 1/2017 | Zou et al. |
| 2017/0112473 | A1 | 4/2017 | Samset |
| 2017/0119356 | A1 | 5/2017 | Steininger et al. |
| 2017/0238907 | A1 | 8/2017 | Kommu Chs |
| 2017/0296061 | A1 | 10/2017 | Murakoshi et al. |
| 2018/0168539 | A1 | 6/2018 | Singh et al. |
| 2019/0008480 | A1 | 1/2019 | Gerard et al. |
| 2019/0336108 | A1 | 11/2019 | Hope Simpson et al. |

FOREIGN PATENT DOCUMENTS

| | | |
|---|---|---|
| CN | 106491161 A | 3/2017 |
| DE | 102004040869 B3 | 12/2005 |
| JP | 105337111 A | 12/1993 |
| JP | H11169375 A | 6/1999 |
| JP | 2006223512 A | 8/2006 |
| JP | 2008520317 A | 6/2008 |
| KR | 101586977 B1 | 1/2016 |
| KR | 20160099877 A | 8/2016 |
| WO | 2006072050 A2 | 7/2006 |
| WO | 2012071110 A1 | 5/2012 |
| WO | 2014186899 A1 | 11/2014 |
| WO | 2016044411 A1 | 3/2016 |
| WO | 2016164455 A1 | 10/2016 |
| WO | 2016205936 A1 | 12/2016 |
| WO | 2017156023 A1 | 9/2017 |

OTHER PUBLICATIONS

Oussama Hadjerci, Adel Hafiane, Donatello Conte, Pascal Makris, Pierre Vieyres, Alain Delbos, Computer-aided detection system for nerve identification using ultrasound images: A comparative study, Informatics in Medicine Unlocked, vol. 3, 2016, pp. 29-43 (Year: 2016).

Jing Ren, From RF signals to B-mode images using deep learning, Jun. 26, 2018, KTH Institute of Technology School of Engineering Sciences in Chemistry, Biotechnology and Health, pp. iii-40 (Year: 2018).

The 'Hyperthermia Unit' at the Daniel den Hoed Cancer Center, The segmentation group at the IT'IS Foundation for Information Technologies in Society, Hansueli Gerber, iSeg Manual, May 20, 2011 (Year: 2011).

T. Misaridis and J. A. Jensen, "Use of modulated excitation signals in medical ultrasound. Part II: design and performance for medical imaging applications," in IEEE Transactions on Ultrasonics, Ferroelectrics, and Frequency Control, vol. 52, No. 2, pp. 192-207, Feb. 2005 (Year: 2005).

Duhgoon Lee, Yong Sun Kim, Jong Beam Ra, "Automatic time gain compensation and dynamic range control in ultrasound imaging systems," Proc. SPIE 6147, Medical Imaging 2006: Ultrasonic Imaging and Signal Processing, (Mar. 16, 2006) (Year: 2006).

Sep. 1, 2016—(PCT) International Search Report PCT/US16/26206.

Jan. 20, 2016—(PCT) International Search Report PCT/US2015/050404.

Sep. 1, 2016—International Search Report and Written Opinion—PCT/US2016/026206.

Lango, et al., "Navigation Laparoscopic Ultrasound in Abdominal Soft Tissue Surgery: Technical Overview and Perspectives", Int J Cars (2012) pp. 7:585-599.

Light, et al., "Real-Time 3D Laparoscopic Ultrasonography", Ultrasonic Imaging 27, pp. 129-144 (2005).

Hozumi, et al., "Easy and Accurate Targeting of Deep-Seated Hepatic Tumors Under Laparoscopy with a Forward-Viewing Convex-Arrar Transducer", Surg Endosc (2003) 17, Springer-Verlag New York Inc. 2003, pp. 1256-1260.

May 11, 2017—(WO) International Search Report and Written Opinion Appn PCT/US2017/21192.

Olafsson et al., "Ultrasound Current Source Density Imaging of a Time-varying Current Field in a Multielectrode Nerve Chamber". International Ultrasound Symposium, Vancouver, BC, Canada, 2006, pp. 5-8.

Jun. 6, 2018—(EP) Extended European Search Report.

Feb. 27, 2018—(JP) Office Action Appn 2017-534894 with English Tran.

Nov. 12, 2018—(EP) Supplementary European Search Report.

Hadjerci, et al., "Nerve Localization by Machine Learning Framework with New Feature Selection Algorithm", Image Analysis and Processing, Jan. 1, 2015, pp. 246-256.

Chen et al., The Measurement of Backscatter Coefficient from a Broadband Pulse-Echo System: A New Formulation, Mar. 1997, IEEE Transactions on Ultrasonics, ferroelectrics and frequency control, vol. 44, No. 2, pp. 515-525 (Year: 1997).

Manbachi, Amir, et al. Guided pedicle screw insertion: techniques and training [online]. The Spine Journal, Jan. 1, 2014 [available online Apr. 25, 2013] [retrieved on Nov. 6, 2020], vol. 14, No. 1, pp. 165-179. Retrieved from the Internet: <DOI: 10.1016 /j.spinee.2013.03.029>. (Year: 2013).

Aly, Al-Hassan, et al. On Ultrasound Imaging for Guided Screw Insertion in Spinal Fusion Surgery [online]. Ultrasound In Med. & Biol., Apr. 2011 [available online Mar. 3, 2011] [retrieved on Nov. 6, 2020], vol. 37, No. 4, pp. 651-664. Retrieved from the Internet:<DOI: 10.1016/j.ultrasmedbio.2011.01.011>. (Year: 2011).

Jan. 8, 2019—(AU) Examination Report No. 1 Appn 2017229480.

* cited by examiner

METHODS FOR ACCESSING SPINAL COLUMN USING B-MODE IMAGING TO DETERMINE A TRAJECTORY WITHOUT PENETRATING THE THE PATIENT'S ANATOMY

CROSS REFERENCE TO RELATED APPLICATIONS

This application claims priority to U.S. Provisional Patent Application Ser. No. 62/341,966, filed May 26, 2016 and entitled "Methods for Accessing Spinal Column," whose contents are hereby incorporated by reference in their entirety for all purposes. This application also incorporates by reference in their entireties for all purposes the following related applications: International Application PCT/US15/50404, with an international filing date of Sep. 16, 2015 entitled IDENTIFYING ANATOMICAL STRUCTURES, U.S. Provisional Patent Application Ser. No. 62/145,203, filed Apr. 9, 2015 and entitled "Device and Method for Identifying Anatomical Structures", U.S. Provisional Patent Application Ser. No. 62/208,759, filed Aug. 23, 2015 and entitled "Device and System for Placing Securing Device within Bone", U.S. Provisional Patent Application Ser. No. 62/255,840, filed Nov. 16, 2015 and entitled "Retractor System", U.S. Provisional Patent Application Ser. No. 62/051,670, filed Sep. 17, 2014 entitled "DEVICE AND METHOD FOR IDENTIFYING ANATOMICAL STRUCTURES", U.S. Provisional Application Ser. No. 61/847,517, filed Jul. 17, 2013, entitled "Direct Visualization Dissector and Retractor System for Minimally Invasive Procedures", U.S. Provisional Application Ser. No. 61/867,534, filed Aug. 19, 2013, entitled "Ultrasonic Visualization, Dissection, and Retraction System for Minimally Invasive Procedures", U.S. Provisional Application Ser. No. 61/868,508, filed Aug. 21, 2013, entitled "OCT Visualization, Dissection, and Retraction System for Minimally Invasive Procedures", U.S. Provisional Application Ser. No. 61/899,179, filed Nov. 2, 2013, entitled "Nerve Detection System", U.S. Provisional Application Ser. No. 61/921,491, filed Dec. 29, 2013, entitled "System and Method for Identifying Anatomical Structures Ultrasonically", U.S. Provisional Application Ser. No. 61/929,083, filed Jan. 19, 2014, entitled "System and Method for Identifying Anatomical Structures Ultrasonically", U.S. Provisional Application Ser. No. 61/977,594, filed Apr. 9, 2014, entitled "System and Method for Identifying Anatomical Structures Ultrasonically Employing Two or More Transducers", and U.S. Non-Provisional application Ser. No. 14/329,940, filed Jul. 12, 2014, entitled "Device and Method for Identifying Anatomical Structures".

BACKGROUND

Surgical techniques utilizing minimally invasive surgery ("MIS") are being rapidly adapted to replace current traditional "open" surgical procedures. "Open" procedures typically require larger skin incisions that may cause significant collateral damage to uninvolved anatomic structures. For example, intervening soft tissue (e.g., tendons, ligaments, facet capsules, nerves, muscles, and so on) may be cut and even potentially excised to allow for direct surgical visualization of the operated-upon area or anatomical structure.

In contrast, minimally invasive techniques, which may also be referred to as "percutaneous" techniques, involve significantly smaller incisions and are less traumatic to the patient's anatomy. Soft tissues may be preserved with minimal collateral damage to the uninvolved anatomy. Typical benefits of MIS may include decreased blood loss, decreased postoperative pain, smaller scar formation, decreased cost, and a faster rehabilitation for the patient than in "open" or conventional surgical techniques.

Minimally invasive surgery techniques are currently being adapted to a variety of surgical procedures. For example, minimally invasive techniques in the form of laparoscopic procedures, such as a laparoscopic colectomy for carcinoma of the colon, have been developed. More recently, surgeons have utilized MIS in spinal surgery applications.

A method is needed to assist surgeons in avoiding collateral damage to uninvolved anatomy during spinal surgery.

BRIEF SUMMARY

Present MIS techniques are unable to accurately and consistently detect and avoid key anatomical features, such as neural elements, potentially resulting in profound neurological sequelae and deleterious impacts to other systems. For example, even a minimally invasive surgical instrument, if impacting or contacting with nervous system elements (e.g., nerves, spinal cord) may result in loss of sensation, sensory overload, pain, or other unwanted or harmful effects. Detection and identification of anatomical features may assist in combating these problems and other problems that may become apparent upon reading of this disclosure.

Accordingly, in one aspect of the present disclosure, a device may be provided for minimally invasive surgery and may include a body comprising a proximal portion, a distal portion, and a main portion formed between the proximal portion and distal portion. At least one ultrasound transducer may be arranged at the distal portion of the body and may be configured to scan a region extending away from the main portion of the body. The device may include a signal processing unit having at least one processor and memory storing instructions that cause the at least one processor to receive a signal from the at least one ultrasound transducer and identify an anatomical structure based on the signal.

In some embodiments, the device may include a hollow channel and an annular shaped tip to allow the passage of surgical tools in the channel for performing procedures while collecting data for use in mapping anatomical tissues. In these embodiments, ultrasonic transducers may be arranged on the distal end of the device, on the annular shaped tip.

In another aspect, a device may be provided for minimally invasive surgery. The device may include a proximal portion, a distal portion, a main body formed between the proximal and distal portions of the device having a longitudinal axis and at least one ultrasound transducer disposed within the distal portion of the device and configured to scan a region adjacent to a distal end of the distal portion of the device.

In another aspect, a method may be provided and may include receiving data from at least one ultrasound transducer arranged at a distal portion of a body and configured to scan a region extending away from a main portion of the body. The method may also include processing the data to identify an anatomical structure located within the region, and outputting an indication associated with the anatomical structure.

In another aspect, a method for identifying a target anatomy may be provided with a device having a distal portion and at least one ultrasound transducer at least partially disposed within a main body of the device. The method may include scanning an anatomy of a patient anatomy for the target anatomy, determining a voltage trace of the patient's anatomy, comparing the voltage trace of the patient's anatomy to a predetermined voltage trace of the target anatomy, and sending a notification if the voltage trace of the patient's anatomy matches the predetermined voltage trace of the target anatomy.

In another aspect, a method for identifying a clear path through a patient's muscle may be provided with a device having at least one ultrasound transducer. The method may include scanning an anatomy within a patient's muscle for a target anatomy, determining a voltage trace of the anatomy, comparing the voltage trace of the anatomy to a predetermined voltage trace of the target anatomy, determining a clear trajectory through the patient's muscle which avoids the target anatomy, and outputting an indication of the clear trajectory.

In another aspect, the method may include scanning the patient's anatomy, determining a voltage trace of the anatomy, comparing the voltage trace of the anatomy to a predetermined voltage trace of a muscle, determining a clear trajectory through the patient's anatomy which does not pass through anatomy other than muscle, and outputting an indication of the clear trajectory.

In another aspect, the method may include scanning a patient's anatomy, determining a voltage trace of the anatomy, comparing the voltage trace of the anatomy to a predetermined voltage trace of a target anatomy, determining a clear trajectory through the patient's anatomy which avoids the target anatomy, and outputting an indication of the clear trajectory.

DETAILED DESCRIPTION

Figure 1:
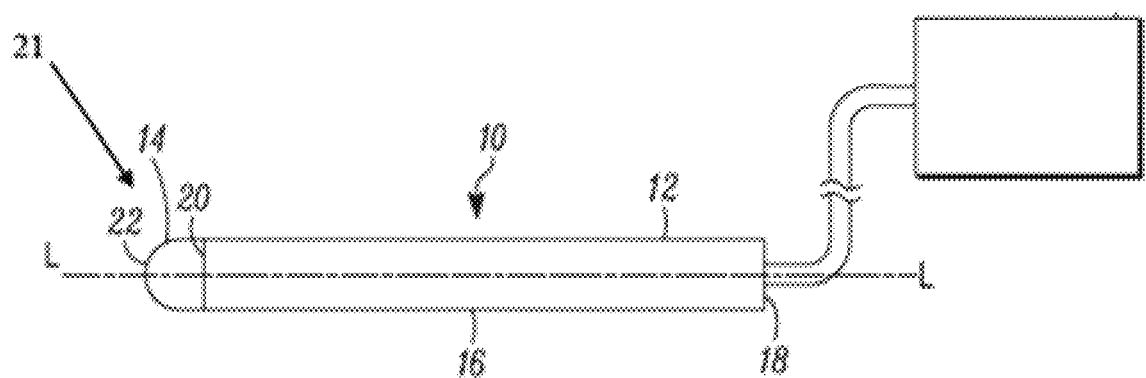
FIG. 1 is a side view of one embodiment of a device.

To help understand the present disclosure, the following definitions are provided with reference to terms used in this application.

Throughout this specification and in the appended claims, when discussing the application of aspects of the present disclosure with respect to the body's tissue, spine or other neural elements, the term "proximal" with respect to such a device is intended to refer to a location that is, or a portion of the device that is, closer to the operator. The term "distal" is intended to refer to a location that is, or a portion of the device, further away from the operator.

The embodiments below are described with reference to the drawings in which like elements are referred to by like numerals. The relationship and functioning of the various elements are better understood by the following detailed description. The embodiments as described below are by way of example only and the present disclosure is not limited to the embodiments illustrated in the drawings.

According to one or more aspects of the present disclosure, a device capable of detecting target anatomical structures may be provided. In some embodiments, the device may be used to facilitate placement of a securing device, such as a pedicle screw. The device may utilize ultrasound and/or Optical Coherence Tomography (OCT) technology as the device is being advanced through a patient's anatomy. The device may have a distal portion having a tip, where the tip can be used to dissect a patient's anatomy without puncturing or tearing the patient's anatomy and while simultaneously allowing the device to inspect the anatomy as it is being dissected by the tip. While the device discussed herein is discussed in the context of a device that can be held by an operator, it is contemplated that the device and/or parts of the device may be used during automated procedures such as those being performed by robotic and other similar systems.

In one embodiment, shown in FIG. 1, the device 10 has a proximal portion 12 and a distal portion 14 with a main body 16 disposed between the proximal and distal portions (12 and 14, respectively). The main body 16 has a proximal end 18 and a distal end 20 and is defined by a longitudinal axis L. The proximal end 18 may have a handle (not shown) or gripping portion (not shown) attached thereto. The length of the main body 16 may vary, but can include a length of 50 to 300 mm; however, in some embodiments the length may fall outside of this range. Similarly, the outer diameter of the main body 16 may vary and can include an outer diameter of between 3 mm and 20 mm. The main body 16 can be made out of any preferable surgical grade material, including but not limited to, a medical grade polymer including PEEK (polyether ether ketone), stainless steel, carbon fiber, and titanium. The main body 16, and one or more of the components of the device 10 generally, may contain radio-opaque markers to allow an operator to detect the location of the device 10 with respect to the anatomy of a patient via radiographic imaging.

As shown in FIG. 1, the distal portion 14 of the device 10 includes a tip 22. The tip 22 may be hemispherical in shape, as illustrated in FIG. 1, but it is contemplated that the tip 22 may also be of a different shape. For example, and without limitation, the tip 22 may have a semi-spherical, conical, pyramidal, spear or aspherical shape. The tip 22 may be configured to dissect a patient's anatomy, such as a muscle, without tearing or disrupting the patient's anatomy as it passes through the tissue. As a result, the outer diameter of the tip 22 may have a diameter ranging anywhere between 1 mm and 50 mm and preferably between 2 mm and 9 mm. It is appreciated that the outer diameter of the tip 22 may fall outside of this range as well. It is further appreciated that the tip 22 is optional such that particular embodiments of the device 10 may not include the tip 22.

Figure 2:
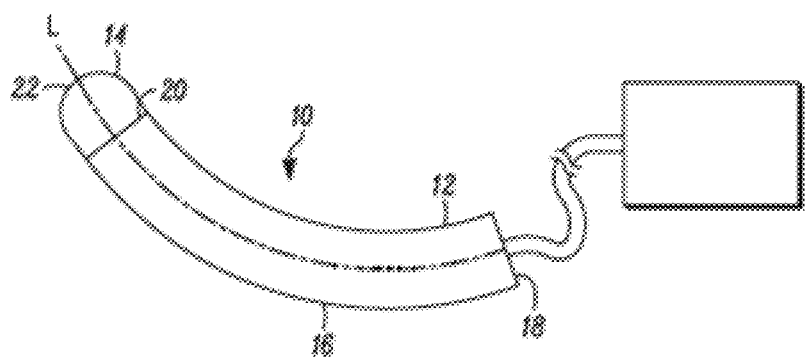
FIG. 2 is a side view of another embodiment of the device of FIG. 1.

As illustrated in the embodiment shown in FIG. 1, the main body 16 of the device 10 may be substantially straight. However, it is contemplated that the main body 16 may have different shapes, including having a curved shape with a non-zero radius of curvature. An example of such an embodiment is illustrated in FIG. 2, which may be used for MIS requiring access through the presacral space of a patient. The main body 16 may also take on an "L", "C", "U" shape or a shape there between.

The device 10 may include ultrasonic capability. A purpose of this device may be to serve as an instrument that features a specifically patterned array of high frequency ultrasound transducers and a monitoring system that collects spectral properties of specific tissue or structures in the body. For example, the system may be able to detect the spectral properties of muscle, fat, nerve and bone, including the types of bone. As the anatomy is stimulated by the ultrasound transducer(s), it will emit a specific spectral property that can be detected by the monitoring system. The system may examine scan line images and seek specific parameters of amplitude, shape, and other spectral content in order to differentiate the signals coming from the target anatomy and signals coming from surrounding anatomy. For example, nerve tissue may be hypoechoic as compared with the surrounding tissue. There are internal structures that provide features in the signal that identify the nerve from single scan lines or RF properties. The system will inform the operator that the device is adjacent to or proximate to the specific type of anatomy that is detected by the system. The device can allow a surgeon to identify and avoid certain portions of a patient's anatomy (e.g. nerve) when performing a minimally invasive procedure.

Furthermore, different types of bone may have different pore properties, different densities and tortuosities. Bone may be modeled as a porous solid (Biot theory) that supports both fast and slow waves. Because cancellous bone is soft as compared to the surrounding hard cortical bone, it has different ultrasound properties, and, as disclosed herein, it is possible to distinguish between different types of bones based on these properties. As will be discussed in greater detail below, the device 10 may detect between different types of bone, based on characteristics such as, but not limited to, impedance and attenuation.

Figure 3:
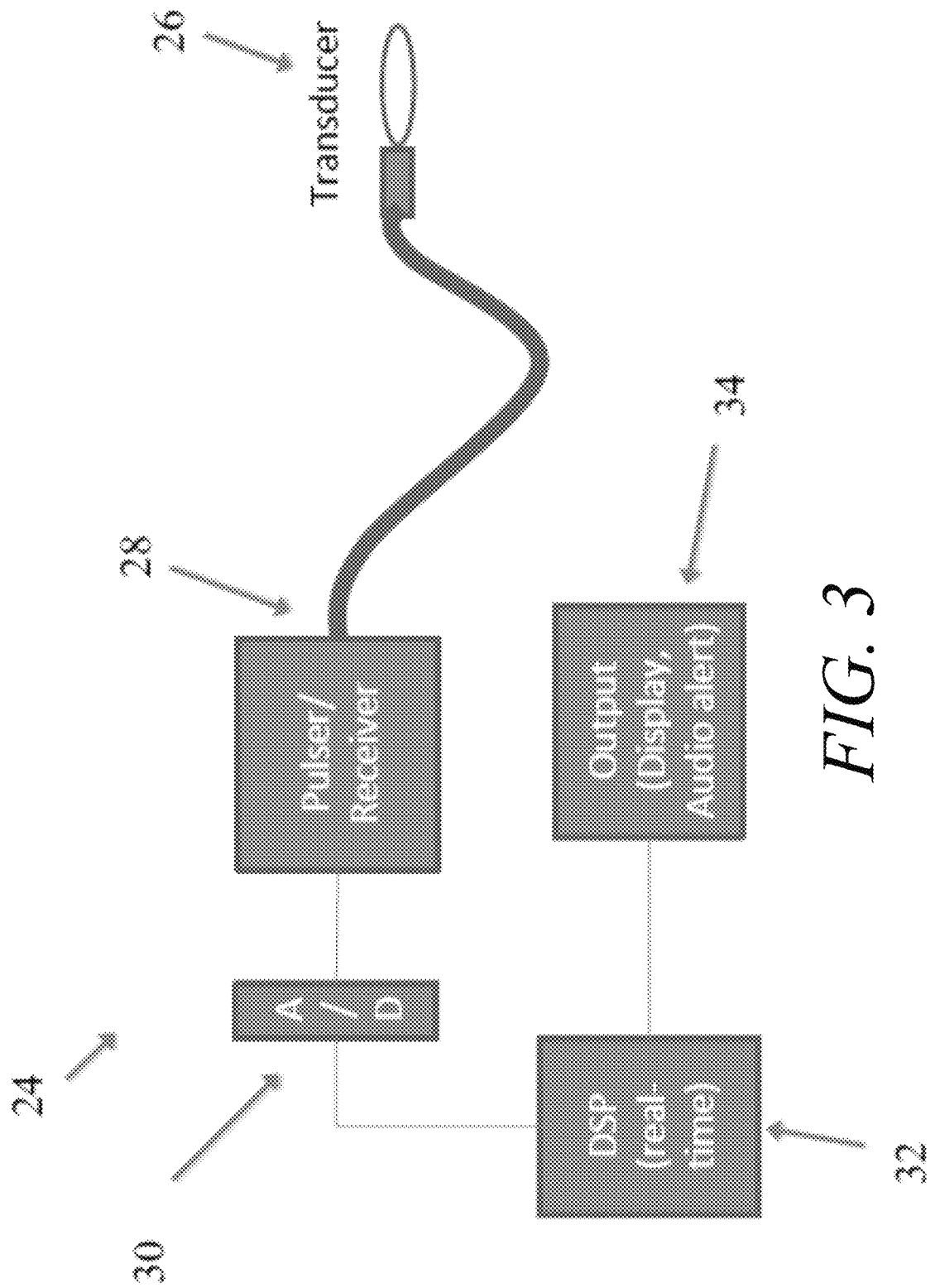
FIG. 3 is a functional diagram of the ultrasound imaging system that may be used in one embodiment of the present disclosure.
Figure 4:
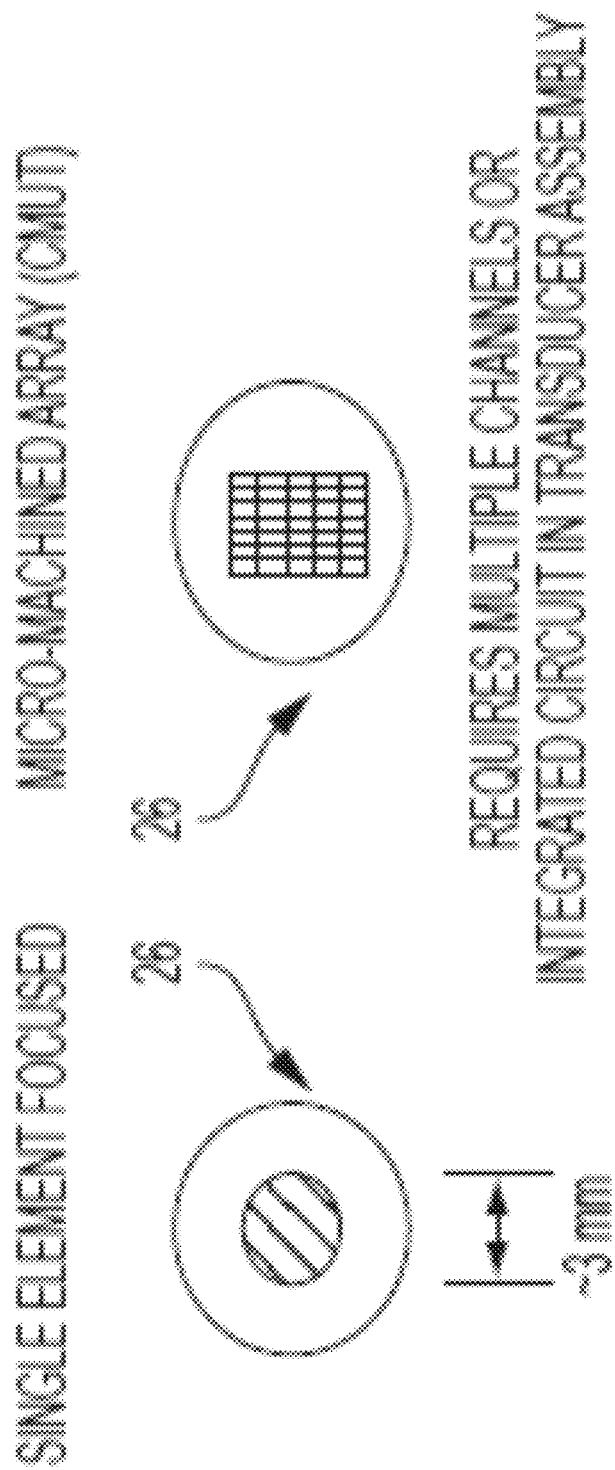
FIG. 4 is a diagram of an ultrasound transducer that may be used in one embodiment of the present disclosure.
Figure 5:
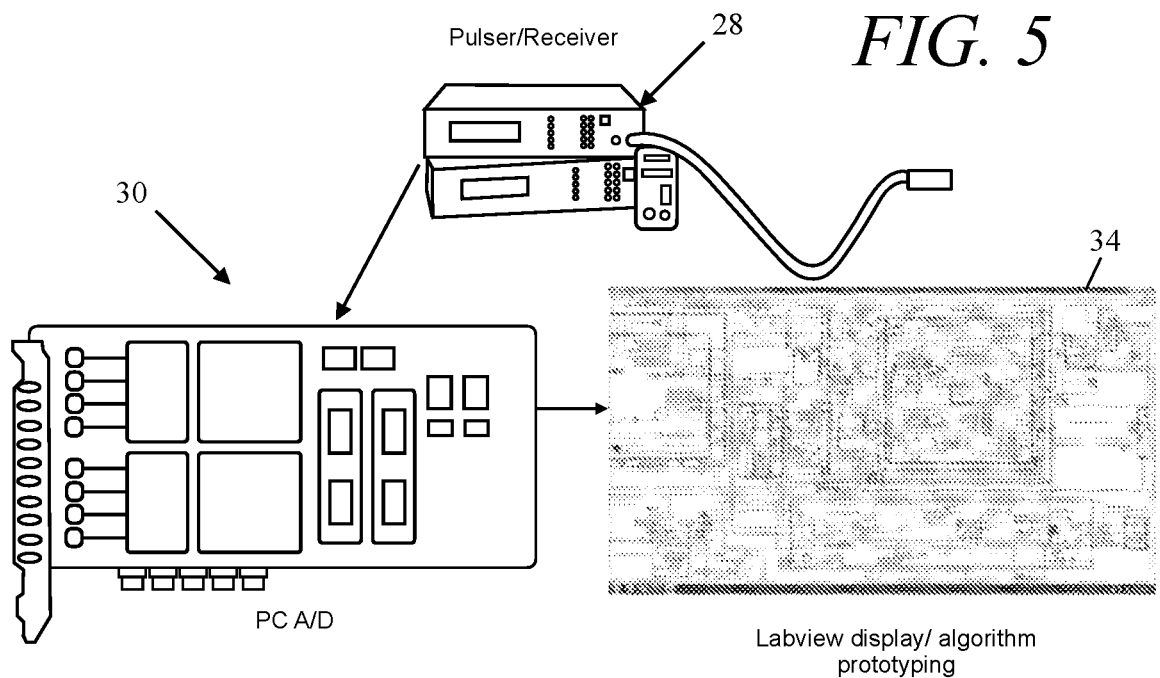
FIG. 5 is another functional diagram of one embodiment of the ultrasound imaging system that may be used in an embodiment of the present disclosure.

The device 10 may be equipped with ultrasound imager 24 to detect a patient's anatomy as shown in FIGS. 3-5, such as nerve and/or the characteristics of bone (e.g., impedance and attenuation). The detection of nerve and characteristics of bone may be done simultaneously by using the same device 10 and ultrasound imager 24. The ultrasound imager 24 may include a transducer 26 that is configured to emit sound waves and may be disposed at the distal end 20 of the device 10. As shown in FIG. 4, the transducer 26 may include a single element focused transducer, and may have a frequency operation range that includes an operating range of approximately 10-40 MHz. In some aspects, the operating range may be higher or lower than this range of frequencies. Additionally or alternatively, transducer 26 may include a micro machined array, such as a capacitive micromachined ultrasonic transducer (CMUT), having multiple channels. The desirable frequency may vary depending on the application and target anatomy. For example, in one embodiment a frequency or range of frequencies may be selected for detecting nerve from surrounding tissues and adjacent anatomy on b-mode (2D) ultrasound images based on image texture and echogenicity. Reliably distinguishing between nerve and muscle tissue in real time may require quantitative approaches, and may require automated or manual calibration of the system to estimate tissue-specific properties. In some aspects, a meta-analysis comparing ultrasound to nerve-stimulation may result in superior outcomes for ultrasound guidance.

As shown in FIGS. 3 and 5, the transducer 26 may be in communication with a RF-pulser/receiver 28, which may be in communication with an analog to digital converter 30, which may be in communication with a digital signal processor 32 and an output 34 such as a monitor.

In one embodiment, the transducer 26 converts an electric signal or pulse generated from the RF-pulser/receiver 28 into a sound wave and then converts a reflected sound wave back into an electrical signal. The ultrasound transducer 26 launches sound pulses, which may be short, high-frequency non-damaging sound pulses, into the tissue, and then may wait to hear the reflection from the tissue. Since the speed of sound in tissues is high (1500 m/s), this process may take a few milliseconds to image a few millimeters of tissue. As referenced above, the RF-pulser/receiver 28 may generate an electrical impulse that may be sent (e.g., via a cable) to the transducer 26 to generate a sound wave, and may also receive a signal from the transducer 26 generated by the reflected sound waves that the transducer 26 receives. The analog to digital converter 30 converts the analog radiofrequency signal received from the transducer 26 into a digital form that a computer may analyze. The digital signal processor 32 processes the digitized signal received from the digital converter 30. Signal filtering and processing operations may be programmed into the hardware, firmware, and/or software of various components of the system (e.g., the digital signal processor 32) to detect the reflected signal properties of the tissue and distinguish between nerve and muscle tissues in real-time. Once a nerve tissue signature is detected, a hardware, firmware, and/or software system may communicate with the output 34. The output 34 may include a visual monitor that may be programmed to display the anatomy or signals indicative of the anatomy (e.g., via actual images or programmable color configurations (red/yellow/green)) and/or a sound-generating device which may be controlled to emit an audible indicator (e.g. alarm or a "beep"). For example, the sound-generating device, such as a speaker, may emit a "beep" when the device 10 encounters/detects the presence of target anatomy (e.g. nerve) within a predetermined range (e.g. 1 mm to 10 cm).

Alternatively, the shaft of the device can include one or more LEDs or visual indicators that are circumferentially around the shaft that can flash a color (e.g., green yellow red) to notify the user of the location of the probe with respect to the target anatomy without having to look at a screen or display. In addition, the numerical distance from the distal portion of the device 10 and the target anatomy may be displaced on the shaft of the device 10 or on the top portion of the device 10 in a position that can be easily viewed by the surgeon during operation.

It is appreciated that one or more of these components may be in wireless communication with one another, may be combined into one or components, and other additional components may be in communication between each of these components or one or more identified components and may not be included in a particular embodiment.

Figure 6:
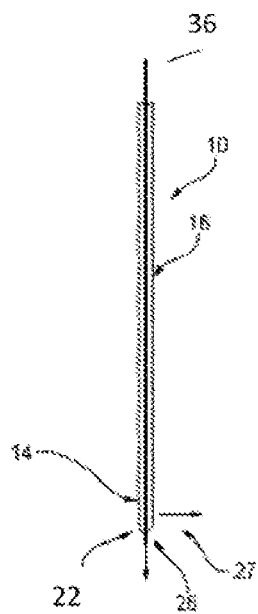
FIG. 6 is one embodiment of the device having more than one ultrasound transducer disposed therein.

In one embodiment, the outer diameter of the transducer 26 may be approximately 3 mm, but may range anywhere between approximately 1 mm and 10 mm. Further, the transducer 26 is configured to be disposed in a variety of locations with respect to the device 10. For example, as shown in FIG. 6, the transducer 26 may be disposed at the distal end 20 of the main body 16 or at the tip 22 portion of the distal end 20. The transducer 26 may also be removable such that it can be removably disposed within a conduit 36 formed within the device 10 and removed once a working space is identified and accessible. In some aspects, the working space may be the space created by insertion and/or manipulation of the device 10 within the patient's anatomy.

Multiple transducers 26 may be provided as part of the device 10. In some aspects, two or more transducers 26 may be side positioned (e.g. on either side of the main body 16) so as to provide for multi-directional scanning of the patient's anatomy to detect a nerve and/or detect different types of anatomy (e.g., nerve and bone). The side positioned transducers may be configured to scan the anatomy around in a circumferential direction around the main body 16, and may detect the nerve (or other target anatomy) that was not detected by a transducer positioned at the distal end 20 of the main body 16. The multi-directional scanning enables the system to generate a scan image of the patient's anatomy in multiple directions as the device 10 is advanced through the patient's anatomy.

Returning to FIG. 6, the device 10 may include at least one ultrasound transducer 26 (such as a high frequency ultrasound transducer) that is used to stimulate a patient's anatomy, such as muscle, fat, nerve, and bone, and so on. A series of transducers 26 (e.g., a transducer, two or more transducers) may be disposed along the length of the device 10 to allow for a wider pattern of ultrasonic stimulation of the surrounding anatomy or to detect different types of anatomy (e.g., nerve, bone, blood vessels). In some embodiments the detection of different types of anatomy may be performed simultaneously or sequentially. In this embodiment, there may one transducer 26 on the distal end of the device 10 that emits an ultrasonic frequency in a direction that is substantially parallel to the longitudinal axis of the device 10. There may be another transducer 27, adjacent to the first transducer 26, that emits ultrasonic frequency along a path that is substantially perpendicular to the longitudinal axis of the device 10. It can be appreciated that the transducers 26 and 27 can be orientated in any direction that is required for the particular application. In some embodiments, there may be a forward looking transducer and a side looking transducer. In such embodiments, the side looking transducer may provide directional information to a surgeon or other user. For example, the device 10 may be spun in a circle and the side looking transducer may help the surgeon determine locations of various tissues.

Figure 7:
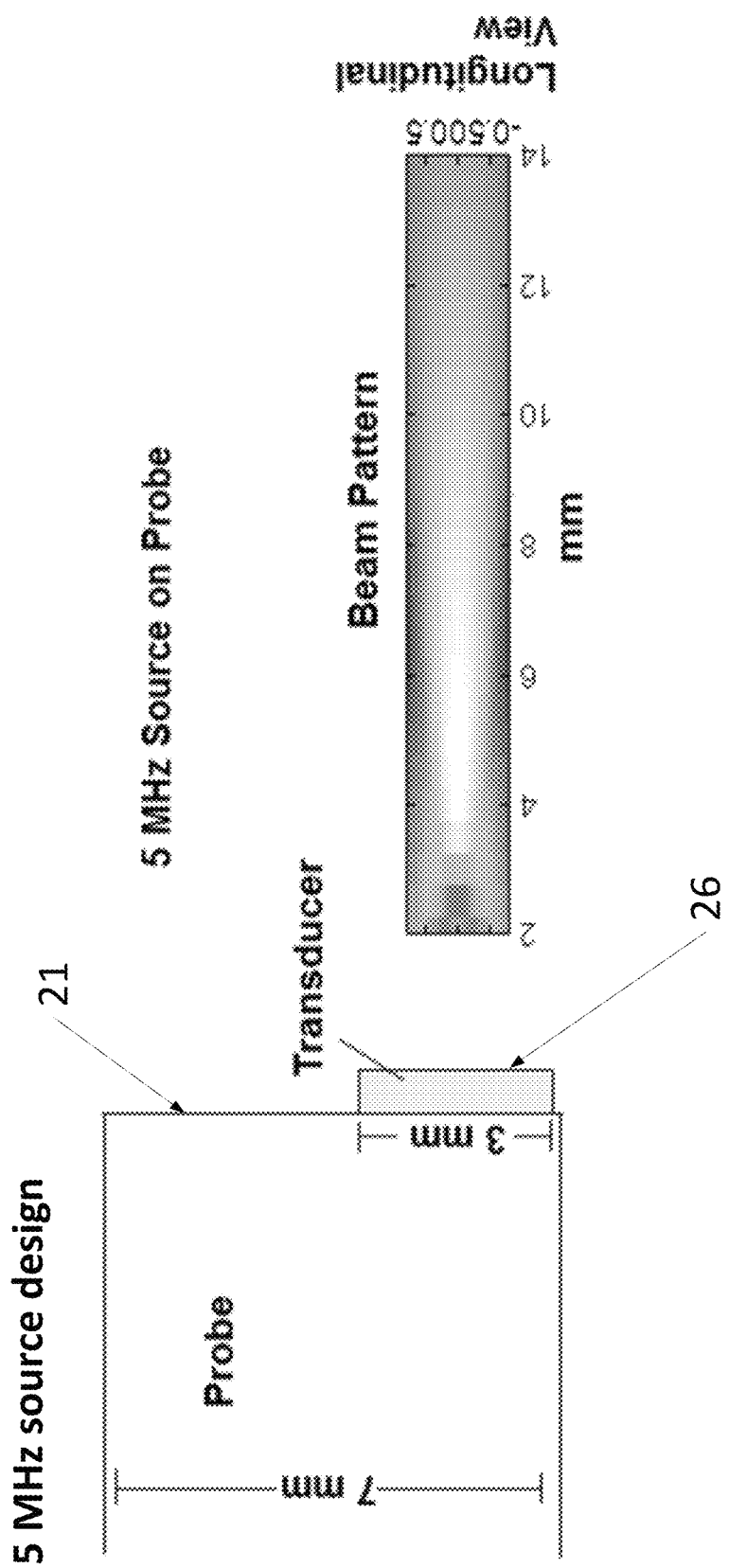
FIG. 7 is another embodiment of the device having one ultrasound transducer disposed therein.
Figure 8:
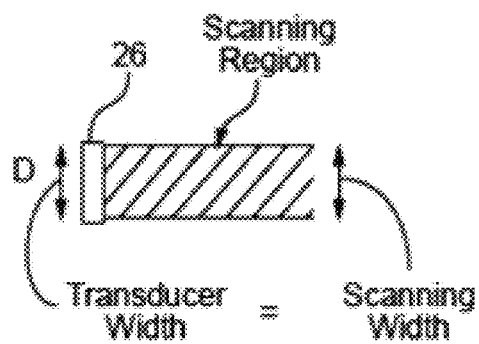
FIG. 8 depicts the scanning width of a transducer.

FIG. 7 depicts one embodiment where a 5 MHz transducer 26 is located on the distal end 21 of the device. In such an embodiment, the diameter of the transducer 26 may be 3 mm and the transducer may be forward facing. In such an embodiment, the scanning range is approximately 14 mm. In some aspects, an area of the scanning region (hatched section in FIG. 8) by a transducer 26 may not exceed the outer diameter of the transducer. This may be because the scanning width is circumscribed by the outer diameter of the transducer 26 and the peripheral limitations of the transducer 26 such that the transducer 26 cannot identify or scan a region that lies beyond of the diameter of transducer 26.

Figure 9:
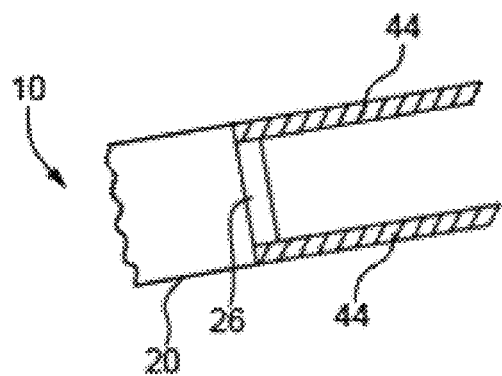
FIG. 9 depicts the scanning width of a transducer in one configuration.

Accordingly, in some aspects such as those disclosed herein where the transducer 26 is housed within a device 10, the transducer 26 may be unable to scan the region that is directly front of (distal to) the outer portions of the device that houses the transducer 26. This region 44 is depicted in FIG. 9. One result of this is that the target anatomy may go undetected if it is positioned beyond the scanning region of the transducer 26.

Figure 11:
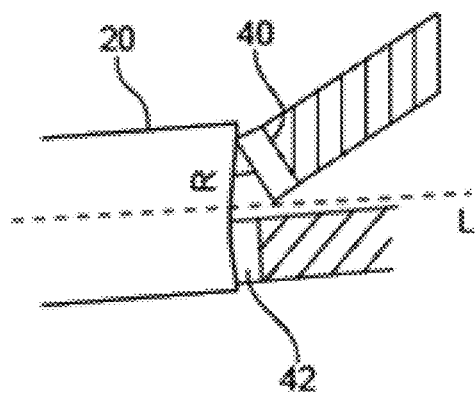
FIG. 11 depicts the scanning width of the embodiment of FIG. 10.
Figure 10:
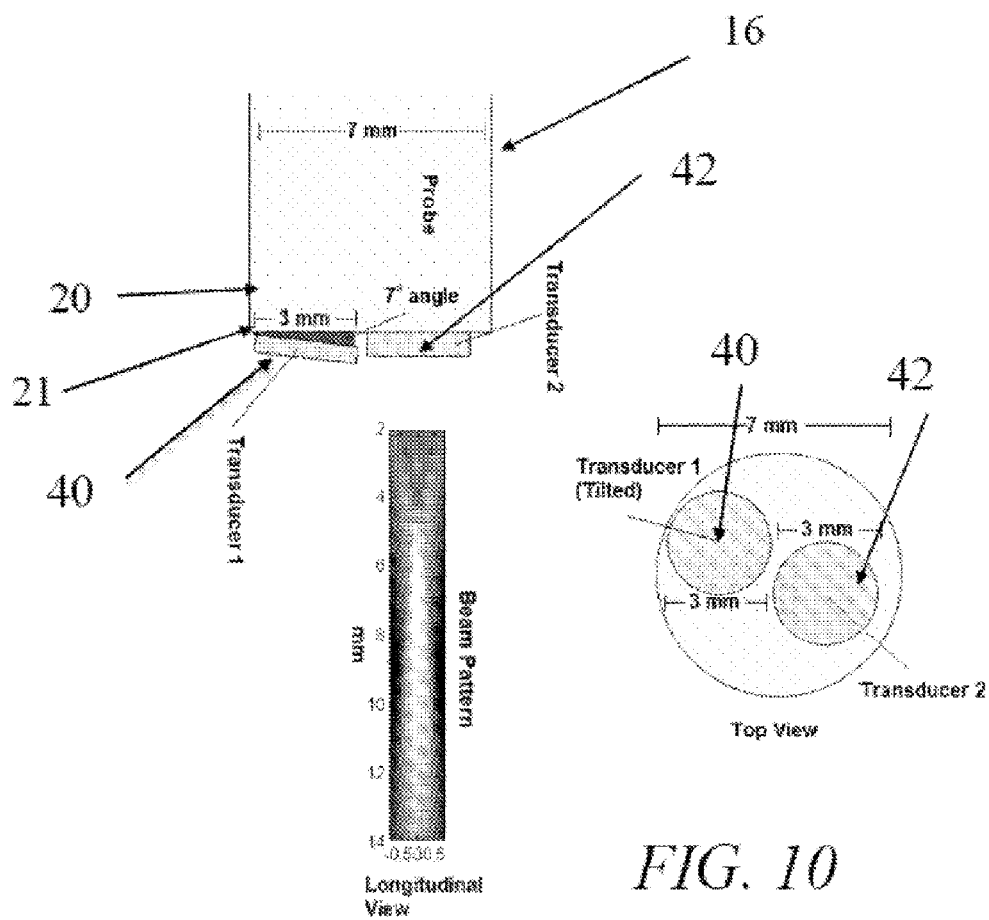
FIG. 10 is another embodiment of the present disclosure where one of the transducers is positioned at an angle with respect to the other transducer.

In some aspects, for example to detect target anatomy that lies just beyond the scanning region of the transducer 26 (i.e. outside of the scanning diameter), the device 10 may include two or more transducers positioned at an angle relative to one another. For example, as shown in FIGS. 10 and 11, the first transducer 40 may be positioned at an angle with respect to the outer edge of the main body 16. The angle may be measured from the face of distal end 21 of the device 10, or may be measured from the horizontal axis that intersects the longitudinal axis of the device 10. The angle α in this embodiment is 7° but it is appreciated that it can vary from 0° to 180° depending on the particular embodiment. Further, in this embodiment, the angle may be formed between the edge of the transducer 26 and the adjacent outer edge of the main body 16.

Figure 12:
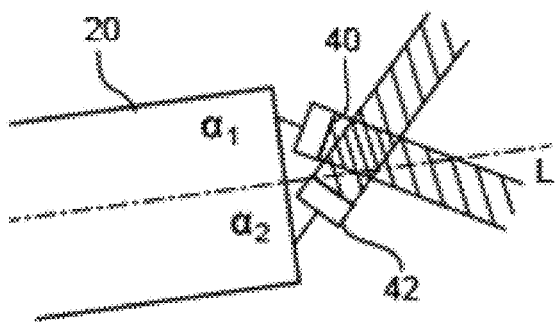
FIG. 12 is yet another embodiment of the present disclosure where two transducers are angled towards the longitudinal axis of the device.

Transducer 40 may be angled with respect to any portion of the main body 16. For example, the first transducer 40 may be angled by pivoting the first transducer 40 about the portion positioned along, or closest to, the longitudinal axis of the main body 16 as shown in FIG. 12. Specifically, as shown in FIG. 12, the transducers 40, 42 may be angled towards the longitudinal axis of the main body 16 such that the angle of tilt, al aa, are measured as the angle of the transducer from the longitudinal axis of the main body 16.

In the embodiment shown in FIG. 10, the first transducer 40 may be positioned at an angle (e.g., 7° from the edge of the main body 16) allowing the first transducer 40 to scan a region extending beyond the outer edge of the main body 16. Angling the first transducer 40 may allow the device 10 to scan and detect any target anatomy residing outside of the scanning region of a transducer that is not angled with respect to the main body 16 of the device. A region that may be scanned by the first angled transducer 40 in this particular embodiment is shown in FIG. 10.

The two transducer elements may fit on the tip of a device 10. This may allow, for example, the device 10 to detect backscattered signals. In some aspects, the device 10, and/or the two transducer elements may be configured to detect the presence of nerves or other neural elements existing distally up to 1 cm from the probe tip 22 (e.g., the nerves or neural elements may be in the pathway of the device). In some aspects, a device may be provided with transducers having different stimulating frequencies (e.g., a first transducer 40 may stimulate with a frequency of 5 MHz, and a second transducer may stimulate with a frequency of 10 MHz). Beam patterns or fields emitting from the sources may be modeled using an ultrasound simulation program assuming an element diameter of 3 mm and a focal number of 3 (f/3).

In some aspects, two transducer elements 40, 42 may be positioned at the tip of the probe. The tilted transducer element 40 faces outward with an angle of tilt, such as 7°. The tilted element may have one end at the edge of the probe. The un-tilted transducer element 42 may be centered from the edge of the distal portion of the device 10. This configuration may allow the device 10 to be rotated as it is snaked through the tissue so that the cross sectional surface area of the probe may be at least 1 cm above the probe surface.

The diameter of the transducers 40, 42 may vary and can range from 1 mm to 20 mm. For example, in the embodiment shown in FIG. 10, the first transducer and second transducers 40, 42 each have a diameter of approximately 3 mm. It is not necessary for the transducers to have the same diameter of one another and they may be staggered as shown in the top view of FIG. 10.

The main body 16 can be rotated so as to allow the first transducer 40 to scan the entire outer region to detect whether any target anatomy is present that is just beyond the scanning area of a forward facing transducer. By rotating the main body 16 about its longitudinal axis, the first transducer 40 can scan the outer region that does not fall within the scanning region of a transducer that is not angled with respect to the main body 16 of the device.

The number of angled transducers may vary and they may be positioned at various angles with respect to the distal end of the main body 16. For example, as shown in FIG. 12, the first and second transducers 40, 42 are positioned toward one another so that their scanning areas cross to provide a scan of the area distal to the distal portion 14 of the device 10 and a region beyond the area directly in front of to the outer diameter of the transducers 40, 42 as shown in FIG. 9. Also, the transducers 40, 42 may be positioned at an angle on more than one axis with respect to the distal end of the main body 16.

The device 10 can be configured to determine the b-mode scans of the patient's anatomy (e.g., nerve) and associated data, including, for example, the voltage trace from a scan line in the b-mode image. The voltage trace for certain anatomical parts (e.g., a nerve) may have a unique voltage trace that may be used to detect like anatomical parts within the patient's anatomy. One way to detect like anatomical parts may be by comparing the voltage trace from a scan line of a b-mode image to the known voltage trace from the scan line of the target anatomy. Specifically, the b-mode scans (and associated data, such as a-scan lines, voltage traces, and the like) may be captured by the device 10. The scans and/or data may be compared to the pre-determined b-mode scans (and associated data) of known anatomical features (e.g., nerve) to determine whether the region captured by the b-mode scan from the device 10 contain the target anatomy.

The device 10 may be used in conjunction with a neuromonitoring system capable of detecting certain portions of a patient's anatomy, including neural elements that include a nerve, nerve bundle, or nerve root. For the purposes of this discussion, the device 10 and neuromonitoring system will be discussed with respect to detecting a patient's spinal nerve but it is contemplated that the device 10 and neuromonitoring system can be used to detect other nerves (peripheral and central) as well as the spinal cord. One type of neuromonitoring system that can be used in conjunction with the device 10 is disclosed in U.S. Pat. No. 7,920,922, the entirety of which is incorporated by reference herein.

Experimentation

The discussion below is directed to the experiment used to determine the target ultrasonic frequency that can be used to detect nerve using the device 10 and whether the b-mode scan images captured by the device 10, which is inserted into the patient's anatomy, is comparable to results captured by traditional non-invasive ultrasound devices. Both target objectives were accomplished using the following process.

Figure 13:
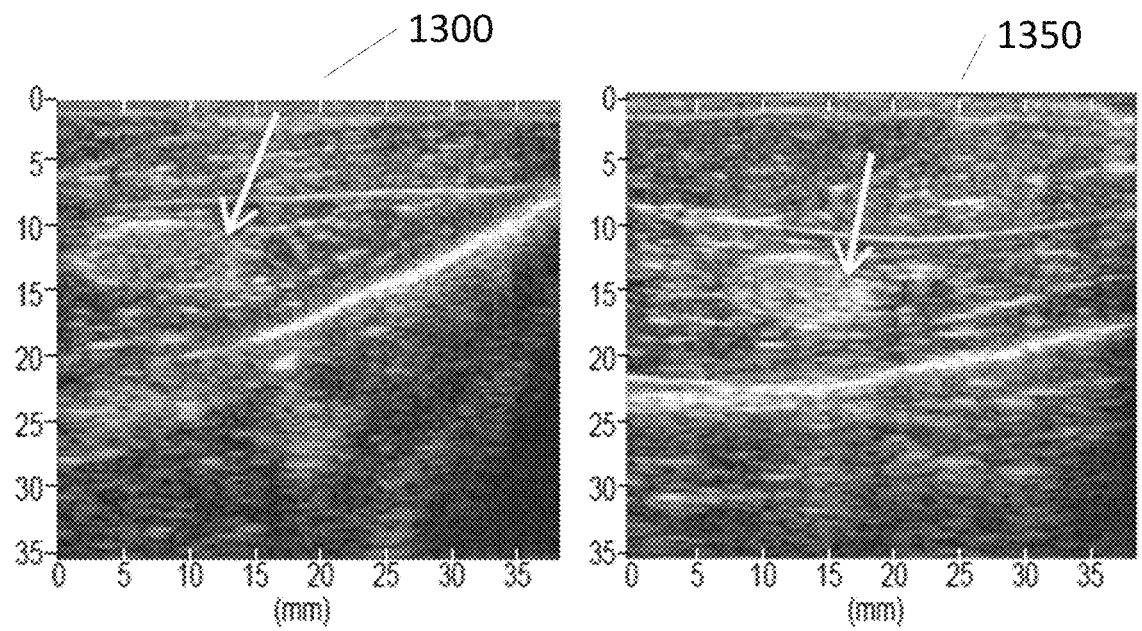
FIG. 13 depicts scan images of a target anatomy taken by one embodiment of the present disclosure.

FIG. 13 illustrates exemplary data indicative of a scan of a sciatic nerve of a rabbit with a clinical ultrasound array system. The scan was performed before and after euthanizing the rabbit to be sure that the nerve could be seen in both cases. FIG. 13 depicts b-mode images (nerve cross-sectional view) for alive (left, image 1300) and dead (right, image 1350). The nerve may be seen in each case (area pointed to by white arrow on image 1300 and image 1350).

Figure 14:
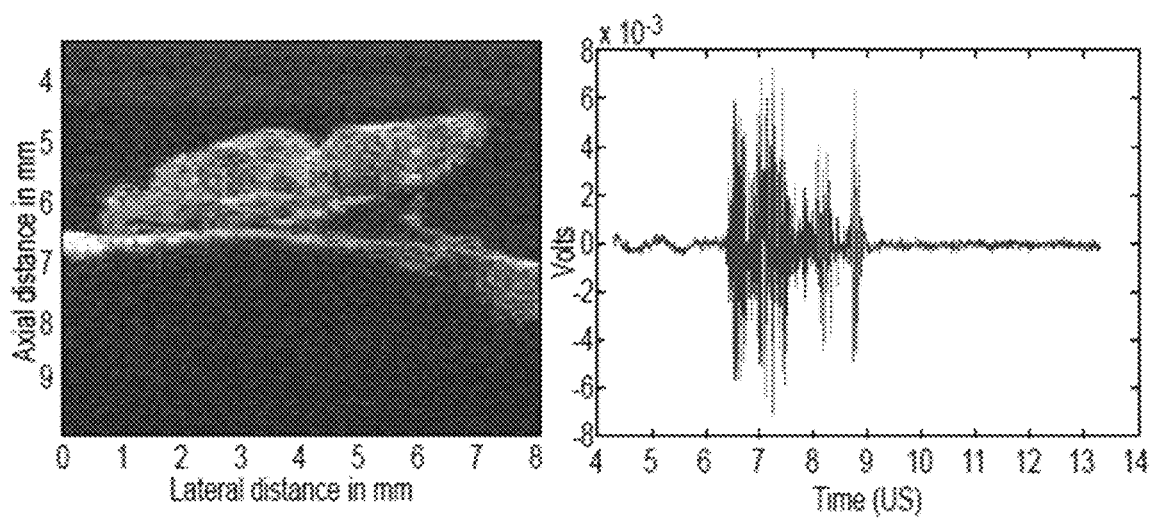
FIG. 14 is a scan and A-line image scan of the target anatomy captured by one embodiment of the present disclosure.

The nerve was scanned using a high frequency (40 MHz) probe with the bottom of the nerve still attached to the muscle and the nerve centered in the probe's depth of field. FIG. 14 illustrates a b-mode image 1400 of this scan. The image 1400 shows (from top to bottom): water, nerve, and muscle. The nerve separates from the muscle towards the right side of the image, and you can see a gap between the nerve and the muscle. FIG. 14 also illustrates a plot 1450 depicting the voltage trace from a scan line in the center of the b-mode image, indicated by the vertical line.

Figure 15:
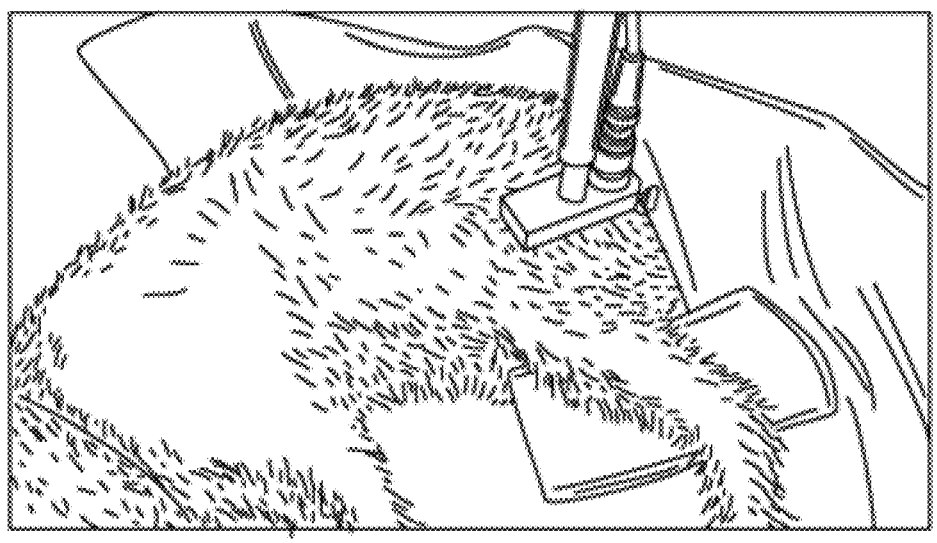
FIG. 15 depicts the configuration of one embodiment of the present disclosure.

The hind limb sciatic nerve was scanned with a 20 MHz single-element probe though the leg muscle. The muscle was kept intact, and the skin removed to provide a window to see into the muscle. The image 1500 shown in FIG. 15 illustrates the setup.

Figure 16:
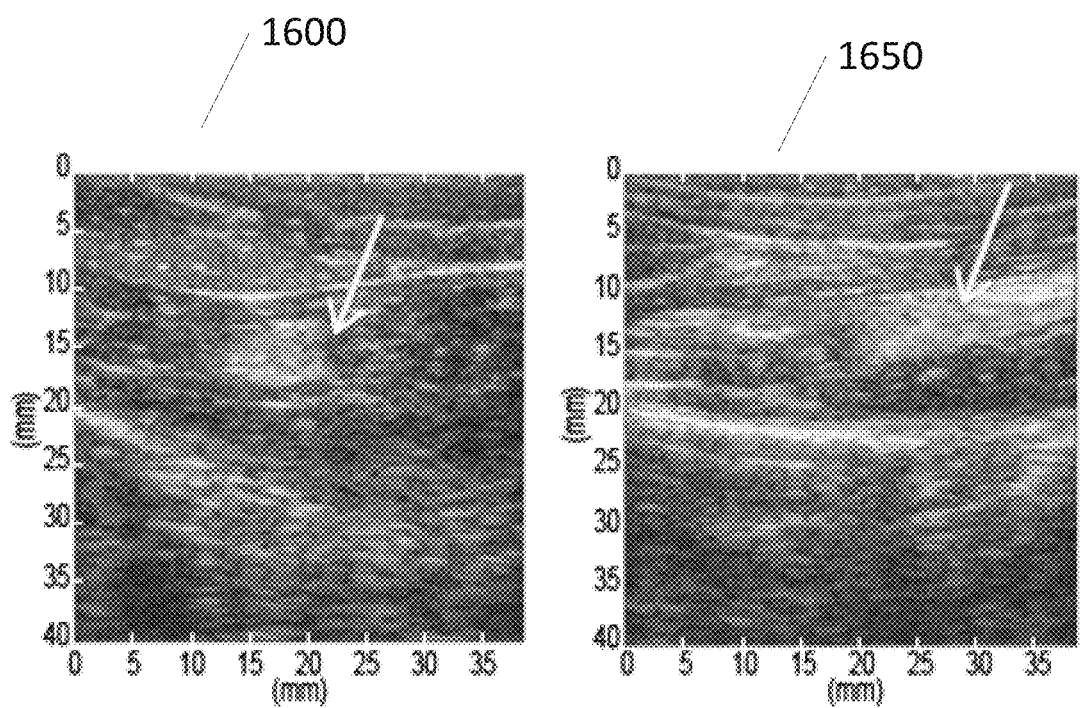
FIG. 16 depicts images of the target anatomy captured by one embodiment of the present disclosure.
Figure 17:
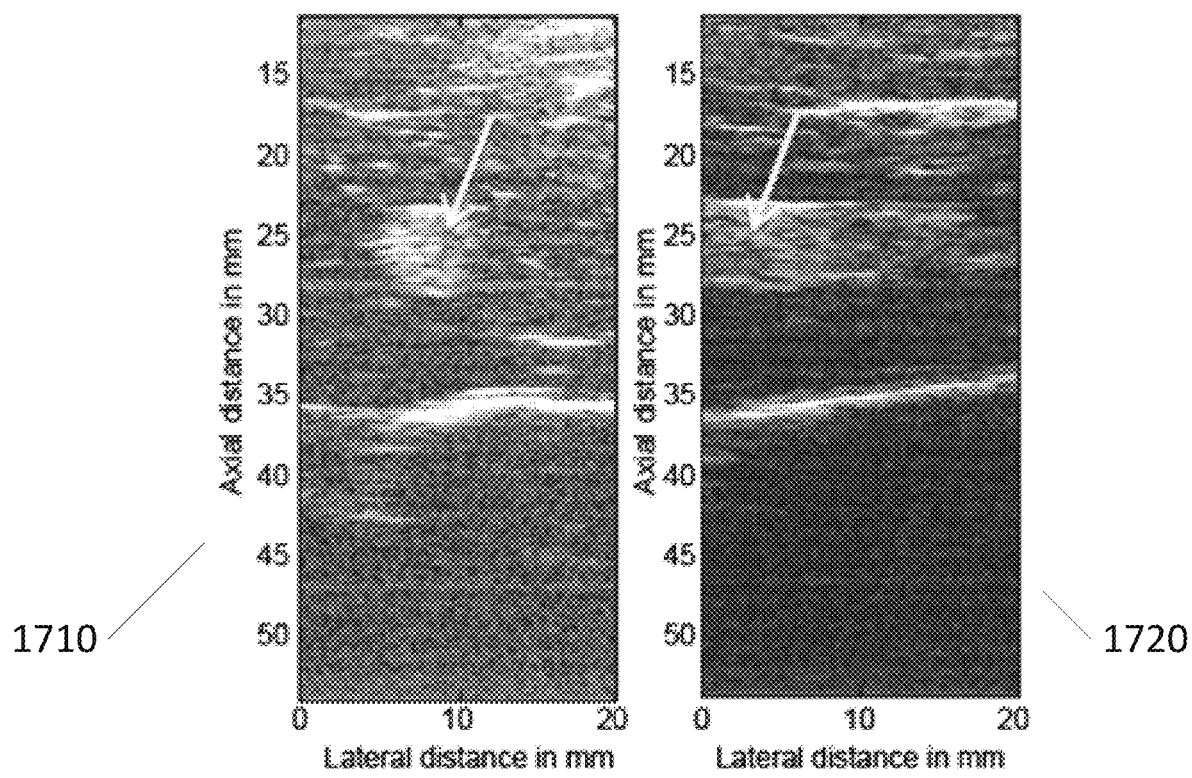
FIG. 17 depicts additional images of the target anatomy captured by one embodiment of the present disclosure.

A clinical scan was performed before scanning with the 20 MHz probe. Images 1600 and 1650 from the clinical scan of the nerve are shown in FIG. 16, and images 1710 and 1720 from the scan performed by the 20 MHz probe are shown in FIG. 17. A comparison between the clinical imaging system and the 20 MHz probe system suggests that both techniques produce similar images. For example, the cross-section and length-wise (with respect to the long direction of the nerve) scan planes both show the nerve in the background muscle for both the clinical system and the 20 MHz system.

The 20 MHz results are important for at least two reasons: First, the results show that the contrast inside the muscle exists at 20 MHz as demonstrated in the left image 1710 in FIG. 17. Second, the depth of penetration for the 20 MHz signal was sufficient to be seen at more than 1 cm of depth. This may be the distance away from the surgical probe required for detecting the nerve. Therefore, this suggests that if the signals can be used to detect the nerve, the signal strength and penetration should not be an issue at the chosen ultrasound frequencies.

Figure 18:
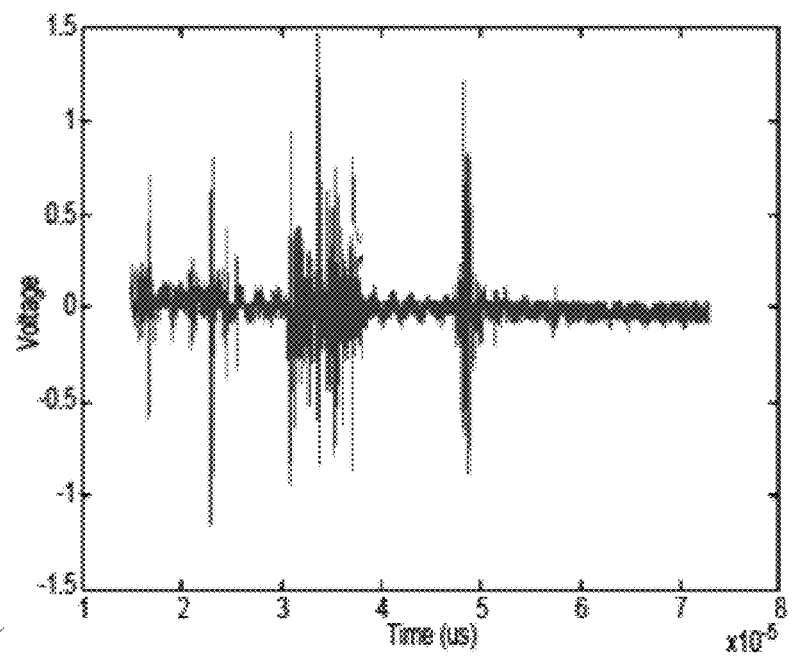
FIG. 18 is a scan of the target anatomy captured by one embodiment of the present disclosure.

FIG. 18 depicts an image 1800 of a single scan line through the nerve. There are characteristic signatures from the nerves that can be used to detect the nerve from a single scan line.

In another experiment, a dual element transducer 40, 42, having a configuration similar to the embodiment disclosed in FIG. 10, was utilized. This embodiment was used for testing of sciatic nerves of 22 rabbit legs post-mortem. A total of 142 sets of radio frequency (RF) data were collected. Each slice of data was recorded over a 30 mm lateral distance capturing an axial region of approximately 5-20 mm from the transducer surface. Imaging performance was evaluated when conducting a sector scan of −35° to 35° at a depth of up to 1.5 cm and a center frequency of up to 15 MHz. The ultrasonic transducer used for scanning was dual-element, 10 MHz transducer, where each element was 3 mm in diameter with an f-number of 3. Images were acquired using a Pulser/Receiver, the settings of which are shown in the table below.

TABLE 1

| Pulser/Receiver settings | |
|---|---|
| Pulse Repetition Frequency | 200 MHz |
| Energy | 12.5 uJ |
| Damping | 25 Ohms |
| High Pass Filter | 1 MHz |
| Low Pass Filter | 20 MHz |
| Input Attenuation | 0 dB |
| Output Attenuation | 0 dB |
| Gain | 20 dB |

Figure 41:
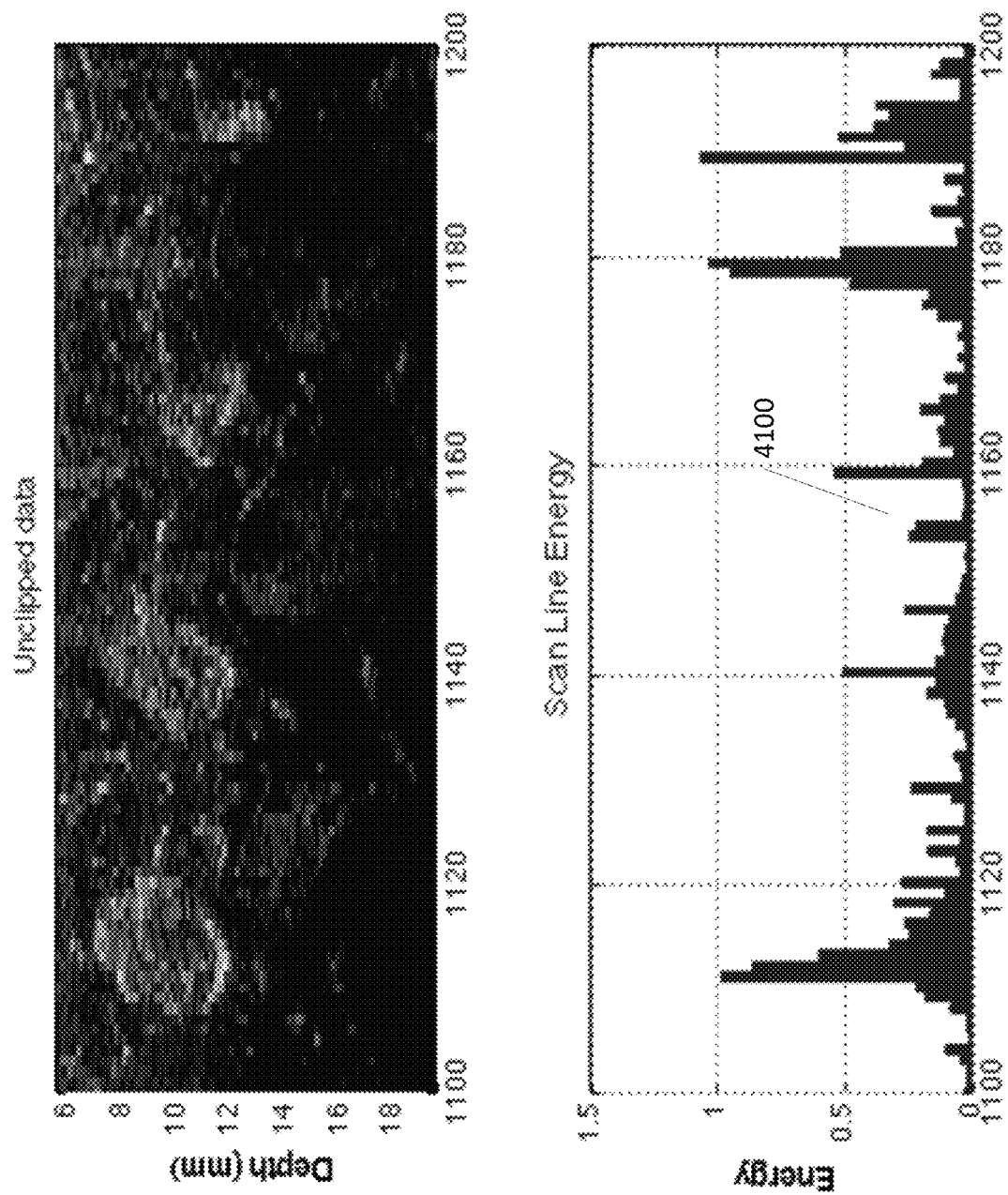
FIG. 41 depicts an illustrative graph of scan line energy as a nerve discriminant.

As discussed above, the device was used to capture an ultrasonic B-mode image, where the sciatic nerve may be identified as an isolated, hyperechoic region, usually elliptical or circular in nature as seen below. As such, one of the first attempts to classify the images was based on the thresholding on the energy of the received scan line. From the data displayed in FIG. 41, for example, it may be seen that the scan line energy does allow for the detection of the presence of the sciatic nerve. Using energy alone, however, as a classification criterion may not be adequate to distinguish between the diffuse, weak signature of the nerve with the sharp, strong signature of an isolated strong scatterer (e.g., data point 4100 in FIG. 41).

Figure 42:
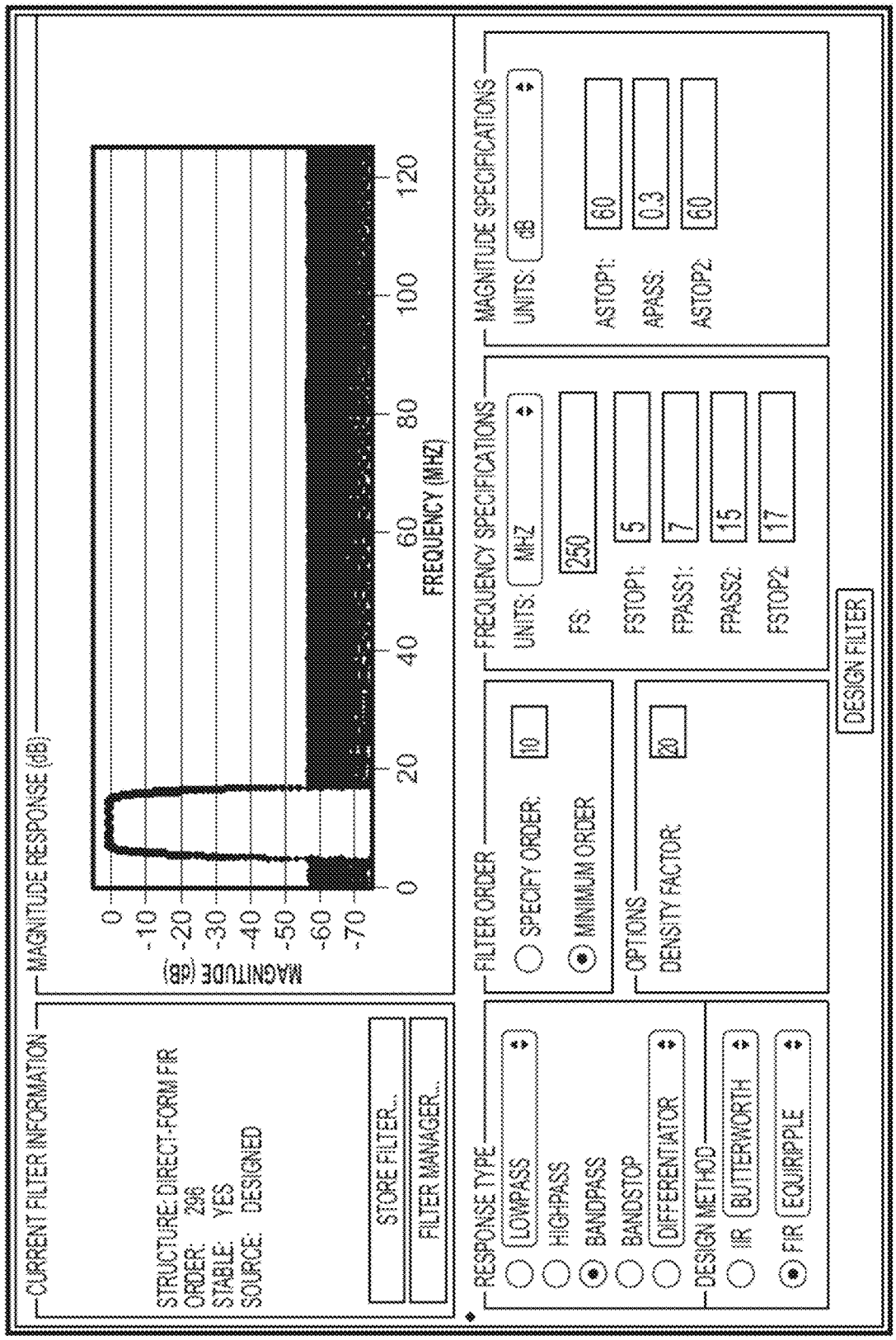
FIG. 42 depicts an illustrative user interface design window containing a designed bandpass filter and specifications.
Figure 43:
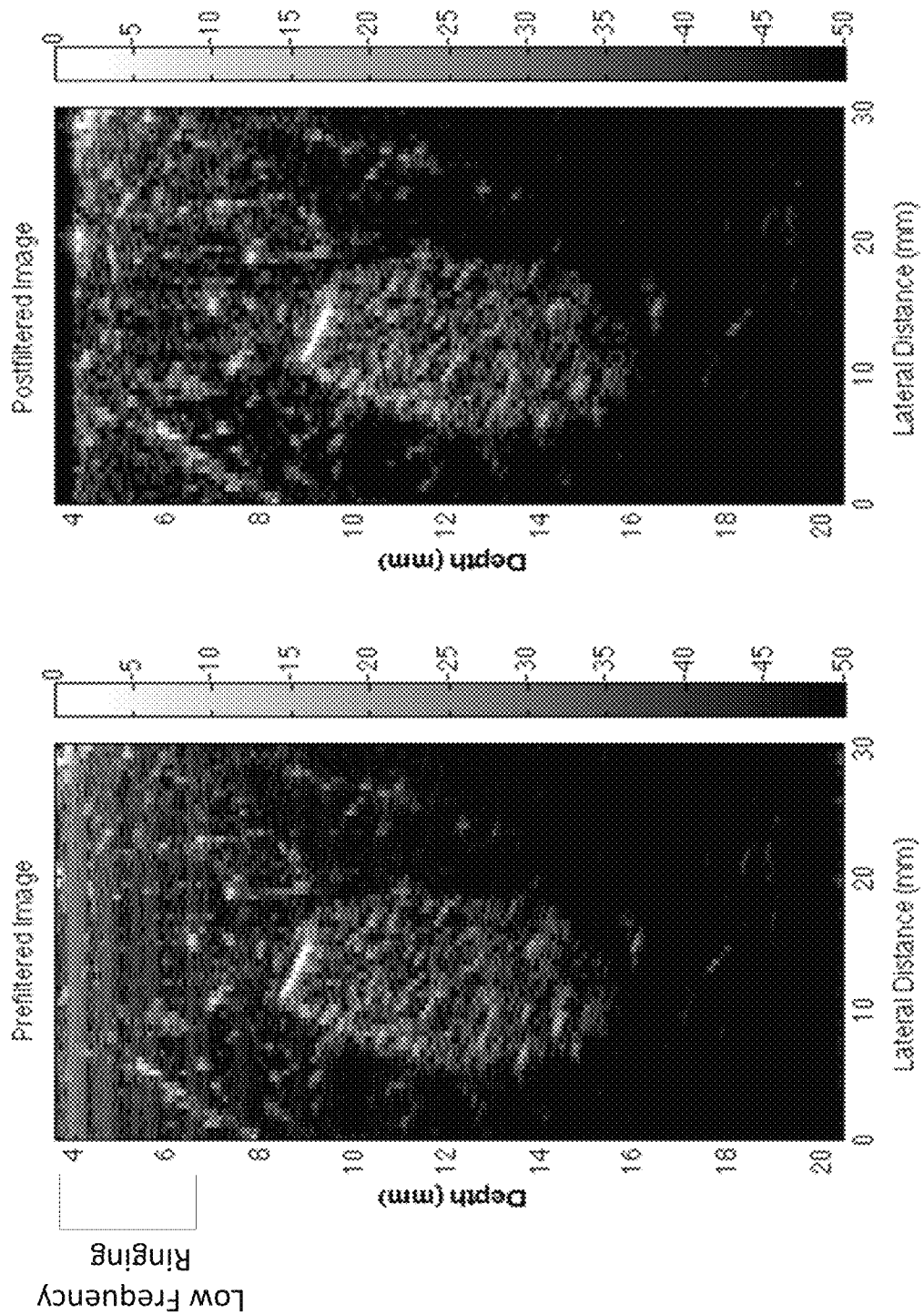
FIG. 43 depicts an illustrative application of a bandpass filter on the received RF signals, thereby suppressing low frequency noise near the transducer surface.

Low frequency ringing may also be present in the received RF scan lines, particularly near the surface of the transducer. Spectral analysis of the ringing may indicate a high noise component, such as a noise component between 500 kHz and 2 MHz. To combat this noise, the received RF may be passed through a finite impulse response (FIR) bandpass filter, such as software, hardware, and/or firmware configured using the design specifications described in Table 2 and illustrated in example user interface 4200 of FIG. 42. Furthermore, an illustrative output 4300 of the bandpass filter is shown in FIG. 43.

TABLE 2

Bandpass filter design specifications

| Type | Optimal Equiripple |
|---|---|
| Order | 296 (minimum order) |
| Sample Frequency | 250 MHz |
| Fstop1 | 5 MHz |
| Fpass1 | 7 MHz |
| Fpass2 | 15 MHz |
| Fstop2 | 17 MHz |
| Astop1 | 60 dB |
| Apass (ripple) | 0.3 dB |
| Astop2 | 60 dB |

Since classification of the nerve using only the scan line energy may not yield satisfactory results, it is appreciated that a multivariate classification approach can be explored. One commonly used multivariate classification algorithm is a support vector machine (SVM). A SVM may be a supervised learning algorithm that attempts to find an optimally separating hyperplane between two labeled sets of data. Each observation within the data sets consists of a number of features, which may be in some aspects descriptive variables that may be used to help classify the data.

For example, with reference to SVM classification schemes 4410 and 4420 in FIG. 44, consider the two-dimensional classification problem below. The $i^{th}$ observation in the training set is associated with a feature vector $x^{(i)}=(x_1^{(i)}, x_2^{(i)})$ and a data label $y^{(i)} \in \{-1, 1\}$ which describes the observation's class. Any hyperplane over the feature space may be defined as $\{x: f(x)=\beta^T x+\beta_0=0\}$, where $\beta$ is a vector. The general goal of the SVM is to solve the optimization problem $$\min_{\beta,\beta_0} \|\beta\|$$

subject to the constraint $y^{(i)}(\beta^T x^{(i)}+\beta_0) \geq 1$ for all i in the training set. By solving this optimization problem, the SVM may locate the hyperplane which maximizes the margin between separable data. Once the values for $\beta$ and $\beta_0$ are found, new events may then be classified based on which side of the hyperplane they lie, or equivalently:

$$\hat{y}(x)=\text{sign}(\beta^T x+\beta_0)$$

Figure 44:
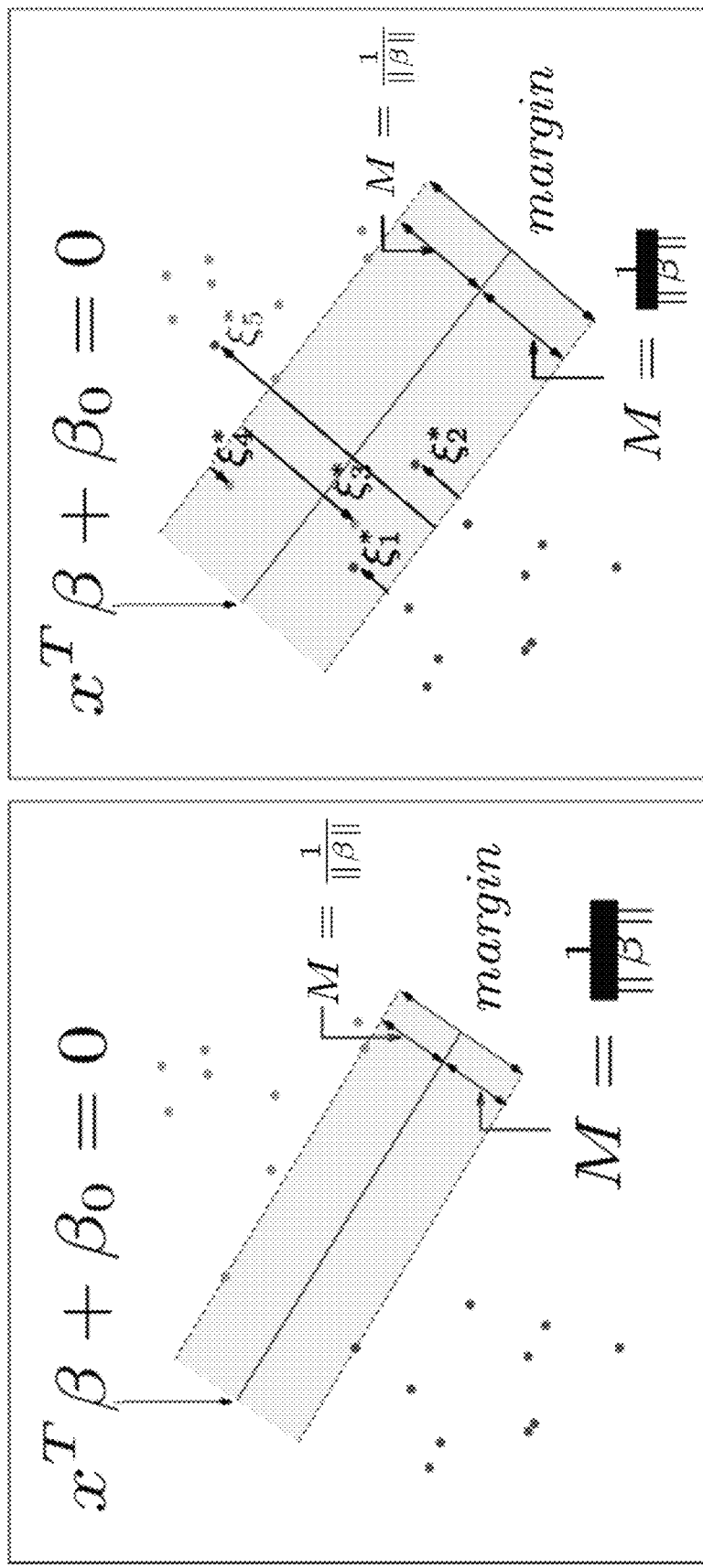
FIG. 44 depicts examples of SVM classification schemes for separable and non-separable data.

This simple form of SVM works for separable data, like the case in FIG. 44 on the left (e.g., scheme 4410). However, in many cases the data may not be separable, such as the case on the right (e.g., scheme 4420). In this case, the SVM must change the optimization problem to include slack variables, $\xi_i$, into the optimization problem. The new optimization problem is then given by $$\min_{\beta,\beta_0,\xi_i} \frac{1}{2}\|\beta\|^2 + C\sum_i \xi_i$$

such that $$y^{(i)}(\beta^T x^{(i)} + \beta_0) \geq 1 - \xi_i$$

By adding these slack variables, the constraint is now much less restrictive, since the slack variables allow for particular data points to be misclassified. The amount of misclassification may be controlled by the reweighting factor C known as the box constraint. In some aspects, the box constraint may be a parameter specified by the operator. When the box constraint is high, the optimization algorithm may force the slack variables to be small, thus resulting in a more restrictive classification algorithm.

Some classification problems do not automatically lend themselves to simple linear decision boundaries. In these cases, a feature set may be transformed into a different domain before attempting linear separation. For example, the instances of x may be replaced with the transformed version h(x). Typically these feature transformations are specified by their kernels. The kernel of the transformation is defined as the inner product between transformed feature vectors, or symbolically, $$K(x^{(i)},x^{(j)})=\langle h(x^{(i)}),h(x^{(j)})\rangle$$

A commonly used kernel may be the radial basis function or Gaussian kernel, which may have the form $$K(x^{(i)}, x^{(j)}) = \exp\left(-\frac{\|x^{(i)} - x^{(j)}\|^2}{2\sigma}\right)$$

In practice, Gaussian kernels are generally known to perform well in nonlinear classification. However, Gaussian kernels also add another degree of freedom to optimize over: the width parameter $\sigma$. This is yet another parameter which may have to be tuned by the operator depending on the target anatomy.

For each scan line, a set of features may be generated based on the statistical information of the received RF data and envelopes. In order to help mitigate corruption due to isolated strong scatterers, statistics based on the log of the envelope may also be computed. The identity and uniqueness of the classifier to the problem is the combination of the feature set used to build the classifier. A complete list of features is given below. It is appreciated that for a particular embodiment, any combination of these features may be used for the SVM to identify the target anatomy: (1) skewness of the received RF, (2) mean of the envelope, (3) variance of the envelope, (4) skewness of the envelope, (5) kurtosis of the envelope, (6) mean of the log of the envelope, (7) variance of the log of the envelope, (8) skewness of the log of the envelope, (9) kurtosis of the log of the envelope.

Figure 45A:
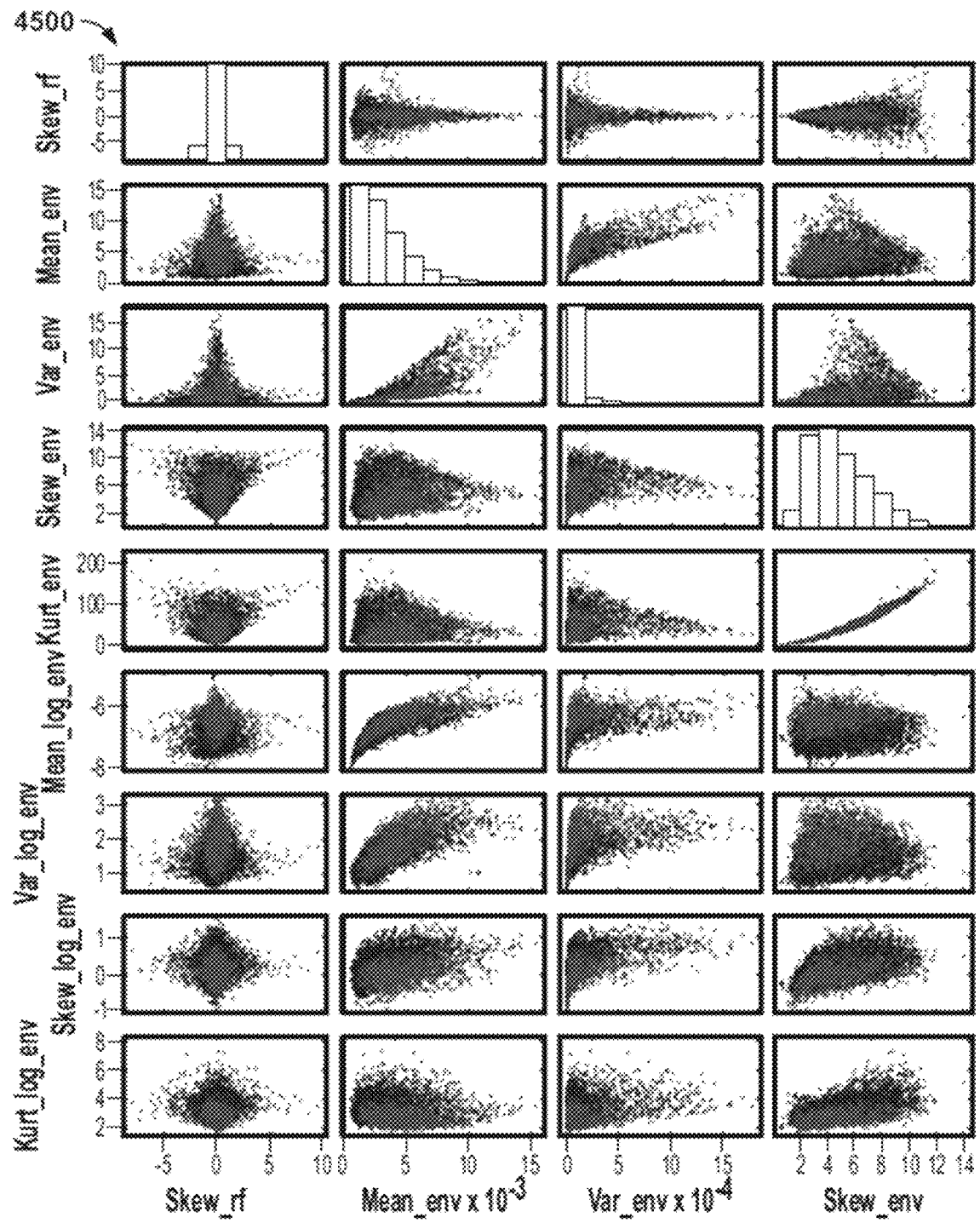
FIGS. 45A & B depict a plot matrix showing two-dimensional (2D) relationships between the feature variables.
Figure 45B:
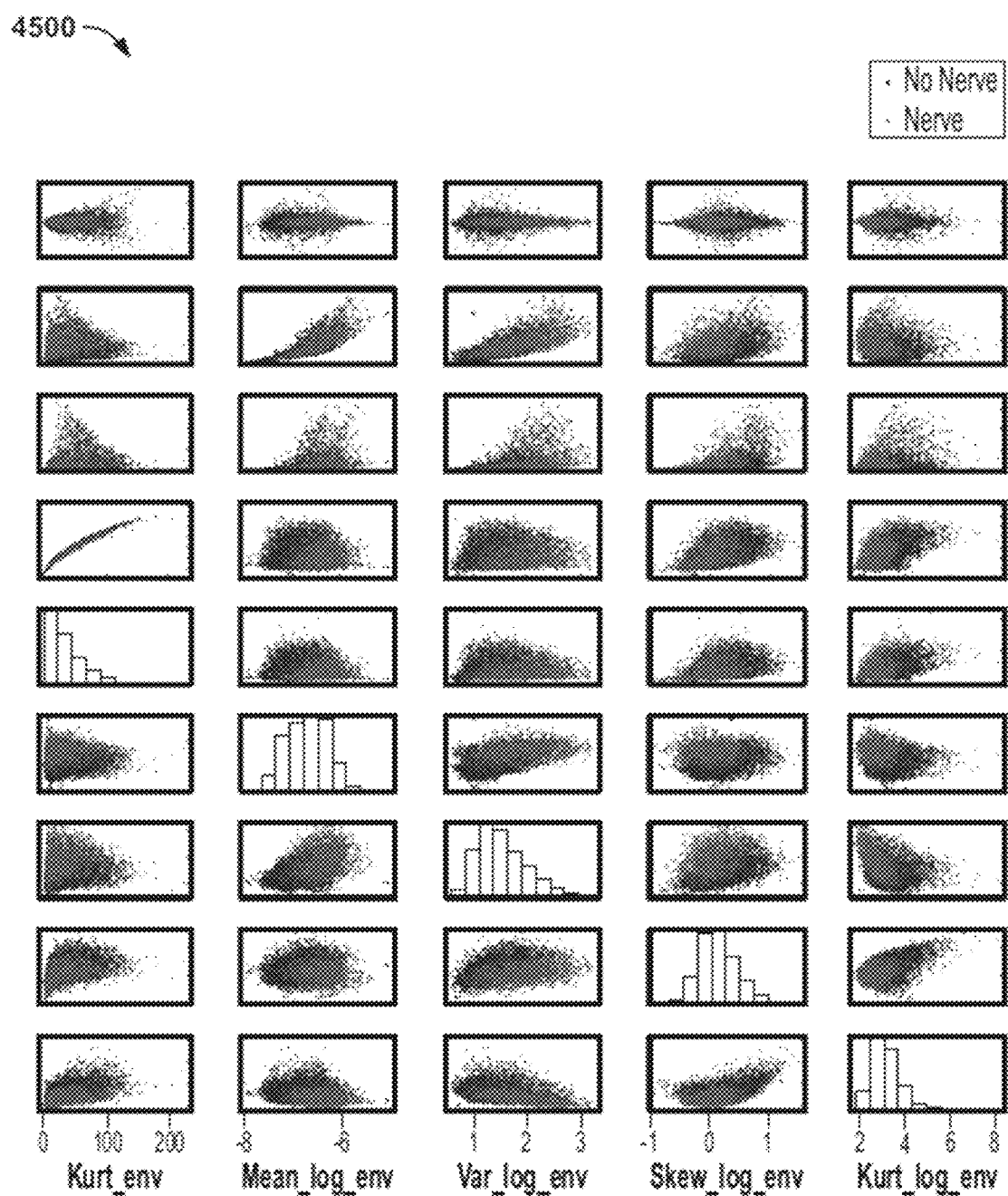

FIG. 45 illustrates a plot matrix 4500 demonstrating that the above-recited features do not appear to completely discriminate scan lines containing the nerve from scan lines that do not. Most of the data does not appear to follow a simple linear decision boundary, so a Gaussian kernel with $\sigma=1$ was used to help preserve nonlinear tendencies. The box constraint parameter was also set to 1 during training.

Figure 46:
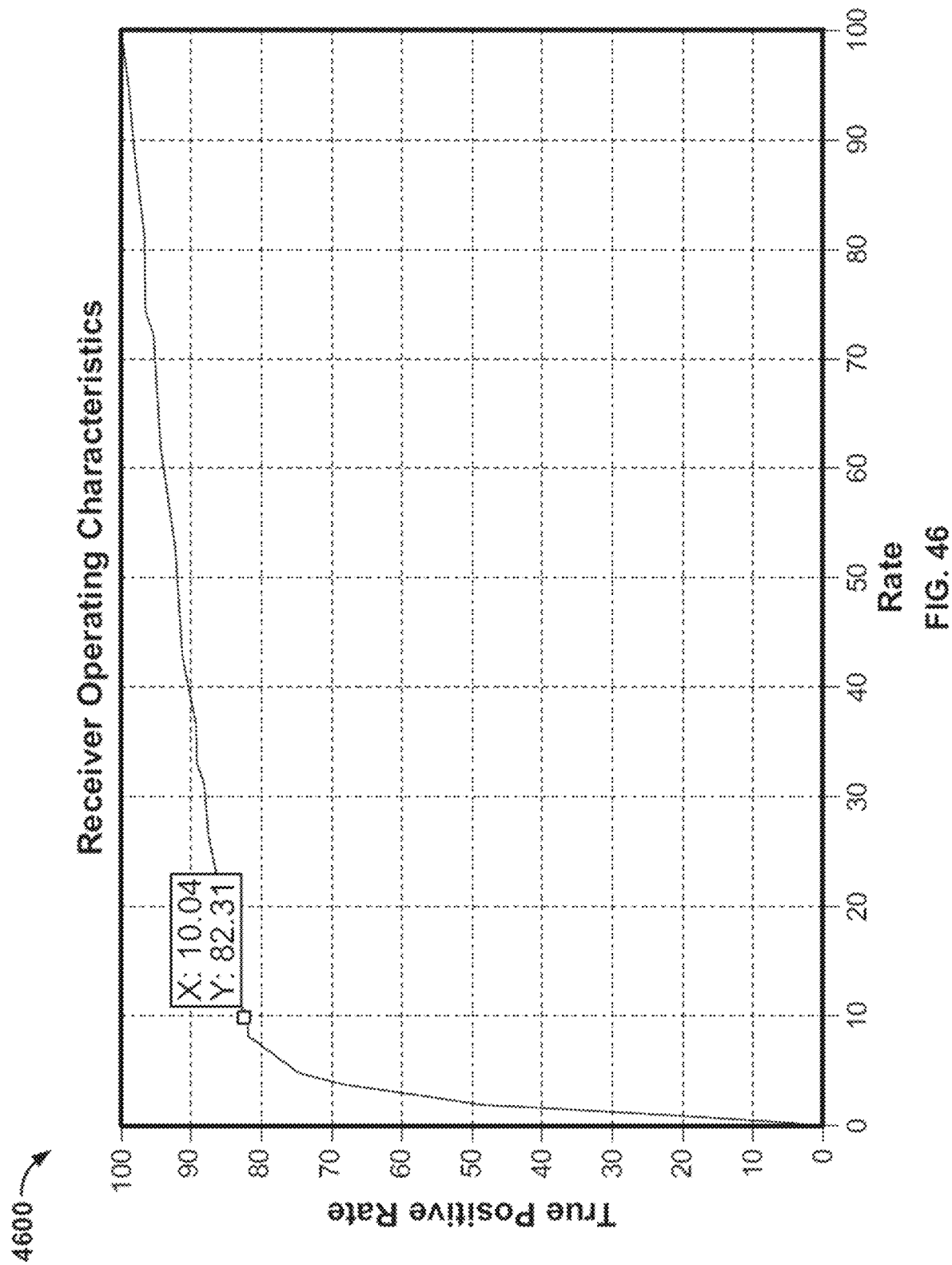
FIG. 46 depicts an illustrative receiver operating characteristic (ROC) curve defining performance of the trained SVM.

To evaluate the performance of the SVM, an evaluation metric may be computed by a specially-programmed computing device. In some aspects, the receiver operating characteristic may be used as an evaluation metric. For example, as a classification algorithm, the ROC curve plots the true positive rate vs. false positive rate, thus displaying the different trade-offs between operating at various threshold levels. FIG. 46 illustrates the results 4600 of the ROC plot, indicating that the classification algorithm appears to have good performance based on the training data distributions.

The testing demonstrated that a Gaussian-based SVM can be a powerful tool in determining the presence of the sciatic nerve in a single scan line. The majority of the power of any multivariate algorithm lies within the features used to describe the data. Utilizing just a single scan line, the system may be able to achieve a true positive rate of over 80% and a false negative rate of less than 10%.

Additional techniques contemplated include post-processing schemes, such as time gain compensation, to accentuate deeper features in the tissue, or using filters such as median filters to remove some of the strong peaks from the energy signals.

The detection of the nerve (or any other anatomical feature) may be automated. Once the anatomical feature is detected, an audio or visual signal such as "beeping" sound or a flashing light signal (or similar signal) may be given to a physician to indicate that they, or the device, are within a certain distance from the nerve.

Automatic detection of nerve may be based on single scan lines, and may compare the b-mode scan lines captured by the probe with the known scan lines of the target anatomy. In some aspects, the detection system may notify the operator that the captured scan lines are identical to, or are within a certain predetermined value of, the known scan lines of the target anatomy (e.g., the known scan lines of the target anatomy may represent a unique signature). The detection system may also be calibrated to determine the proximity of the tip of the probe to the target anatomy and notify the operator when the tip of the probe is within a set distance (e.g. 1 mm). Furthermore, the system may be configured to notify the operator of the spatial location of the target anatomy and/or inversely the spatial location of non-target anatomy.

Further Details Regarding Aspects of the Present Disclosure

Figure 29:
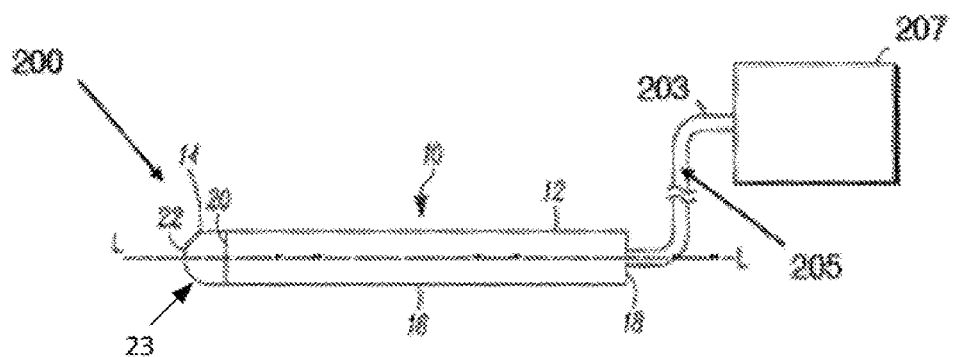
FIG. 29 is a side view of one embodiment of the present disclosure having direct visualization capability.
Figure 30:
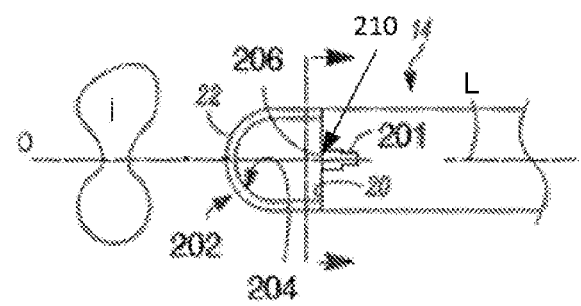
FIG. 30 is a cross-sectional view of the embodiment disclosed in FIG. 29.

In some aspects, the device 10 may be equipped with an image capture system 200 as shown in FIGS. 29 and 30 used to detect certain portions or aspects of the anatomy (e.g., nerve or vessels). The image capture system 200 may also be used independently of, or in conjunction with, the ultrasound imager 24, as described above in the device 10 embodiments, and/or may be used as a stand-alone or a complimentary detection technique to the ultrasound imager 24. In some aspects, the tip 22 in this embodiment may be a lens 23 that has an outer surface 202 and an inner surface 204. It is appreciated that the outer surface 202 of the lens 23 need not be the same shape of the inner surface 204 and may differ depending on the desired optical performance. The lens 23 may or may not provide a magnification of an image, I, beyond the lens 23. In this embodiment, the lens 23 provides no magnification. The lens 23 in this embodiment is clear, but can also be tinted or provided with a color filter as will be discussed below and may have anti-fog, anti-condensation, and/or anti-reflection coatings or properties.

As further seen in FIG. 30, the distal portion 14 of the device 10 further includes the image capture system 200 having an image capture device 201. The image capture device 201 may include an image capture sensor 206 that is disposed adjacent to the distal end 20 of the main body 16. The image capture device 201 can be connected to a flexible sheath 203 that may carry a fiber optic cable 205 that connects the image capture device 201 to a housing 207 that houses the image processing components. It is also contemplated that the image capture device 201 can be wirelessly coupled to the image processing components.

An image capture output device may be included that is in communication with an image control system that can adjust the properties of the image quality. It can also be appreciated that the image capture device 201 may wirelessly transmit images and video to the image control system without any hard wired components. The term "image capture device" may include devices configured to record or capture either still or video images, such as video cameras, digital cameras, CCD sensors, and the like. One example of an image capture device that may be used with the device may be a $\frac{1}{18}$" CMOS camera with OMNIVISION sensor OV 6930. However, those skilled in the art will easily contemplate the settings & components such as the "image capture device," illumination device, and the like in accordance with the present disclosure as described herein.

In one aspect, the image sensor 206 of the image capture device 201 may be disposed within the distal portion 14 of the main body 16. The image sensor 206 or the capture device 201 may be at the most distal end 20 of the main body 16 such that it forms a distal surface 210 of the image sensor 206 (or capture device 201) or is flush with the distal end 20 of the main body 16. In some aspects, "image sensor" may be synonymous with "image capture device." In some aspects, the image sensor 206 may be set back proximally from the distal end 20 of the main body 16, depending on the application. For example, the image sensor 206 may be recessed from the distal end 20 of the main body 16. Alternatively, the image sensor 206 or the image capture device 201 may extend from the distal end 20 of the main body 16 towards the inner surface 204 of the tip 22.

The image capture device 201 may define an optical axis O. As shown in FIG. 30, the optical axis O is the axis collinear with the longitudinal axis L defined by the main body 16 as discussed above. However, the optical axis O may also be or offset from the longitudinal axis L. The image capture device 201 will have a field of view α, varying between 5 and 180° depending on the specific application.

The image capture device 201 may be configured to capture an image I that exists just beyond the outer surface 202 of the tip 22. Specifically, as better shown in FIGS. 31 and 32, the tip 22 may be configured to dissect the anatomy of a patient, designated here as element 212. As seen here, the tip 22 while dissecting the anatomy may create a working space 214 by way of its shape. This may enable the image capture device 201 to view the anatomy during the dissection process instead of having the anatomy directly abut the image capture device 201 which may distort the image quality.

In this embodiment, the working space 214 may be defined as the space between the distal surface 210 of the image capture device 201 and the outer surface 202 of the tip 22. The working space 214 may permit the image capture device 201 to view a portion of the anatomy that is within its viewing angle α. Without the working space 214, the anatomy might abut and thereby obstruct the image capture device 201 thereby preventing an illumination device 216 from illuminating the anatomy and the image capture device 201 from capturing an image. The working space 214 in some aspects may be primarily filled with air, but it can be appreciated that the working space may be filled with other materials, such as a liquid or other gases. In the alternative, the working space 214 may be created by a tip that is solid such that the inner surface 204 of the tip 22 is adjacent to the distal end 20 of the main body. It can be appreciated that the working space 214 may create a distance between the outer surface 202 of the tip 22 and the image capture device 201 of 2 mm to 10 mm or greater.

Figure 33:
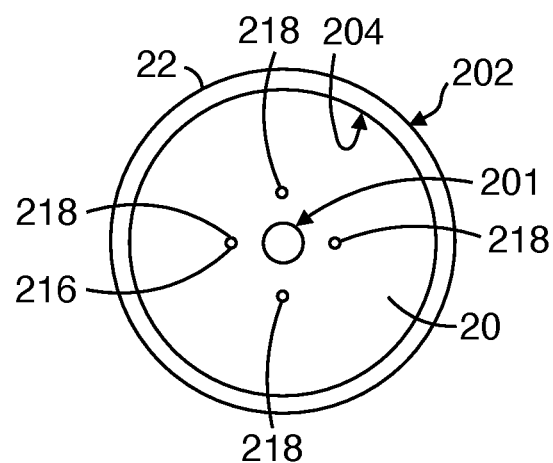
FIG. 33 is a partial front cross-sectional view of the embodiment disclosed in 29.

The distal portion 14 of the main body 16 may also include the illumination device 216, as shown in FIG. 33, which is a cross sectional view of FIG. 30. The illumination device 216 may include a set of light emitting diodes 218 ("LED"). It can be appreciated that the number of LEDs 218 and the location of each LED 218 with respect to the image capture device 201 may vary. For the example, there may only be one LED 218 for a particular application. Conversely, there may be as many as four or more LEDs 218. In some aspects, the LEDs 218 are spaced equidistant from one other, but it is not a requirement and the LEDs 218 may not be equally spaced. Other illumination devices 216 may include a light source such as near-infrared LED, mid-infrared LED, other LEDs of various wavelengths ranging from UV to infrared, or any similar light source known in the art. The illumination device 216 may also take the form of a light source emitting from an annular ring around the image capture device 201 or a plurality of light fibers angularly spaced around the image capture device 201.

Figure 34:
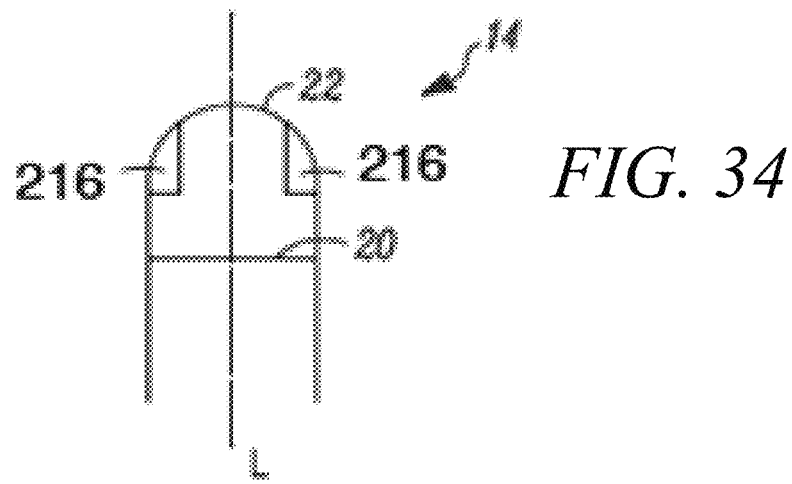
FIG. 34 is another embodiment of the present disclosure disclosed in FIG. 29.

The illumination device 216 in the device 10 may be disposed within the distal end 20 of the main body 16. However, the illumination device 216 may be external to distal end 20 or tip 22 or be embedded in the tip 22 such that the illumination device 216 does not create reflection on the inner surface 204 of the tip 22, as a reflection may impair the field of visibility of the image capture device 201. For example, and without limitation, the illumination device 216 may be disposed on either side of the longitudinal axis L of the main body 16 as shown in FIG. 34 and distal from the distal end 20 of the main body 16.

Regardless of the type of illumination device 216, the intensity of the illumination device 216 may be adjusted to as to change the level of illumination of the anatomy of a patient. Moreover, if the illumination device 216 includes more than one illumination sources, certain of the illumination sources may be turned off while others remain on, and that the intensity of each source may be independently adjusted.

The illumination device 216 may also include color filters to as to highlight certain features of the patient's anatomy such as a nerve or vessel, through a filter. In some aspects where the illumination device 216 consists of one or more LEDs 218, different color LEDs, such as red blue, yellow, green or others, may be used to enhance or highlight certain features of a patient's anatomy. One alternative to placing the filters with the illumination device 216 may be to include the filters with image capture device 201. The filters may include color filters, including red, orange, yellow, green, magenta, blue, violet, and the like. The filters may also include band pass-filters, such as UV, IR, or UV-IR filters to better view the desired anatomy. Alternatively, or in conjunction with the above, the illumination device 216 may rely on ultraviolet to detect certain features of the patient's anatomy, such as a nerve. In this embodiment, the illumination device 216 may include a light source irradiating the desired portion of a patient's anatomy with illumination light including excitation light of a wavelength band in an ultraviolet or visible region. It is also contemplated that the illumination device 216 may have both illumination means for emitting illumination light in the visible and ultraviolet regions simultaneously and where the image capture device having an appropriate spectral response can capture images in both regions.

Figure 35:
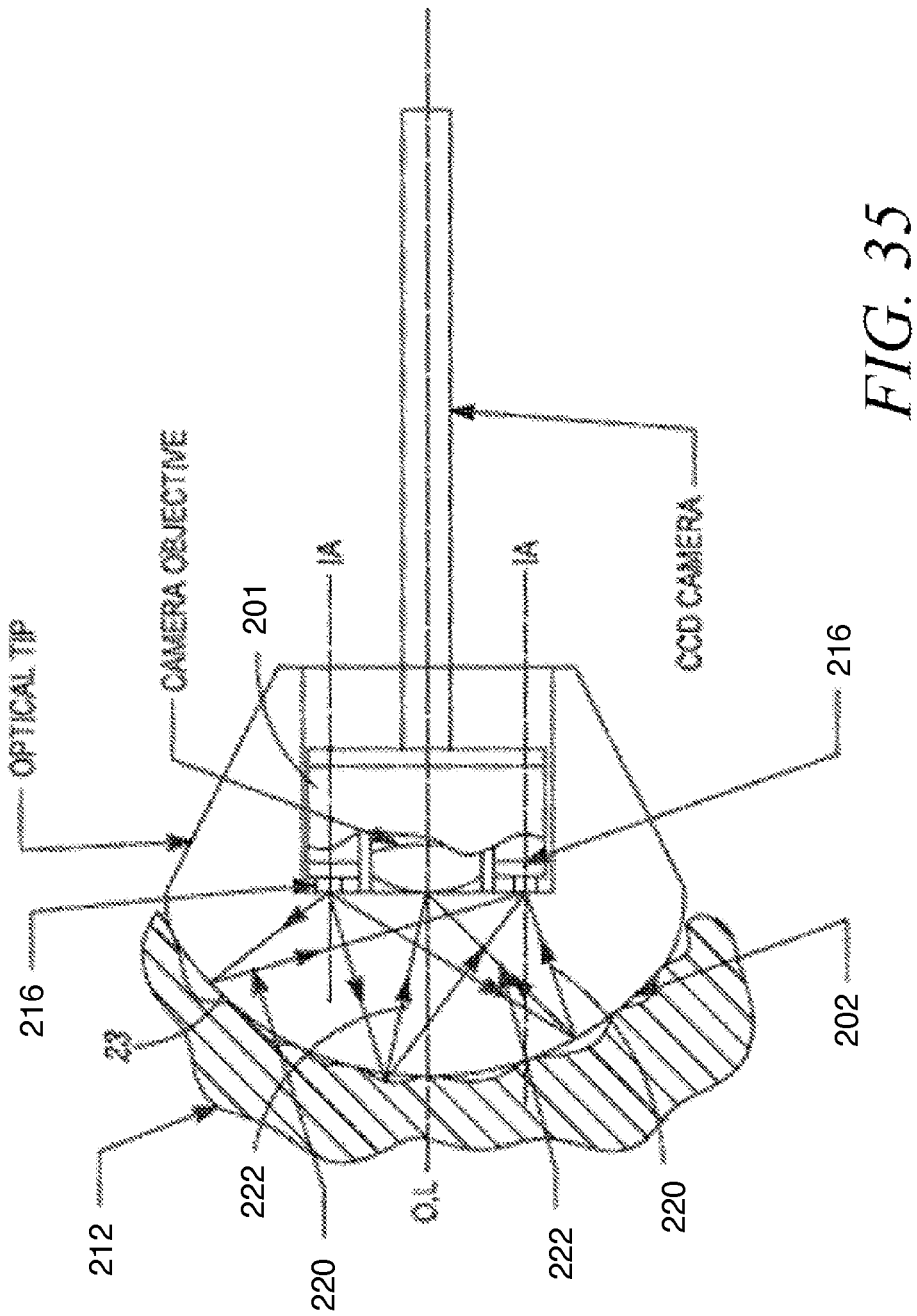
FIG. 35 is a side cross sectional view of another embodiment of the present disclosure disclosed in FIG. 31.

The illumination device 216 may have an illumination axis IA as disclosed in FIG. 35. The illumination axis IA may or may not be collinear with the optical axis O or the longitudinal axis L of the device. The illumination device 216 and location of the illumination axis IA may result in a reflection captured by the image capture device 201 that may distort the image of the patient's anatomy. The reflection may be caused by the rays generated by the illumination device 216 reflecting from an outer surface 202 or inner surface 204 of the tip 22 or the lens 23. To minimize and/or eliminate the reflection caused by the illumination device 216, the illumination axis IA may be displaced relative to the optical axis O of the image capture device 201. In the aspect as shown in FIG. 35, the optical tip is shown as a solid lens with the elliptical outside surface 202. One property of elliptical surfaces is that if a light source is placed at one focus, all light rays on the surface of the ellipse are reflected to the second focus. Each of two light sources 216, in the form of LED or optical fiber, may be placed at the focal point of elliptical surface 202. The illumination rays 220 reflected from elliptical surface may concentrate at foci of this surface while the rays 222 reflected from the tissue abutting the surface 202 may be directed toward the image capture device 201. This arrangement eliminates the direct optical reflection of illumination beams into the image capture device 201 or sensor 206 while maintaining its on-axis position. The offset between the optical axis O and the illumination axis IA may vary in range including between 1 to 2.5 mm.

Figure 31:
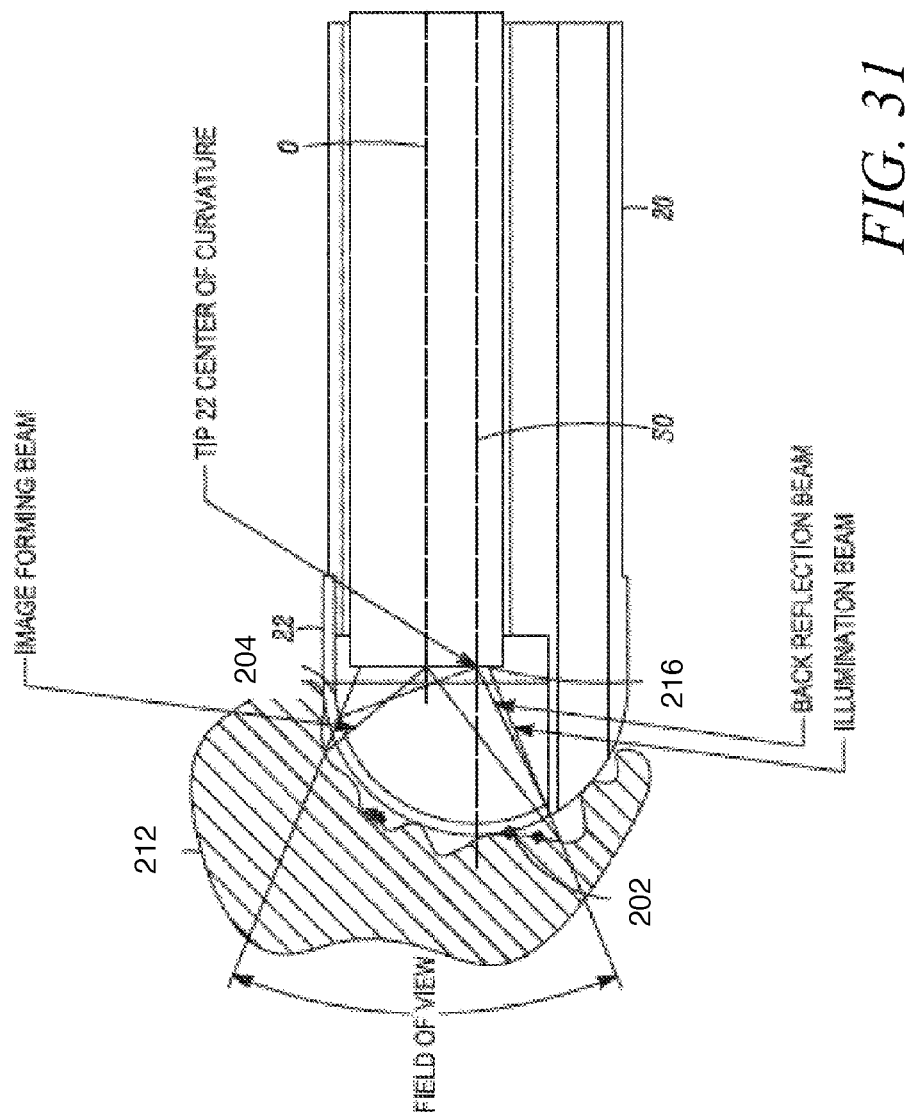
FIG. 31 is another embodiment of the present disclosure having direct visualization capability.
Figure 32:
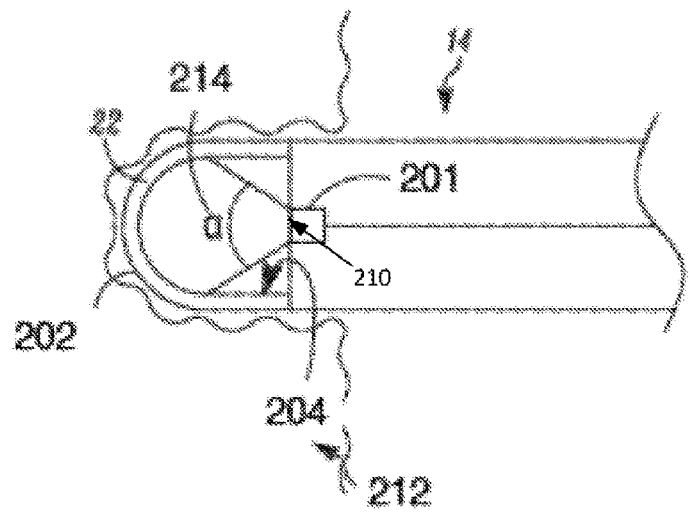
FIG. 32 is a partial cross-sectional view of the embodiment disclosed in FIG. 31.

Another embodiment of the device that includes an offset between the optical axis O and illumination axis IA is shown in FIG. 31. As shown in this embodiment, the tip optical axis SO of the tip 22 is offset from the optical axis O of the image capture device 201 to reduce or minimize the amount of reflection captured by the image capture device 201. In this embodiment, the illumination may be provided by an annular ring of optical fiber around the lens of the image capture device 201. The illumination beams reflected from the inner surface 204 will focus on the tip 22 center of curvature. Because the tip optical axis is offset in relation to the optical axis of the image capture device 201 its center of curvature is outside of the objective field of view and therefore reflected beams do not degrade the image quality.

Figure 36:
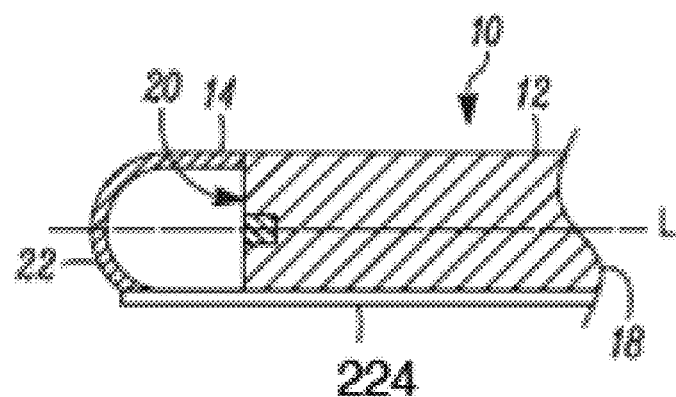
FIG. 36 is yet another embodiment of the conduit disclosed in FIG. 29.
Figure 37:
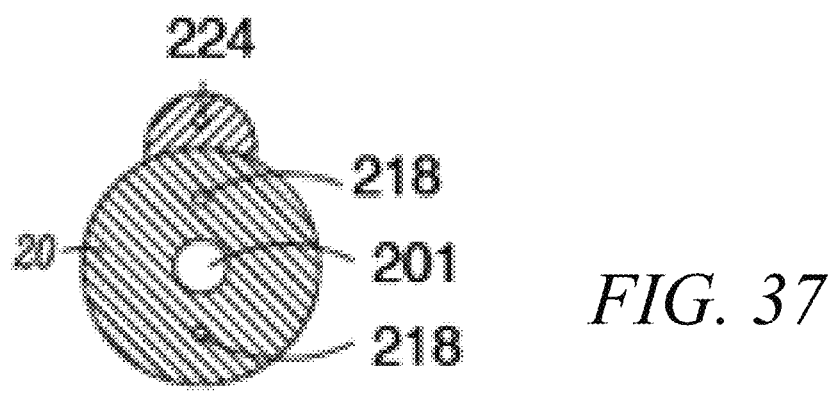
FIG. 37 is yet another embodiment of the conduit disclosed in FIG. 29.

As shown in FIGS. 36-37, the device 10 may also include a conduit 224 disposed at least partially within the main body 16 and the tip 22. In the aspect shown in FIG. 36, the conduit 224 may be off-set from the longitudinal axis L of the main body 16. However, in some aspects, the conduit 224 may be collinear with the longitudinal axis L of the main body 16. The conduit 224 may extend from the proximal end 18 of the main body 16, or may be formed along only a portion of the main body 16 and extend all the way through the distal portion 14 of the device, including the tip 22. The conduit 224 may be used in the ultrasound or visualization embodiments of this device. The conduit 224 may also be placed in the along the longitudinal axis of the main body 16, which may require the transducer 26 to be offset to accommodate the conduit 224.

Stated differently, the location of the conduit 224 may vary and may be application dependent. For example, and without limitation, the conduit may be placed closer to the longitudinal axis L than shown in the embodiment disclosed in FIG. 36. In the alternative, the conduit may be placed on the exterior of main body 16 of the device to as to form a raised portion that extends along a direction that is substantially parallel to the longitudinal axis L of the main body 16. In this embodiment, the conduit 224 would reside in the raised portion as shown in FIG. 37, which is a cross-sectional view of the distal end 20 of the main body 16 of this embodiment.

In addition, it is contemplated that there may be more than one conduit 224 for a particular device 10 thereby allowing an operator to simultaneously place multiple instruments into the patient's anatomy. The diameter of the conduit is application dependent by can vary and may be between 0.3 mm to 5.5 mm.

A conduit 224 as shown in FIGS. 36-37, may be configured to receive a number of instruments, including a guide wire to guide the device 10 through the anatomy of a patient, a k-wire to anchor the device 10 to a surgical site such as the disk space between two vertebra, an illumination device, such as an optical fiber, to provide additional illumination to a particular region of the patient's anatomy, an ultrasound probe to image or detect particular regions of a patient's anatomy, such as the one described above, a fiber optic cord that emits visible or infrared light to image or detect particular regions of a patient's anatomy, a nerve stimulator for neuromonitoring, and the like.

Figure 48:
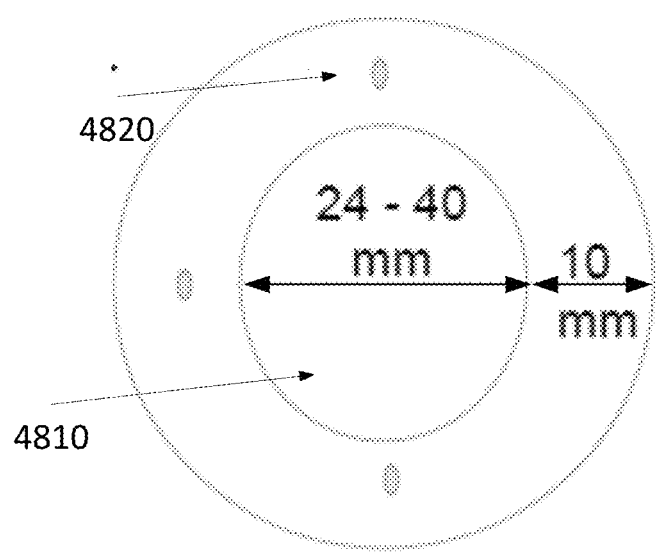
FIG. 48 shows the device viewed from the distal end as in an embodiment of the present disclosure.
Figure 49:
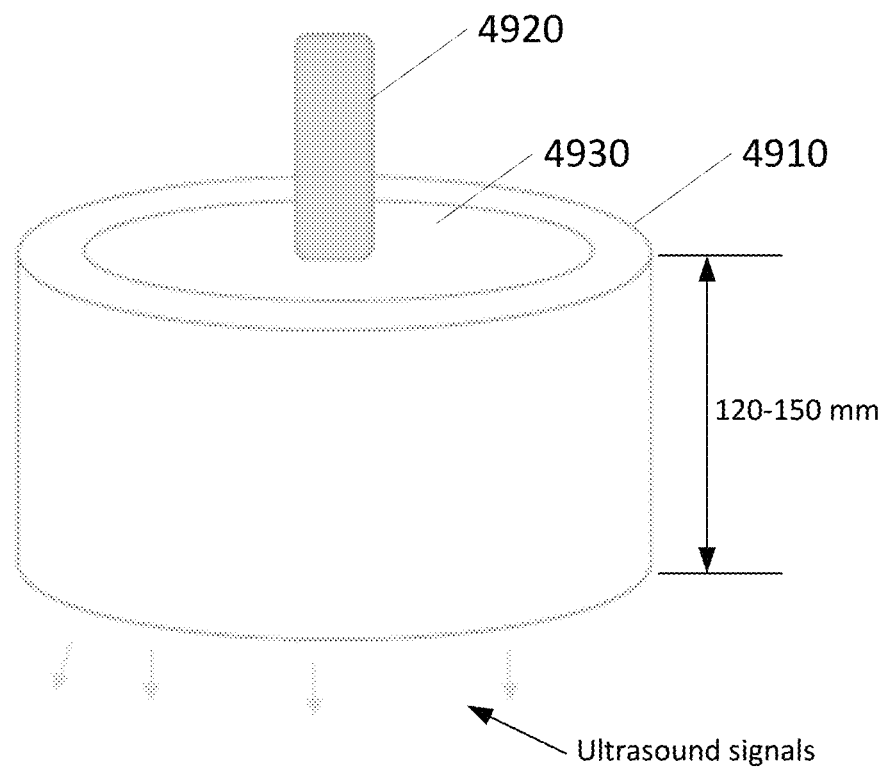
FIG. 49 shows the device viewed from the side as in an embodiment of the present disclosure.

In some embodiments, as shown in FIGS. 48 and 49, the device 10 may be provided with a channel 4810 (hollow region) extending throughout the length of the main body 16 and the tip 22. FIG. 48 shows the device 10, viewed from the distal end, to illustrate the tip 22 in these embodiments. As shown in FIG. 48, the tip 22 may form an annulus or ring. The inner space provided by the channel 4810 may provide a working channel inside the device 10 through which a surgeon may perform clinical procedures while allowing the device 10 to remain in place. This may allow for the collection and display of data for real-time feedback form the site of the surgery during the surgical procedure. In aspects of these embodiments, the main body 16 and the tip 22 may provide a channel 4810, with a diameter in a range from 24 mm to 40 mm. The wall of the main body 16 and/or tip 22 may be 10 mm in width. Various other diameters and widths are contemplated herein; the values discussed above are examples to aid in understanding of the disclosure. For example, in some embodiments, the diameter of device 10 may be selected to allow a particular surgical implement to be fitted through the channel of device 10 so that imaging may continue as the implement is advanced into tissue. In various aspects, the channel 4810 may be off-set from the longitudinal axis of the main body 16. However, in some aspects, the channel 4810 may be collinear with the longitudinal axis of the main body 16. The channel 4810 may extend from the proximal end 18 of the main body 16 all the way through the distal portion 14 of the device 10, including the tip 22.

In these embodiments, multiple transducers 26, such as transducer 4820 of FIG. 48, may be arranged on the distal end 20 of the device 10, on the ring-shaped tip 22. As discussed above, the transducers 26 may emit an ultrasonic frequency in a direction that is substantially parallel to the longitudinal axis of the device 10. It is also contemplated that various transducers may emit an ultrasonic frequency in a direction that is not parallel to the longitudinal axis of the device 10. It can be appreciated that the transducers 4820 may be orientated in any direction that is required for the particular application. The ultrasonic frequency may be between 1 and 10 MHz, depending on the application. The ultrasound imager 24 may collect information, such as acoustic property results, from the transducers and, using the classification algorithm, screen for target tissue, such as nerve tissue. Nerve tissue may be highlighted on a display. In some embodiments, a 2-D mapping or a 3-D visualization (e.g. volumetric image) of nerve tissue may be generated and displayed.

In some embodiments, as shown in FIG. 49, the device 10 may have a length of 120 mm to 150 mm, forming the shape of a tube 4910. It is contemplated that the device 10 may have a variety of other lengths, depending on the application. Probe 4920 is an example of a surgical tool that may be passed through the channel 4930 for various surgical procedures.

Figure 50:
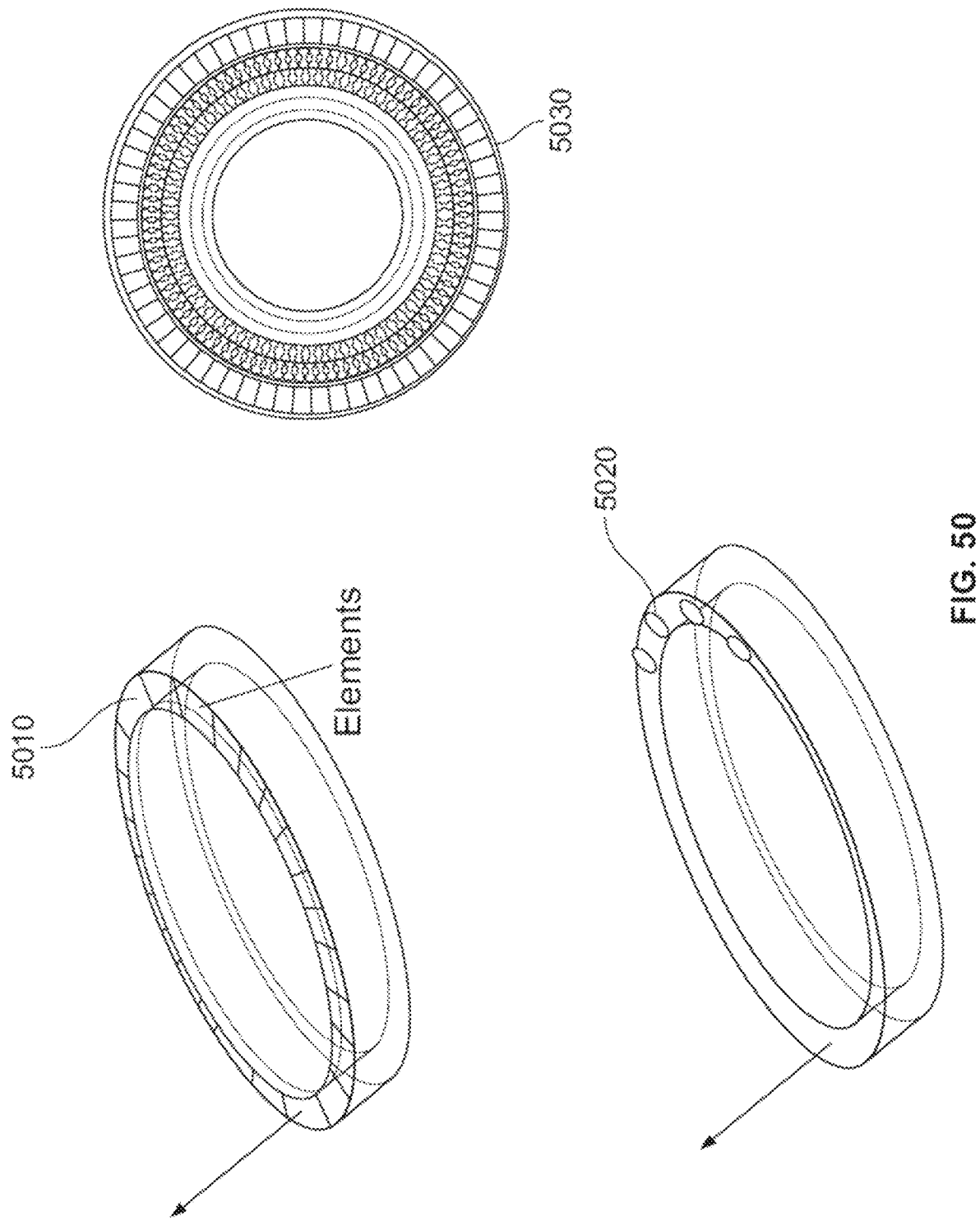
FIG. 50 shows the distal face of the device as in an embodiment of the present disclosure.

FIG. 50 shows the distal face of the tube, in order to illustrate various embodiments. The transducers are contemplated to have various shapes, such as a square, a rectangle, such as the rectangular transducers 5010, and circular, such as the circular transducers 5020. In some embodiments, more than one row of transducers may be arranged on the distal face, as illustrated in image 5030. Various quantities of transducers may be used, depending on the application. In some embodiments, 100 to 250 or more transducers may be position on the distal end of the tube. Transducer frequency may be in the range of 5 MHz to 20 MHz to cover the appropriate depth required for the application (for example, 0.1-5 cm in depth). Other transducer frequencies may be used in various embodiments.

Figure 51:
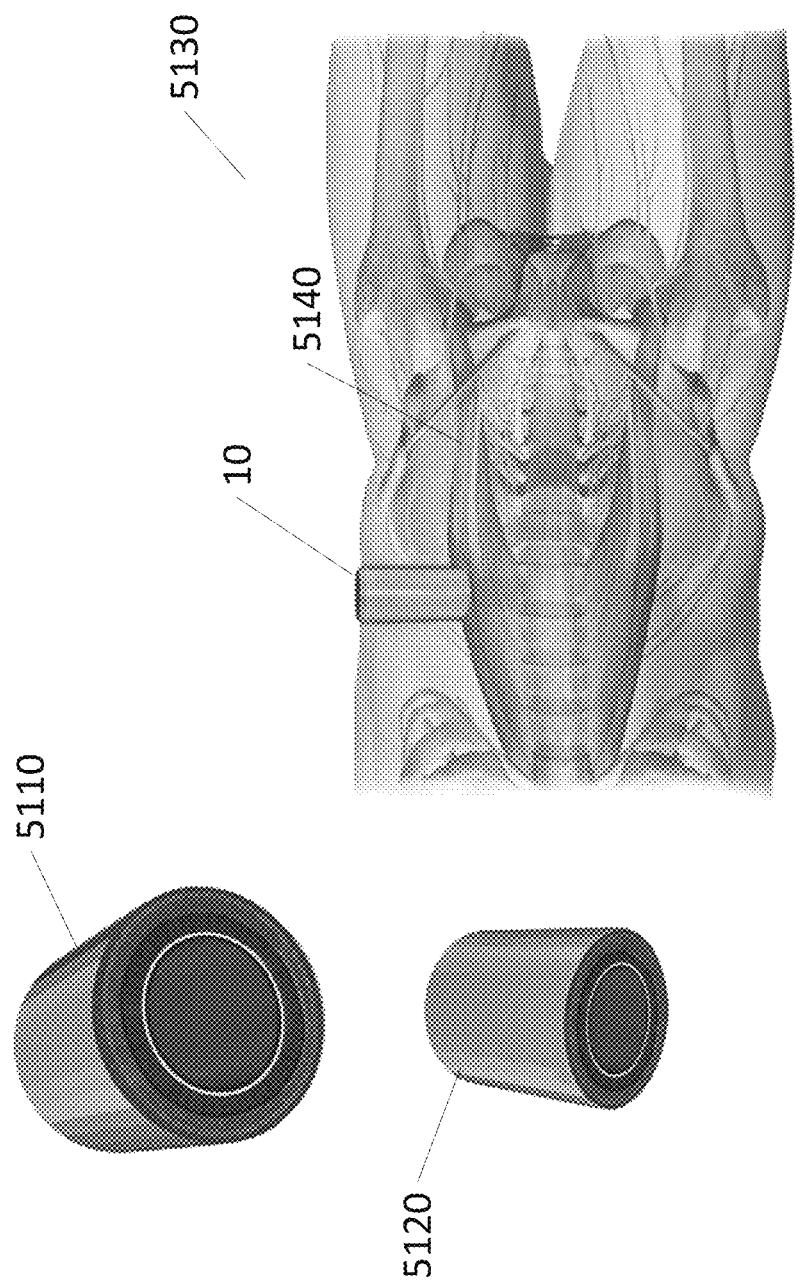
FIG. 51 depicts placement of the device on the surface of the psoas muscle as in an embodiment of the present disclosure.

The above embodiments may be further understood by referring to FIGS. 51-54. FIG. 51 shows the views 5110 and 5120 of device 10 having the channel as described above. Image 5130 shows the device 10 placed on the surface of the psoas muscle. The placement of the device 10 on the surface of the psoas muscle may be a first step prior to entering the psoas muscle in order to allow the surgeon to visualize the location of nerves within the psoas muscle using the methods as described herein. The transducers may emit ultrasound signals around the distal end of the device 10 and the image processor/software may form an image with a depth of 5-7 cm, creating a 3-D "volumetric" image of the area in the psoas muscle overlying the vertebral body and disc space. Based on use of the classification algorithm, sensory and motor nerves, and their routing, may be highlighted on the display.

Figure 52:
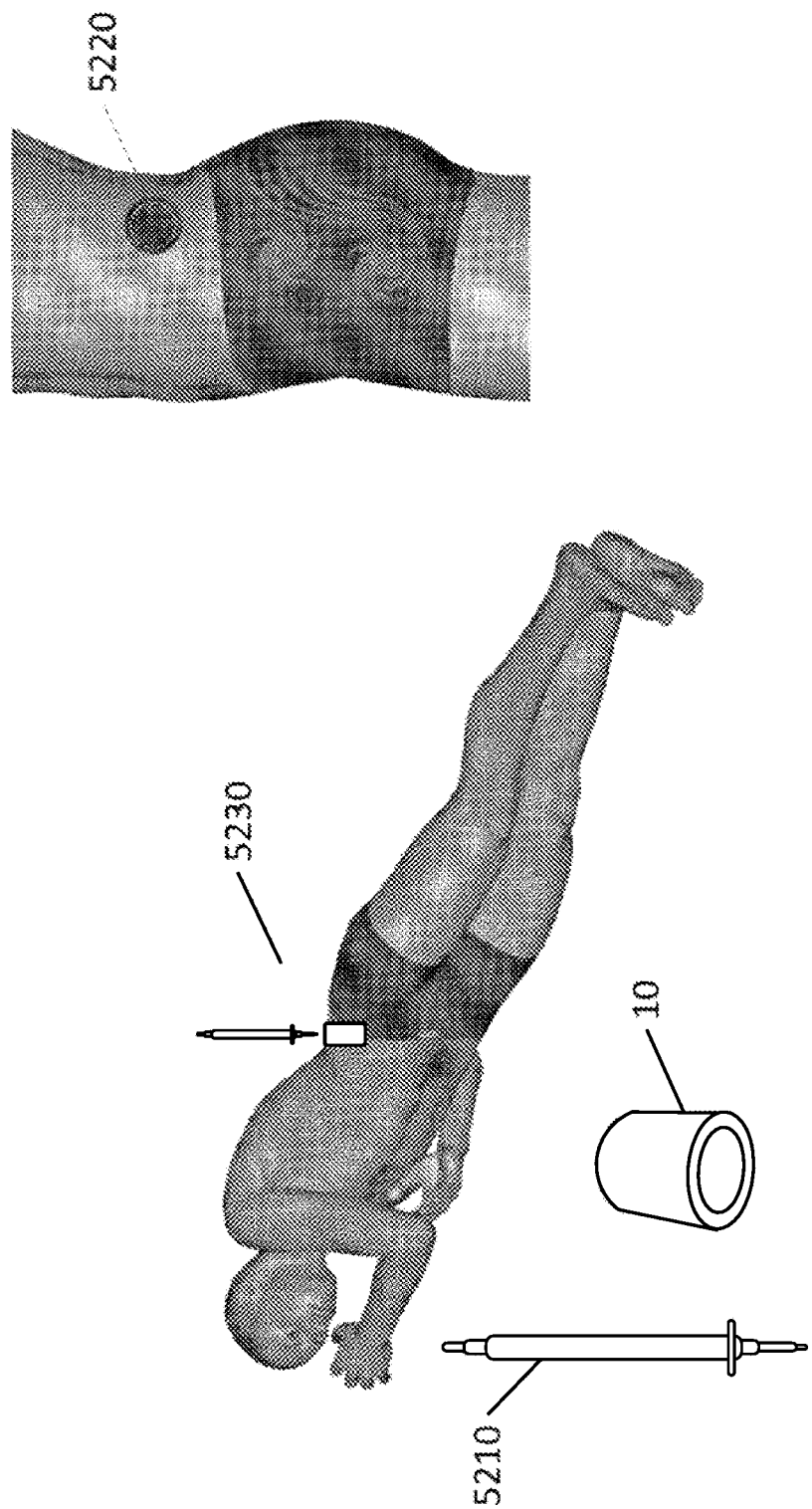
FIG. 52 is another depiction of the placement of the device on the surface of the psoas muscle as in an embodiment of the present disclosure.
Figure 53:
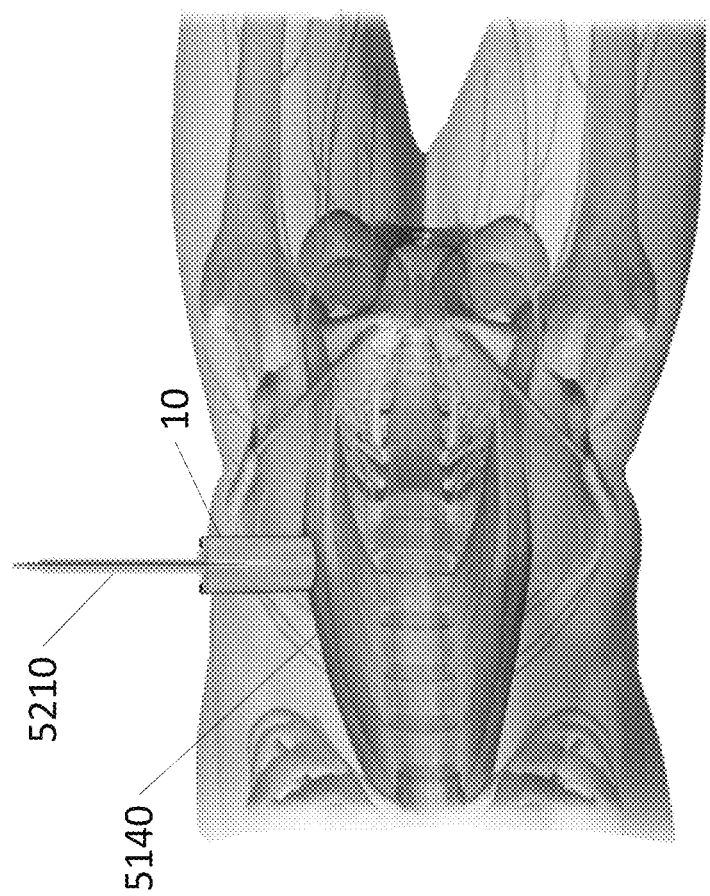
FIG. 53 depicts a probe inserted into the device on the surface of the psoas muscle as in an embodiment of the present disclosure.
Figure 54:
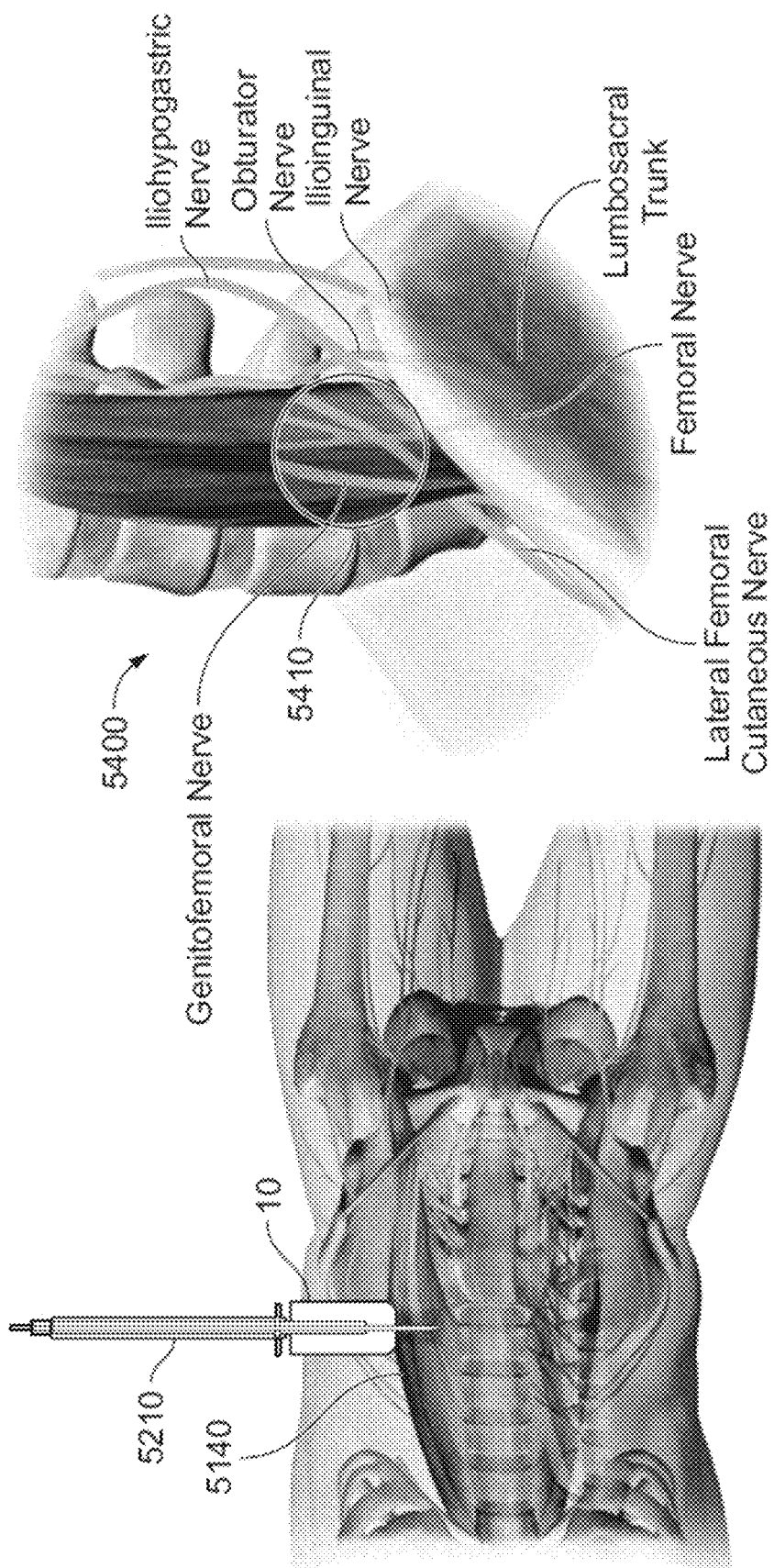
FIG. 54 depicts a nerve map in a viewing window in accordance with aspects of the present disclosure.

FIG. 52 shows the device 10 and a surgical probe 5210. Image 5220 shows the device 10 placed into position on the surface of the psoas muscle. Image 5230 depicts the probe 5210 before it is placed into the channel of device 10, which is in position on the psoas muscle. FIG. 53 depicts the device 10, placed against the psoas muscle 5140 and with the probe 5210 inserted (retracted) into the channel of device 10. At this point, the device 10 is in position for performing the operations as described herein to map the nerve tissues in the psoas muscle. FIG. 54 depicts the device 10, placed against the psoas muscle 5140 and with the probe 5210 inserted into the channel of device 10 and into the psoas muscle. Image 5400 shows an example anatomical image with a viewing window 5410 as may be generated by use of the classification algorithm. The viewing window 5410 may depict a map of the nerve tissues in the psoas muscle proximate to the device 10.

Figure 19:
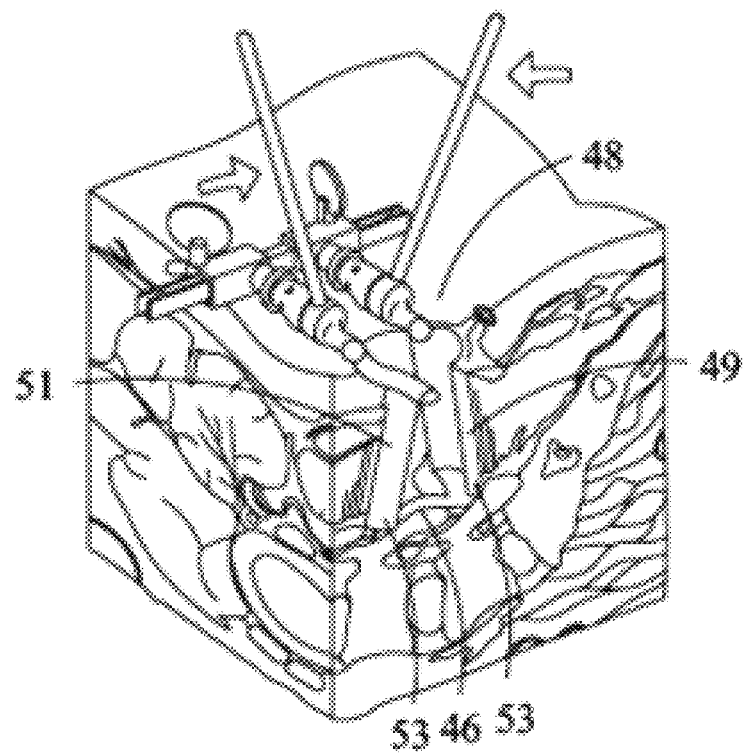
FIG. 19 depicts one embodiment of a retractor system that can be used with embodiments of the present disclosure.

Various aspects of the present disclosure are contemplated for being used in connection with minimally invasive surgery (MIS). The device 10 may be used for a variety of MIS procedures, including but not limited to, a lateral retroperitoneal interbody fusion (LLIF) (e.g., XLIF, DLIF), Axial Lumbar Interbody Fusion (AxiaLif), Transforaminal Lumbar Interbody Fusion (TLIF), Posterior Lumbar Interbody Fusion (PLIF), Anterior Lumbar Interbody Fusion, Transthoracic lumbar interbody fusion, Retropleural Thoracic Fusion, Interbody Fusion utilizing Kambin's Triangle, and Cervical/Thoracic/Lumbar Laminectomies, Foraminotomies and Diskectomies. The device 10 may be used to confirm that the area is clear of other anatomical parts, such as blood vessels, abdominal/pelvic viscera, nerve roots, and spinal cord. As shown in FIG. 19, once at the surgical site 46, the device 10 may be used to illuminate the surgical site 46, to allow a surgeon to introduce instruments (e.g. K-wire) to the surgical site via a conduit formed within the main body 16 of the device 10 or allow a retractor system or dilator system to create direct visualization and a working portal of the surgical site without the device 10.

As described above, there can be a number of applications for which this device 10 may be used, which require the similar steps to access the surgical site. The method of use described below is in connection with performing an LLIF, but it can be appreciated that the device 10 can be used in a similar fashion for performing other MIS procedures as mentioned above.

In operation, the ultrasound imager 24 is used to detect the patient's anatomy as described herein. A surgeon may rely on the image or audio queues generated by the ultrasound imager 24 to detect the presence (or absence) of a nerve thereby allowing the surgery to reposition (or continue advancing) the device 10 through the patient's anatomy towards the surgical site 46. The ultrasound imager 24 may also be used to confirm the image captured by an image capture device (not shown) is accurate by confirming the presence or absence of a targeted anatomical feature (e.g. nerve). The image capture device may consist of a camera or the like disposed within the distal portion 14 of the device 10 so as to capture an image of the region distal to the device 10.

The image capture system 200 may also be used in a similar fashion to visually detect the patient's anatomy. The image capture system 200 may be used to confirm what is detected by the ultrasound imager 24, or may be used independently to detect certain portions of the patient's anatomy.

The classifier/algorithm is integral in accurate nerve detection. In an alternative embodiment of the present invention, the classifier algorithm may be employed as follows:

An ultrasound probe acquires ultrasound backscatter data via a sector scan or similar ultrasound acquisition mode.

A 2D B-mode image may be constructed from the acquired data. A 2D B-mode image may be constructed using known methods and techniques. In one embodiment, a 2-dimensional image may be built up by firing a beam vertically, waiting for the return echoes, maintaining the information and then firing a new line from a neighboring transducer along a tambourine line in a sequence of B-mode lines. In a linear array of ultrasound crystals, the electronic phased array may shoot parallel beams in sequence, creating a field that is as wide as the probe length (footprint). A curvilinear array may have a curved surface, creating a field in the depth that is wider than the footprint of the probe, making it possible to create a smaller footprint for easier access through small windows. This may result in a wider field in depth, but at the cost of reduced lateral resolution as the scan lines diverge.

The image may be thresholded such that image intensity values above the threshold may be given a value of '1' and image intensity values less than the threshold may be given a value of '0'. This may result in a binary map of intensity values.

The binary image may then be filtered with a smoothing filter which may consist of a simple median filter or similar smoothing filter. It is contemplated that a variety of digital filters may be employed to process the binary image.

The numbers of pixels for contiguous regions in the binary image may be counted.

Contiguous regions in the binary image that have a pixel count above a minimum threshold and below a maximum threshold may be selected. This may correspond to areas of contiguous regions in the binary image. The thresholds may be selected so that a nerve in the image will be detected and selected with a high degree of accuracy.

If the selected contiguous regions are less than a specified distance from the probe (2 cm, for example), the contiguous region may be selected as a possible nerve. It should be understood that the measured distance may be within a range of distances, and that the specific distance of 2 cm is provided by way of example.

A shape factor may next be implemented by fitting an ellipse to outline the selected contiguous regions in the 2D binary image. The area of the contiguous region may be compared to the area of the ellipse outlining the contiguous region. If the ratio of the areas is below a certain threshold, the contiguous region may be classified as not a nerve. A variety of outlining techniques, aside from the fitting of an ellipse, may be used to compare the contiguous region.

If the contiguous region is classified as a nerve, the original image data corresponding to the contiguous region may next be processed for texture features. Specifically, for the selected contiguous region, the SNR, kurtosis and skewness may be calculated from the B-mode image data (it is understood that alternative data parameters may be measured at this time as well). Threshold values for each of these parameters may be established in order to detect the nerves in the image. If the combination of the SNR, skewness and kurtosis are below a threshold, the contiguous region will be classified as not a nerve. It is contemplated that additional data parameters may be measured from the original image data for nerve detection.

In an alternative embodiment, robust detection using double threshold and connected component tracking by hysteresis may be employed. Specifically, instead of using only one, it may be preferred to use two threshold values: a high threshold value and a low threshold value. For each pixel in the B-mode image, if its value is larger than the high threshold value, then it may be marked as a strong nerve pixel. If the pixel value is smaller than the high threshold value and larger than the low threshold value, then it may be marked as weak nerve pixel. If the pixel value is smaller than the low threshold value, then it may be discarded. The connected component algorithm may be applied to look at each weak nerve pixel, and if it is connected to a strong nerve pixel then the weak nerve pixel may be preserved.

In some embodiments, the shape of the identified connected components (blobs) of detected nerve pixels may then be analyzed. If the size and shape of a blob is significantly different from the profile of a nerve area (elongated or elliptical of width about 5 mm) then it may also discarded. The detected nerve region in a B-mode image should have, at most, a maximum dimension of 1 or 2 cm. It is understood that data may fall in ranges which may yield the detection of a nerve, and that specific numbers are only provided by way of example.

The distance from the detected nerve region to the ultrasound probe may be estimated and used in the display.

In an alternative embodiment of the present invention, it is contemplated that sophisticated training and detection algorithms for nerve region like support vector machine (SVM) or random forest may be utilized for improved nerve detection. In machine learning, support vector machines (also support vector networks) may be supervised learning models with associated learning algorithms that analyze data and recognize patterns, used for classification and regression analysis. Given a set of training examples, each marked as belonging to one of two categories, an SVM training algorithm may build a model that assigns new examples into one category or the other, making it a non-probabilistic binary linear classifier. An SVM model is a representation of the examples as points in space, mapped so that the examples of the separate categories are divided by a clear gap that is as wide as possible. New examples may then be mapped into that same space and predicted to belong to a category based on which side of the gap they fall on. In addition to performing linear classification, SVMs can efficiently perform a non-linear classification using what is called the kernel trick, implicitly mapping their inputs into high-dimensional feature spaces. Random forests are an ensemble learning method for classification, regression and other tasks, that operate by constructing a multitude of decision trees at training time and outputting the class that is the mode of the classes (classification) or mean prediction (regression) of the individual trees. Random forests correct for decision trees' habit of overfitting to their training set. Decision trees are a popular method for various machine learning tasks. Tree learning comes closest to meeting the requirements for serving as an off-the-shelf procedure for data mining because it is invariant under scaling and various other transformations of feature values, is robust to inclusion of irrelevant features, and produces inspectable models. However, they are seldom accurate. In particular, trees that are grown very deep tend to learn highly irregular patterns: they over fit their training sets, because they have low bias, but very high variance. Random forests are a way of averaging multiple deep decision trees, trained on different parts of the same training set, with the goal of reducing the variance. This comes at the expense of a small increase in the bias and some loss of interpretability, but generally greatly boosts the performance of the final model.

In another embodiment, to reduce the rate of false positives, the system will analyze the radio frequency (RF) data collected by the system. Specifically, once the region of interest is detected using the B-mode image analysis, the corresponding RF image is analyzed by extracting the specific parameter values quantifying the RF frequency spectrum associated with specific structures. The RF echoes contain frequency-dependent information that depends on the tissue microstructure smaller than the wavelength of ultrasound. The system exploits the tissue dependent features contained within the RF backscattered data to further reduce false positives in the envelope-based nerve detection algorithm. In this approach, the frequency dependence of the backscattered signal is represented through an estimated power spectrum. The power spectrum is the magnitude squared of the Fourier transform of a gated RF backscattered signal. The power spectrum is a convolution of the impulse response of the system, a function describing the spatially-dependent diffraction and a tissue scattering function. The impulse response controls the bandwidth that can be used for analysis. In one embodiment, a frequency analysis bandwidth of approximately 5 to 12 MHz will be used.

Figure 64:
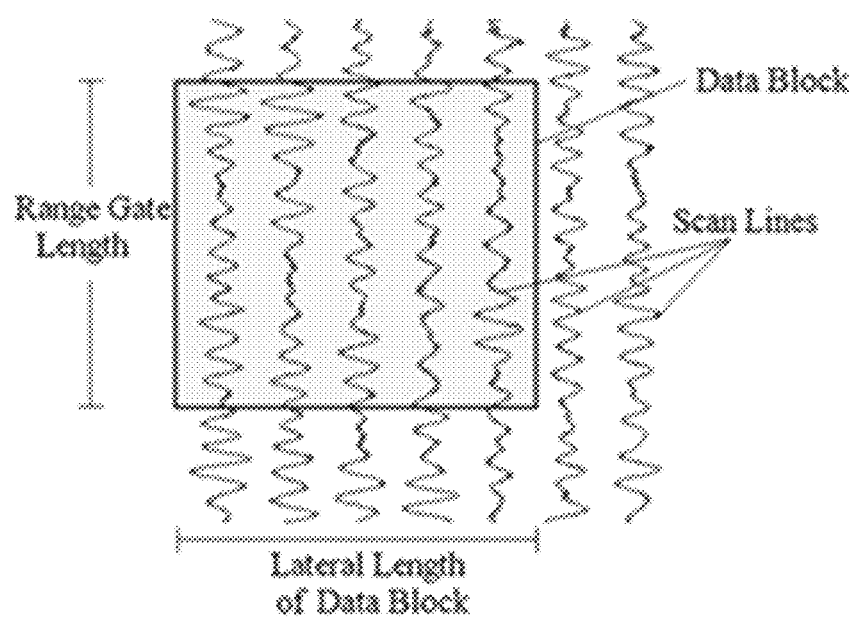
FIG. 64 depicts a diagram of the RF backscatter received of a data block.

In practice, the normalized power spectrum is estimated from a block of data. The block of data consists of several independent scan lines (separated by a beam width) (see FIG. 64). The width of the block depends on the number of scan lines in the data block. Each scan line is an RF backscattered echo from the tissue returning versus time and is windowed with a rectangular window. The length of the data block depends on the length of the windows used to gate the signals. The data blocks can be localized to a tissue region by correlating the data block location to B-mode images of the tissue region being scanned. A normalized power spectrum is estimated for each scan line in the data block and then each spectrum is averaged to provide a normalized power spectrum for the whole data block.

The locations of the data blocks to be analyzed by the RF-based classifier are automatically chosen based on the envelope-based nerve detection algorithm. The envelope-based nerve detection algorithm is configured to detect nerves in the ultrasound image with as close to 100% true positive as possible. With this configuration, the presence of false positives will occur (ideally at a low rate). Any regions that are detected by the envelope-based nerve detection algorithm as nerve are then passed to the RF data analysis routine in order to further reduce false positives. Each region that is detected as nerve is then broken into smaller data blocks for RF spectral analysis that includes analyzing the spectral signature of the tissue. This process can be performed for other types of tissue other than nerve.

The normalized power spectrum for each data block is function of amplitude or signal energy versus frequency. As such, the normalized power spectrum must be parameterized in order to input information about the normalized power spectrum into a classifier. A model of scattering from nerve or other tissue allows properties of the tissues to be extracted by parameterizing the normalized power spectrum.

Figure 65:
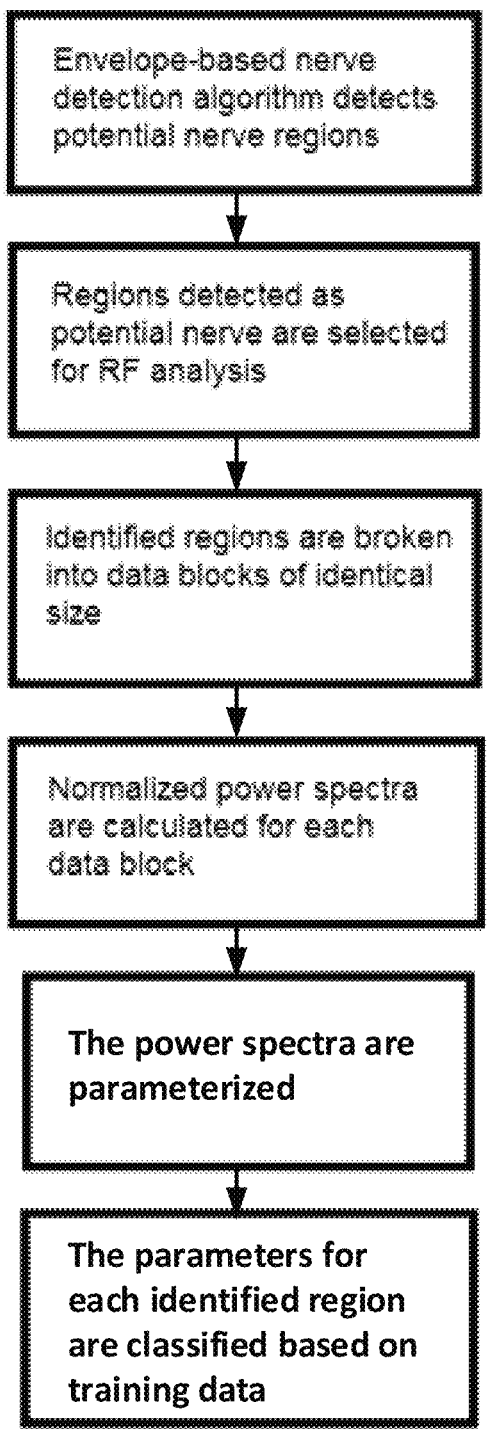
FIG. 65 represents a flow chart of the RF based classification system.

Each data block will provide estimates of the two constants. Data blocks within regions identified as nerve will then be analyzed with the RF classifier. A simple linear classifier utilizing the two estimated constants will be constructed. The classifier will be tuned based on training data to provide 100% true positive detection of the nerve, i.e., prevent the additional analysis to cause a false negative. The independent information provided by the RF analysis will be combined with the envelope-based nerve detection algorithm to reduce false positives. The execution of the RF-based classification routine is summarized by the flow chart in FIG. 65.

In addition, to improve the efficiency and the rate at which the system can process the data to permit real-time detection, the system may also employ multi-frame voting. Image frames from each orientation are used to detect nerve, and because the number of ultrasonic images collected is at a faster rate than real time display, the detection results from a number of sequential frames can be accumulated. If one of the frames in the collected sequence results in positive nerve detection, the first image with a positive nerve detection is displayed. If no nerves are detected in the collected sequence of frames, the first frame in the collected sequence will be displayed. The number of frames in a collection sequence will be small enough to allow 30 frames per second to be displayed based on a representative image from each collection sequence. Therefore, for example, if the first frame detects a nerve but the two sequential frames thereafter do not, the system will not classify the first frame because it is likely a false positive. This will reduce the amount of frames that will require classification, which will improve the efficiency and processing speed of the system.

Once the muscles are split and the surgical site 46 is reached, the surgeon can place a k-wire through the conduit to confirm that the surgical site 46 is reached and anchor the device 10 with respect to the surgical site 46. A retractor tool 48 may be put into place to give the surgeon a direct surgical working conduit to the surgical site 46. Alternatively, a series of dilators may be sequentially placed over the main body 16 to create the working space.

As shown in FIG. 19, an embodiment of the retractor system 48 may include a first blade 49 and a second blade 51, both of which may be semi-circular in shape that form an opening that fits snugly around the outer diameter the main body 16. It is appreciated that the cross-sectional shape of the blades can mimic the shape of the main body 16 (e.g., triangular, oval, square, rectangular, etc.). Once at the surgical site, the retractor blades 49, 51 may be configured to separate relative to one another so as to expand the dissection and to enable the device 10 to be removed and allow for direct visualization of the surgical site 46 as shown in FIG. 19. It is contemplated that the distal ends 53 of the first 49 and second 51 blades are adjacent to the distal portion 14 of the main body 16. Any known type retractor system may be used with the device 10.

Figure 38:
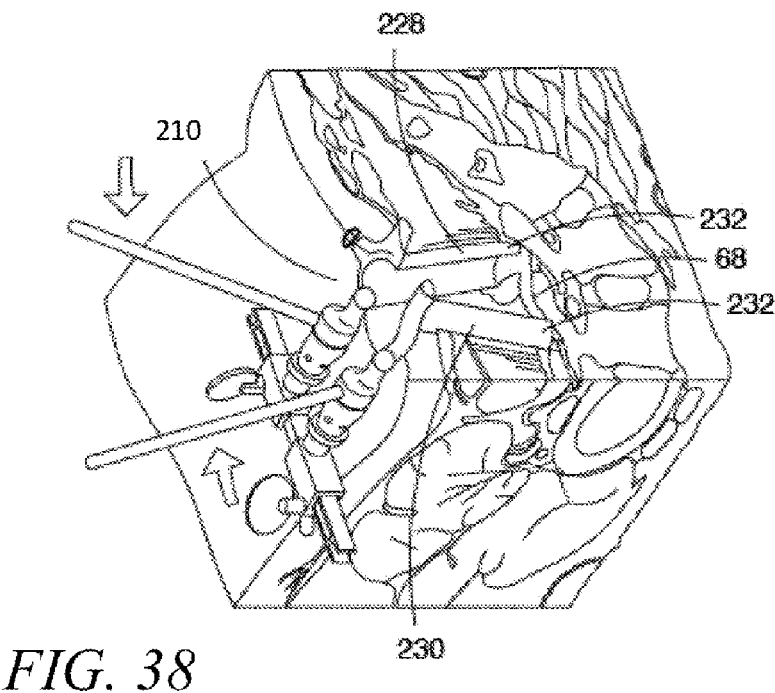
FIG. 38 depicts one embodiment of the present disclosure in use with a retractor system.

In one embodiment, a retractor system 226, like the one disclosed in FIG. 38, may be disposed over the device 10 and configured to expand to create a working space within the anatomy of the patient once a surgical site, or other location where a surgical procedure is to take place, is reached. This embodiment of the retractor system 226 includes a first blade 228 and a second blade 230, both of which are semi-circular in shape that form an opening that fits snugly around the outer diameter the main body 16. Once at the surgical site, the retractor blades 228, 230 are configured to separate relative to one another to expand the dissection so as to enable the device 10 to be removed and allow for direct visualization of the surgical site 68 as shown in FIG. 38. The distal ends 232 of the first and second blades (228 and 230) may be adjacent to the distal portion 14 of the main body 16. Any type known retractor system may be used with the device 10. It can be appreciated that stimulation electrodes, visualization cameras and illumination devices (optical, ultrasound, infrared and ultraviolet) may also be placed along or within the retractor blades 228, 230 so as to allow for nerve detection as discussed above.

Figures 39, 40:
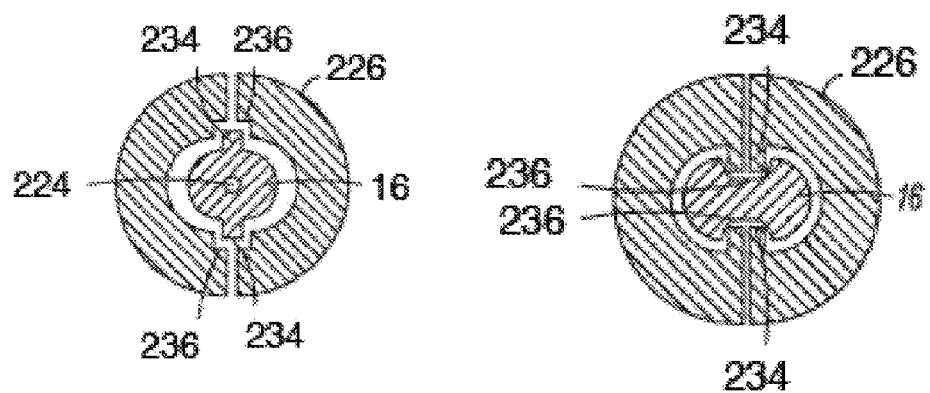
FIG. 39 depicts one embodiment of the retractor system of the preset invention.
FIG. 40 depicts another embodiment of the retractor system of the preset invention.

As shown in FIG. 39, a cross-sectional view of the retractor 226 disposed around the device 10, the main body 16 of the device 10 may have a raised channel or channels 234 disposed along its length in a direction along the its longitudinal axis that is configured to slidingly receive a complimentary groove 236 formed by the first and second blades 228, 230 of the retractor system 226. In some aspects, the raised channel 234 and/or groove 236 may have a square, rectangle, semi-spherical or a similar cross-sectional shape. Further, the number and location of the channel 234 and groove 236 may vary. For example, but without limitation, the may only be one channel/groove running along the main body 16.

Alternatively, there may be more than two channels/grooves that are equidistantly placed about the outer surface of the main body 16. The channel and groove may also be transposed, such that the groove 236 is on the main body 16 and the raised channel 234 is formed along the blades 228, 230, as shown in FIG. 40, such that the groove 236 prevents the blades 228, 230 from expanding when the retractor 226 is disposed over the device 10. The channel 234 and groove 236 may extend along only a portion of the main body 16 of the device 10 and the blades 228, 230.

The retractor system 226 may consistent of multiple sets of blades 228, 230 with varying thickness and diameter. For example, and without limitation, the blades 228, 230 may vary in size so as to have an overall outer diameter ranging from 2 mm to 80 mm when in the closed (e.g., collapsed) configuration. Further, the blades 228, 230 may be configured such that they create a 2 mm to 220 mm opening within the patient's body when in the expanded configuration. The device 10 and retractor system 226 may be configured such that a first set of blades 228, 230 having a larger retracted diameter may be used to create a first opening within the patient's body and then a second set smaller diameter blades having a retracted diameter that is different than the first set of blades 228, 230 may be slidingly disposed over the main body 16 and within the first opening and retracted to open a second opening within the patient's body at a location distal to the first opening. The openings created by the first and second set of blades may have different opening diameters. The retractor system 226 may allow the operator to create multiple openings having different retracted diameters at different anatomic levels within the patient. A light source (not shown) may be disposed at the distal ends, or along the length, of the blades 228, 230 to illuminate the opening within the patient's body and illuminate the region of the patient's anatomy within and distal to the opening created by the blades 228, 230 In addition, a conduit (not shown) may also be formed within the blades so as to receive one or more of: a medical instrument, such as a k-wire to anchor the blades 228, 230 to a surgical site such as the disk space between two vertebra; an illumination device, such as an optical fiber, to provide additional illumination to a particular region of the patient's anatomy; an electrical conduit to provide neural stimulation; a ultrasound probe to image or detect particular regions of a patient's anatomy; an image capture device; a fiber optic cord that emits visible or infrared light to image or detect particular regions of a patient's anatomy; and the like. The blades 228, 230 may be made out of any preferable surgical grade material, including but not limited to, medical grade polymer including PEEK (polyether ether ketone), and may be transparent (e.g. made out of clear plastic) or translucent.

Figure 20:
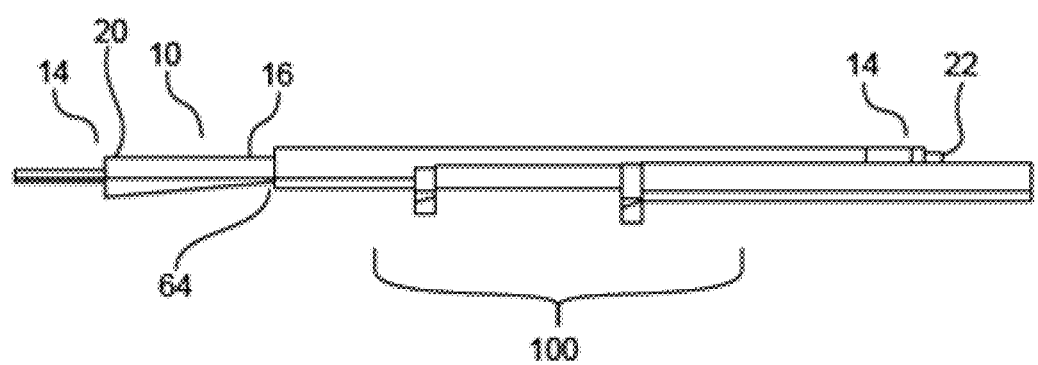
FIG. 20 depicts one embodiment of the dilator system that can be used with embodiments of the present disclosure.

A series of dilating cannulas (e.g. dilators 100), as shown in FIG. 20, may also be slidingly placed around the main body 16 of the device 10 so as to expand the diameter of the dissection made by the distal portion 14 of the device 10. The technique of employing a series of dilating cannulas to create a working space for direct visualization used in other medical procedures to create a working space may also be used in conjunction with the device 10.

In another embodiment, a retractor system 226 may be integrated with the device 10 such that it forms part of the main body 16 and can be deployed once at the surgical side. The retractor system 226 in this embodiment may expand radially away from the longitudinal axis of the main body 16 to expand the path created by the main body 16. The main body 16 may then be withdrawn from the surgical site so as to create a working portal within the retractor system 226.

Figure 63:
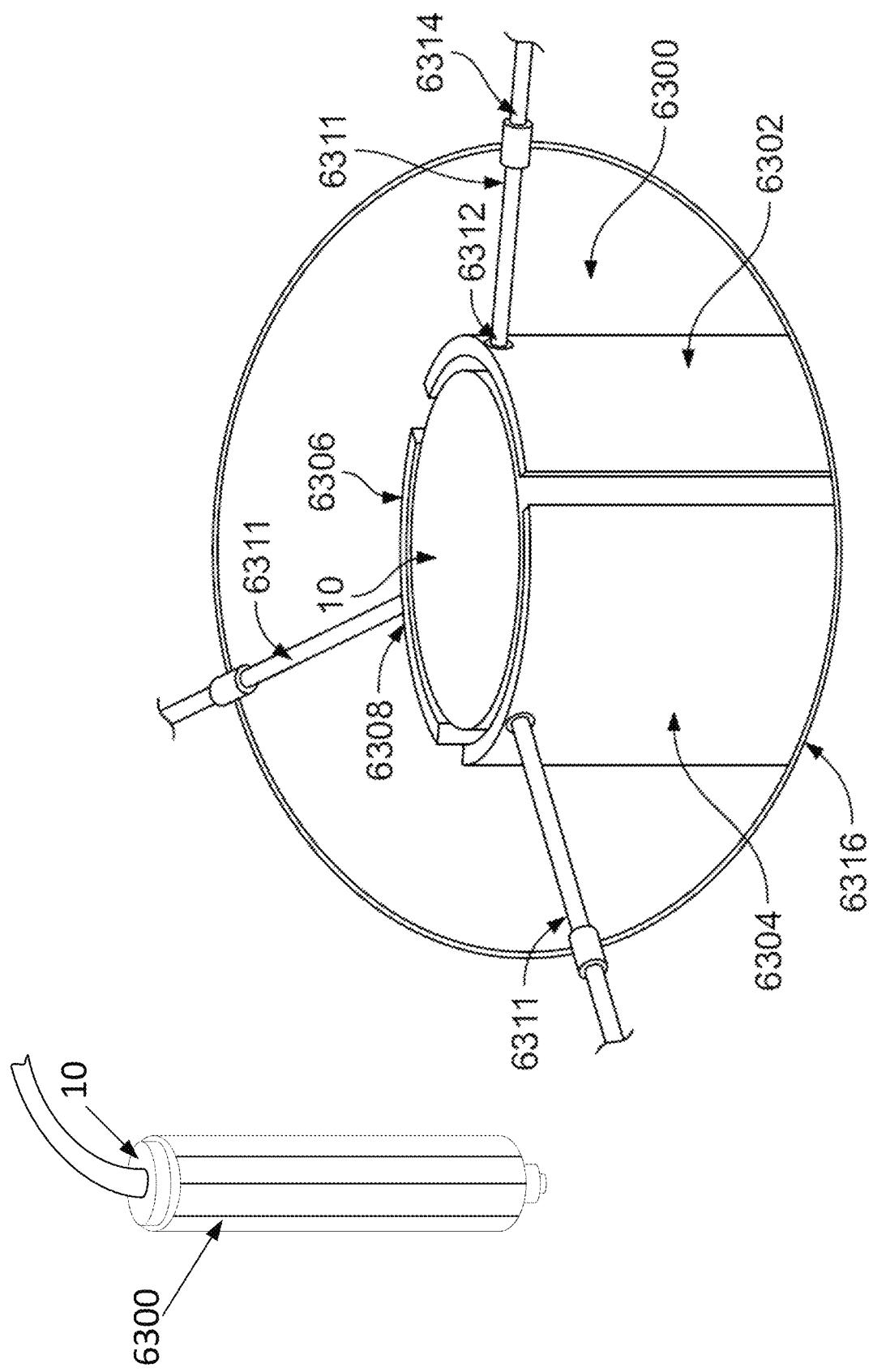
FIG. 63 depicts another embodiment of a retractor system of the present disclosure.

In still another embodiment, as shown in FIG. 63, a retractor 6300 may form part of the main body of device 10 such that the blades 6302, 6304, 6306 of the retractor 6300 expand radially away from the longitudinal axis of the device 10. Each blade may include an attachment member 6308 to connect to a first end 6312 of a guide rod 6311. The second end 6314 the guide rod 6311 may attach to an annular ring 6316 that may be situated about the surgical area. Examples of the annular ring and attachment mechanism for attaching to a surgical table include the SynFrame Access and Retractor System by Synthes, Inc., described in the "SynFrame Access and Retractor System Technique Guide", the entirety of which is incorporated herein by reference.

In one embodiment, a flexible membrane or sheath may be disposed around the retractor 6300 so as to prevent tissue from creeping into the spaces formed between retractor blades 6302, 6304, 6306 as the retractor 6300 expands radially away from the longitudinal axis of the device 10. The sheath or flexible membrane will form a barrier encircling the retractor 6300 and provide a clear and tissue-free working channel once the retractor 6300 is expanded. It can be appreciated that the flexible membrane or sheath may only be disposed along a portion of the length of the device 10 that comes into contact with the tissue.

In an alternative embodiment, one or more transducers 26 of the ultrasound imager 24 may be disposed within one or more blades 6302, 6304, and 6306 of the retractor 6300. In another embodiment, the retractor 6300 may form the main body 16 of the device 10, such that when the retractor 6300 is in the open (or expanded) position, the working channel is created between the inner surfaces of the one or more blades 6302, 6304 and 6306. In other words, the main body 16 of the device may be comprised primarily of the retractor blades 6302, 6304 and 6306.

Once the device 10 is at the surgical site, the surgeon may attach the first end 6312 of the guide rod to the retractor blades 6302, 6304, 6306 via the attachment member 6308. The attachment mechanism between the retractor blades 6302, 6304, 6306 and attachment member 6308 may include a mechanical connector such as a hook, latch, or snap fit, or may comprise a magnetic connection or the like.

Upon attaching the attachment member 6308 to each retractor blade, the surgeon may then retract each of the retractor blades 6302, 6304, and 6306 radially away from the longitudinal axis of the device 10. Once the blades have been retracted, the device 10 may be removed to allow the surgeon access to the target site.

It can be appreciated that the number of blades of the retractor 6300 can vary, from two to over six or more. In addition, to provide resiliency, the retractor blade may include a metal frame reinforcement to provide the strength needed for the blades to withdraw and displace portions of the anatomy.

Once this direct access to the spine is achieved, the surgeon is able to perform a standard discectomy (removing the intervertebral disc), corpectomy (removing the vertebral bone) or fusion (uniting two bones together) with surgical tools.

After disc material is removed, the surgeon may be able to insert an implant/spacer through the same incision from the side. This spacer (cage) may help hold the vertebrae in the proper position to make sure that the disc height (space between adjacent vertebral bodies) is correct and to make sure the spine is properly aligned. This spacer, together with a bone graft, may be designed to set up an optimal environment to allow the spine to fuse at that particular segment. The surgeon may use fluoroscopy to make sure that the spacer is in the right position. The surgeon may then remove the refractor and suture any incisions.

Spinal surgeons oftentimes access the intervertebral disc space and vertebral body via a transpsoas approach. The psoas muscle however has a network of nerves (lumber plexus) within the muscle and their exact location can be unpredictable The surgeon must therefore get to the disc while avoiding these nerves so as not to cause nerve damage or paralysis when performing surgery. The present disclosure allows the surgeon to visualize where nerves lie before penetrating the psoas muscle. The device 10 and the classification algorithms may be used to create a quantitative image and/or map (2D or 3D) of the nerve tissue while the device 10 is placed above the psoas, providing a surgeon a path that avoids nerves and gets to the disc space. In some embodiments, a mapping of target tissue proximate to the surgical site may be provided by the ultrasound imager 24. When the tip 22 is disposed adjacent to the psoas muscle, the surgeon may slide a first set of blades of a retractor system (such as retractor system 48) over the device and expand the retractor system to create a first working space (also referred to as a superficial dock). This working space may allow the surgeon to visually inspect the psoas muscle and the surrounding region either via naked (eye) inspection or with the optical camera/dissector (e.g., one or more components of device 10). Next, the surgeon may continue the procedure by using the device, which is now disposed within the first working space to dissect through the psoas muscle as described herein. Once the tip 22 has reached the surgical site, which is the disc space here, a second set of retractor blades which are smaller than the first set of blades may be slid over the device 10 and expanded to create a second working space that is smaller in diameter than the first working space. The surgeon may then continue with the procedure in the manner discussed herein. One benefit of establishing the first working space may be that it allows the surgeon to remove the device 10 from the surgical site once the procedure is completed at the first surgical site and reposition and reinsert the distal tip 22 of the device 10 within the first working space that is formed above the psoas muscle at a second location to allow the surgeon to penetrate the psoas muscle to reach a second surgical site to conduct and complete another procedure or a multi-level procedure in which psoas dissection is currently dangerous because of the interposed neurovascular structures (L3-4 and L4-5 disc space or a lumbar corpectomy—removal of two discs and the intervening bone). It is appreciated that the tip 22 is optional and the distal end 21 of the device 10 maybe the portion of the device that is advanced towards the surgical site.

In some embodiments employing the device 10 having the channel 4930, when the tip 22 is disposed adjacent to the psoas muscle, the surgeon may position surgical tools/implants through the channel 4930 to access the surgical site while allowing the transducer(s) to collect data for real-time display. By allowing the surgeon to perform surgery while the device 10 is in place, the transducer can record and collect data throughout the surgery. The device 10 may also serve as a retractor of tissue, thereby pushing surrounding tissue to the side and assisting with creating the working portal for the surgeon. Once the tip 22 has reached the surgical site, the surgeon may continue the use of tools through the channel 4930 or may employ a second set of tools, such as retractor blades, over the device 10. The surgeon may then continue with the procedure in the manner discussed herein.

In an alternative embodiment, the device 10 may not traverse the psoas muscle, but instead, may take one of at least two different routes to access the surgical site. In one such alternative embodiment, the device 10 may be positioned adjacent to, or next to, the surface of the psoas muscle and where a clear route to the surgical site may be determined, and in another such alternative embodiment, the device 10 may be maneuvered around the psoas muscle to access the spine from a trajectory that is between the psoas muscle and any vasculature. Each of these embodiments is discussed below.

With respect to the first alternative embodiment (illustrated in FIGS. 66 and 67), prior to using the device 10 during a surgical procedure on a patient's spine, the surgeon may first make a single incision into the patient's midsection, and may use his/her finger or a blunt object to dissect through the retroperitoneal space, creating a path to the psoas muscle. At this point, the device 10 may be inserted through the single incision and maneuvered along the path previously created by the surgeon and positioned at the surface of the psoas muscle. The distal end 12 of device 10 may be adjacent to the surface of the psoas muscle, but the distal end of the device 10 does not penetrate the psoas muscle. The distal end 12 may be placed directly adjacent to the psoas muscle or there may be a gap between the surface of the psoas muscle and the distal end 12 of the device 10. In some embodiments, this gap may range between 1 and 40 mm. Further, the device 10 may traverse the retroperitoneal space filled with liquid.

The device 10 may be used to scan the entirety of a region of the psoas muscle that is between the device 10 and the surgical access site. In some embodiments, the scanning depth may range between 1 and 40 mm. During this scanning process, the device 10 and associated system may scan the psoas muscle for nerves, vasculature and the like, in order to determine a clear trajectory between the distal end 12 of the device 10 and the surgical site. In some embodiments, the clear trajectory may be determined by locating and identifying nerve and/or vasculature and mapping a path to avoid the nerve and/or vasculature. In some other embodiments, the clear trajectory may be determined by moving or adjusting at least a portion of the device 10 until it is determined that there is a clear path between the distal portion 12 of the device 10 and the surgical site. In the former approach, the device 10 and the accompanying system may image the psoas muscle by way of the device's ultrasound transducer and the device's quantitative detection methods, and a path from the distal end 12 of the device 10 to the spine that is clear of nerve, vasculature, and other anatomical features can be identified. In the latter approach, there may be no need to identify the types of anatomical structures that are present. Instead, it may be sufficient to detect the presence of non-psoas muscle (for example, the presence of anatomy, such as nerves or vasculature, which is not psoas muscle) that falls within the path between the distal end 12 of the device 10 and the surgical site. It can be appreciated that the path may be or may not be a linear path between the distal end 12 of the device 10 and surgical site. The quantification technology discussed in the applications referenced above is incorporated herein by reference and may be used to detect the path. In some embodiments, the path may be displayed on a display (e.g., GUI).

Figure 66:
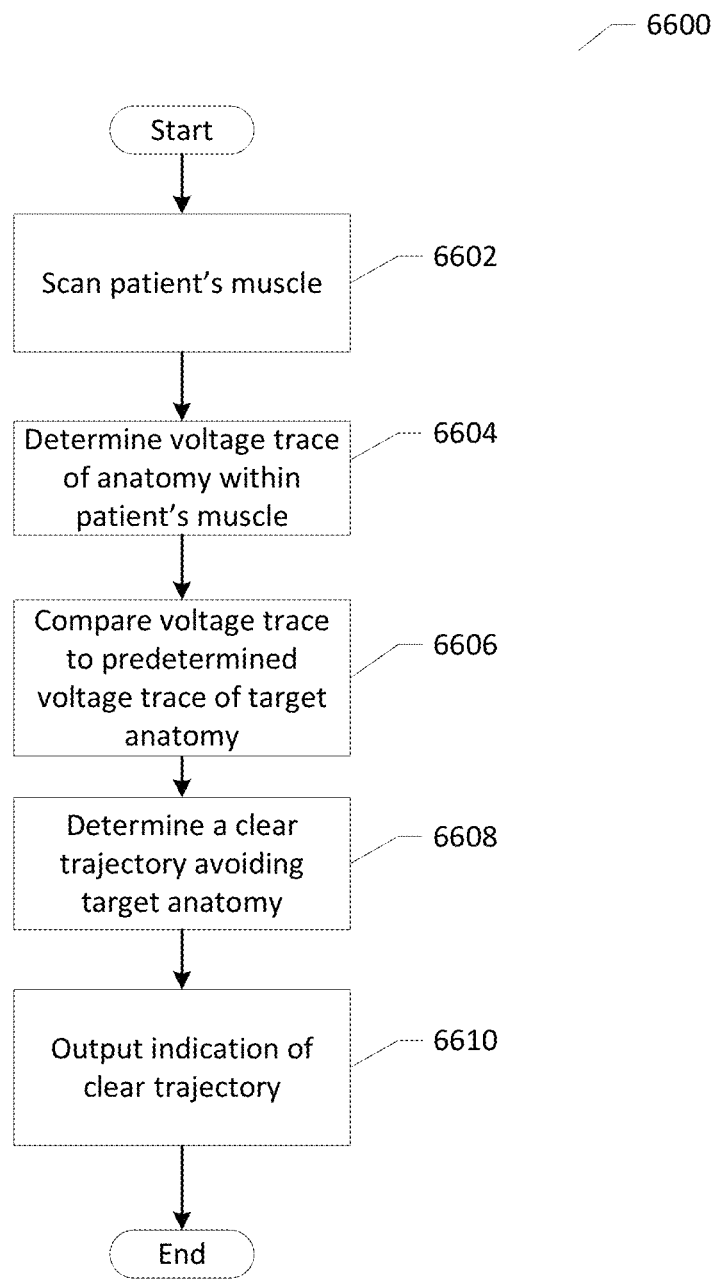
FIGS. 66-68 are example flow charts illustrating methods performed in accordance with one or more aspects as described herein.

FIG. 66 is an exemplary flow diagram illustrating the first alternative 6600 in accordance with one or more disclosed features described herein. In one or more embodiments, the process illustrated in FIG. 66 and/or one or more steps thereof may be performed by one or more computing devices (e.g., computing device 4701, 4751, and the like). In other embodiments, the process illustrated in FIG. 66 and/or one or more steps thereof may be embodied in computer-executable instructions that are stored in a computer-readable medium, such as a non-transitory computer-readable memory. The steps in this flow diagram need not all be performed in the order specified and some steps may be omitted and/or changed in order.

At step 6602, the device 10 may be used to scan a patient's muscle. For example, the device 10 may be used to scan the patient's psoas muscle. The scan may include the use the device's ultrasonic transducer 26 placed adjacent to the psoas muscle. At step 6604, a voltage trace may be determined, based on the scan. At step 6606, the voltage trace may be compared to one or more predetermined, or otherwise known, voltage traces. For example, the predetermined voltage traces may include voltage traces of one or more nerves, vasculatures and/or other common anatomy. At step 6608, a clear trajectory may be determined between the distal end 12 of the device 10 and the surgical site. The clear trajectory may correspond to a path between the device 10 and the surgical site which is clear from nerves, vasculature or other anatomy represented by the predetermined voltage traces. In some embodiments, the clear trajectory may comprise a path including a predetermined margin of clear tissue. For example, the path may correspond to a linear or nonlinear path free of nerves and vasculature, at least within a predetermined distance from the center of the path. The margin may be selected by the operator in order to allow needed clearance for surgical instruments to pass, depending on the procedure planned.

At step 6610, an indication of the clear trajectory may be output. For example, in some embodiments, the indication of the clear trajectory may be displayed on a monitor so that a surgeon may see a depiction of the clear trajectory. In some other embodiments, an audible indication may be output to indicate that a direct linear path between the device 10 and the surgical site represents a clear trajectory.

The steps 6602-6610 may be repeated and may occur in real time as the surgeon moves the device 10 or otherwise repositions the device 10.

Figure 67:
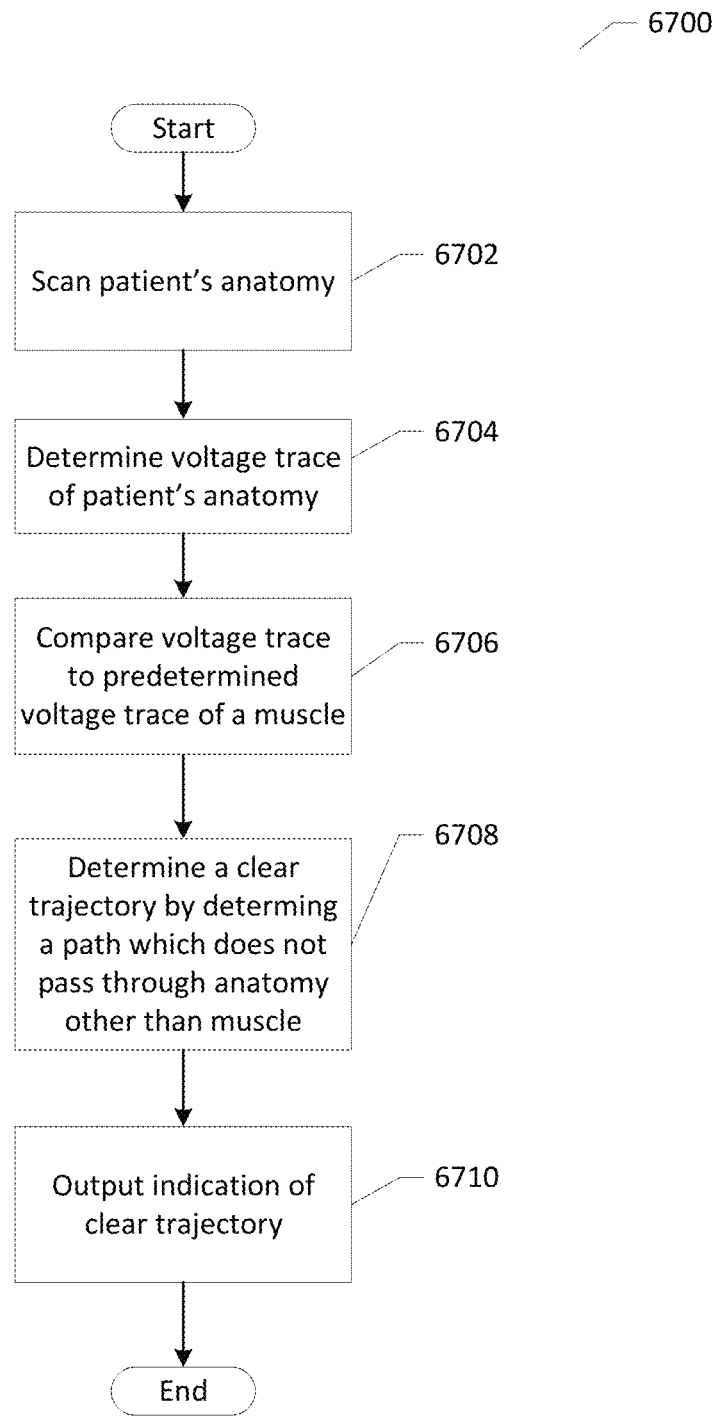

FIG. 67 is an exemplary flow diagram illustrating another embodiment of the first alternative 6700 in accordance with one or more disclosed features described herein. Again, in one or more embodiments, the process illustrated in FIG. 67 and/or one or more steps thereof may be performed by one or more computing devices (e.g., computing device 4701, 4751, and the like). And in other embodiments, the process illustrated in FIG. 67 and/or one or more steps thereof may be embodied in computer-executable instructions that are stored in a computer-readable medium, such as a non-transitory computer-readable memory. The steps in this flow diagram need not all be performed in the order specified and some steps may be omitted and/or changed in order.

At step 6702, the device 10 may be used to scan a patient's muscle. For example, the device 10 may be used to scan the anatomy within the patient's psoas muscle. The scan may include the use the ultrasonic transducer 26. At step 6704, a voltage trace may be determined based on the scan. At step 6706, the voltage trace may be compared to one or more predetermined, or otherwise known, voltage traces of muscle. For example, the predetermined voltage traces may include one or more voltage traces of psoas muscles. At step 6708, a clear trajectory may be determined between the distal end 12 of the device 10 and the surgical site. The clear trajectory may correspond to a path between the device 10 and the surgical site which includes only muscle, such as psoas muscle. In some embodiments, the clear trajectory may comprise a path with a predetermined margin of muscle. For example, the path may correspond to a linear or nonlinear path comprising only muscle, at least within a predetermined distance from the center of the path. As discussed above in relation to FIG. 66, the margin may be selected by the operator in order to allow needed clearance for surgical instruments to pass, depending on the procedure planned.

At step 6710, an indication of the clear trajectory may be output. For example, in some embodiments, the indication of the clear trajectory may be displayed on a monitor so that the surgeon may see a depiction of the clear trajectory. In some other embodiments, an audible indication may be output to indicate that a direct linear path between the device 10 and the surgical site represents a clear trajectory.

The steps 6702-6710 may be repeated and may occur in real time as the surgeon moves the device 10 or otherwise repositions the device 10.

Once the path is identified, a surgical accessory such as a k-wire, catheter, guide wire, needle, smart needle, and/or camera then be may be placed along the path and extend through the psoas muscle (i.e., transpsoas) along the predetermined path to the surgical target site. Next, a dilator or series of dilators or a retractor system may be placed along the same path to create a working portal and direct access to the surgical site so as to enable to surgeon to perform a medical procedure, such as a spinal fusion.

With respect to the second alternative embodiment (illustrated in FIG. 68), after the surgeon has created a path from the incision site to the psoas muscle with his/her finger or blunt instrument, the device 10 may be inserted into the patient's mid-section through the incision site and maneuvered between the patient's nerves, muscles, and vasculature to find a path between the patient's psoas muscle and vasculature (aorta/iliac artery/iliac vein), and that leads to the disc space from an oblique approach that is free of the nerves, muscles, and vasculature. The device 10 may be used to scan the patient's anatomy for a clear trajectory as the device is advanced toward the surgical site. A k-wire or other surgical accessory may then be placed through the device 10 and along this path that is anterior to, and thereby avoiding, the psoas muscle. FIG. 69 illustrates a path, referenced as "Trajectory", used to access the spinal target site according to this second alternative embodiment. As shown in FIG. 69, the path is a non transpsoas path, as no surgical instrument passes through the patient's psoas muscle.

Figure 68:
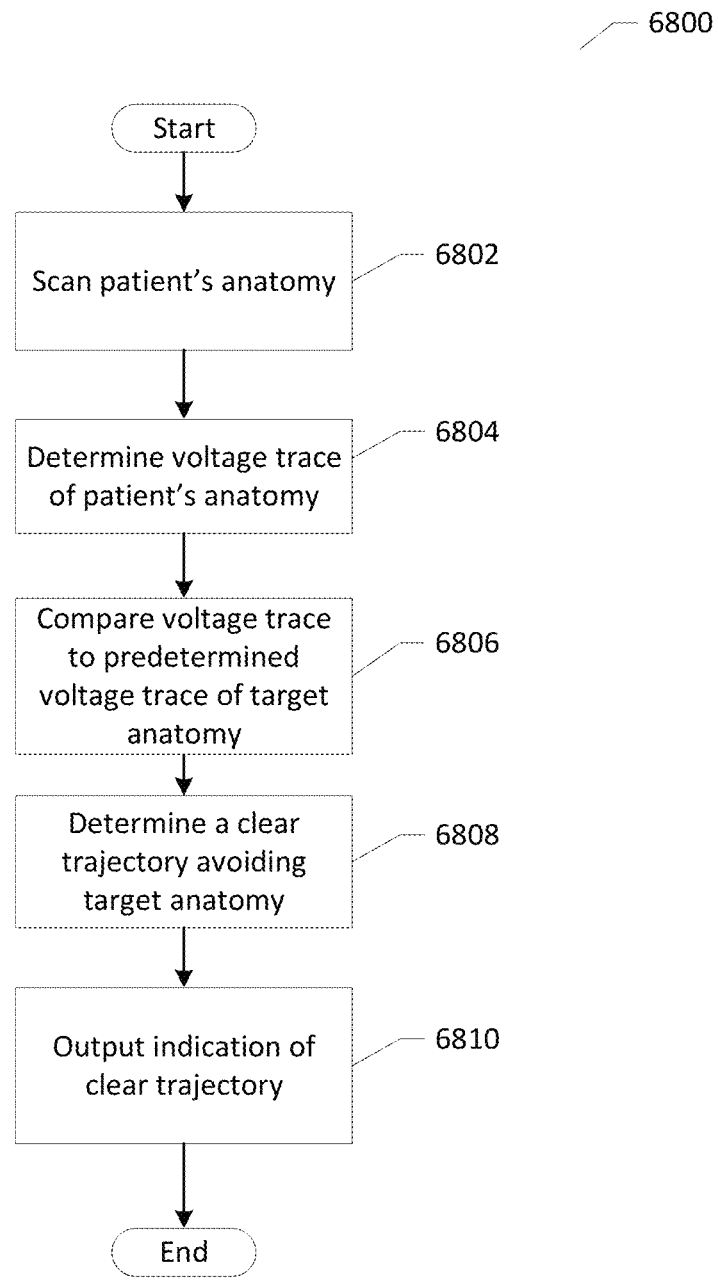
Figure 69:
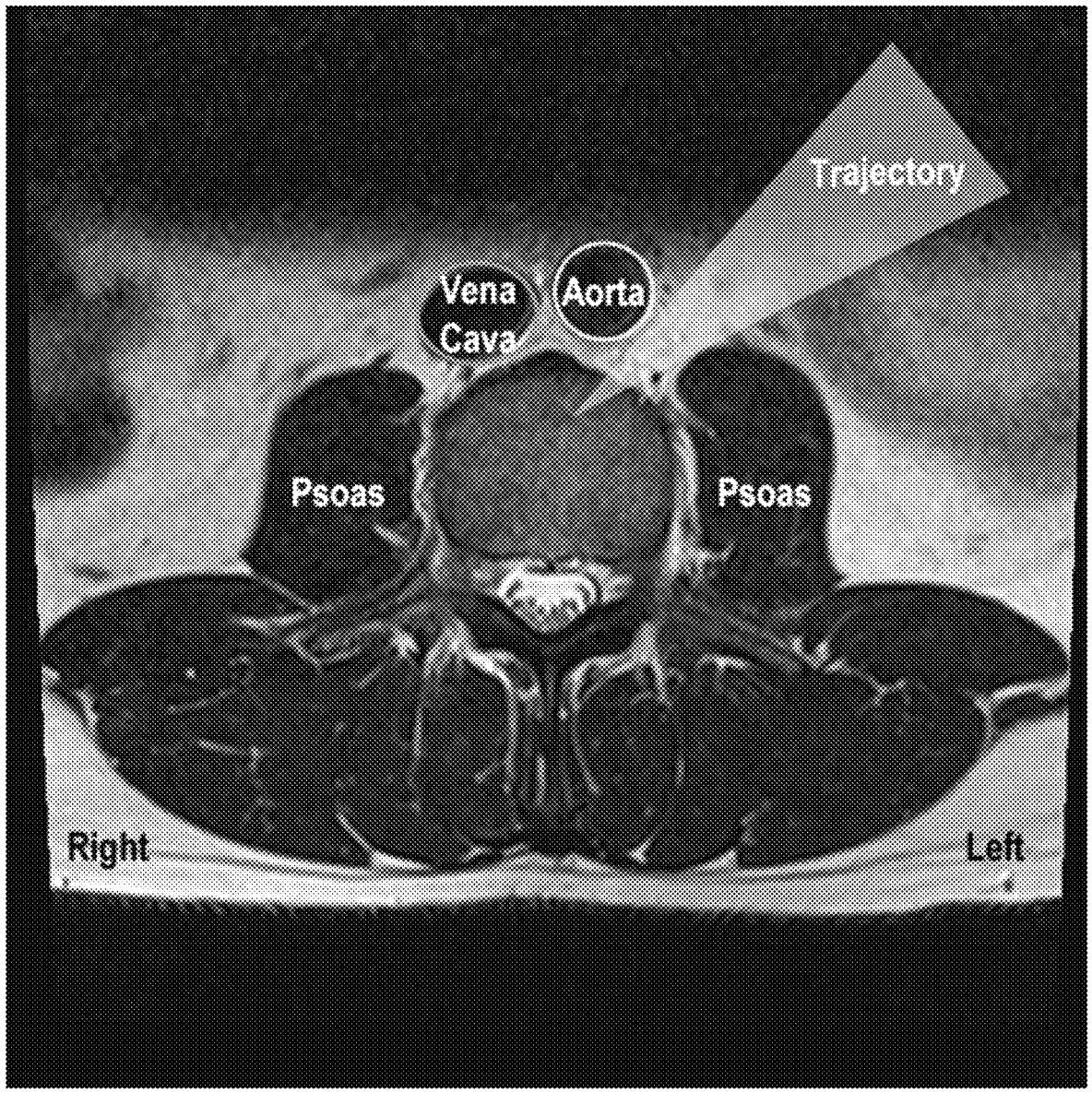
FIG. 69 illustrates a path used to access a surgical site according to one or more aspects as described herein.

FIG. 68 is an exemplary flow diagram illustrating the second alternative embodiment 6800 in accordance with one or more disclosed features described herein. In one or more embodiments, the process illustrated in FIG. 68 and/or one or more steps thereof may be performed by one or more computing devices (e.g., computing device 4701, 4751, and the like). In other embodiments, the process illustrated in FIG. 68 and/or one or more steps thereof may be embodied in computer-executable instructions that are stored in a computer-readable medium, such as a non-transitory computer-readable memory. The steps in this flow diagram need not all be performed in the order specified and some steps may be omitted and/or changed in order.

At step 6802, device 10 may be used to scan a patient's anatomy. For example, the device 10 may be used to scan a region including the patient's psoas muscle. The scan may include the use the device's ultrasonic transducer 26. At step 6804, a voltage trace may be determined based on the scan. At step 6806, the voltage trace may be compared to one or more predetermined, or otherwise known, voltage traces. For example, the predetermined voltage traces may be the voltage traces of one or more nerves, vasculatures, psoas muscle and/or other common anatomy. At step 6808, a clear trajectory may be determined between the device 10 and the surgical site. The clear trajectory may correspond to a path between the device 10 and the surgical site which is clear from nerves, vasculature, psoas muscle and/or other anatomy represented by the predetermined voltage traces. As discussed above, in some embodiments, the clear trajectory may comprise a path with a predetermined margin of clear tissue. For example, the path may correspond to a linear or nonlinear path free of nerves, psoas muscle and vasculature, at least within a predetermined distance from the center of the path. The margin may be selected by the operator in order to allow needed clearance for surgical instruments to pass, depending on the procedure planned.

At step 6810, an indication of the clear trajectory may be output. For example, in some embodiments, the indication of the clear trajectory may be displayed on a monitor so that the surgeon may see the indication of the clear trajectory. In some other embodiments, an audible indication may be output to indicate that a direct linear path between the device 10 and the surgical site represents a clear trajectory.

The steps 6802-6810 may be repeated and may occur in real time as the surgeon moves the device 10 or otherwise repositions the device 10.

The device 10 may also be used for performing an axial lumbar interbody fusion (AxiaLIF). At surgery, the patient may be positioned prone with maintenance of lordosis and the legs spread. A catheter may be inserted into the rectum will allow air to be injected during the procedure for visualization of the rectum. After the surgeon makes a small incision (15-18 mm) lateral to the tip of the coccyx, the distal tip 22 of the device 10 may be inserted through the incision and is passed into the pre-sacral space. The surgeon may use the distal portion 14 of the device 10 to sweep and scan the pre-sacral space to confirm that the space is clear of any offending anatomy (e.g. colon, rectum). The device 10 may be gently passed along the anterior cortex of the sacrum and in the midline to an entry point usually close to the S1-2 junction. Once the trajectory is chosen, a sharp beveled pin may then be driven into the L5-S1 interspace, either through the conduit 36 or after the retractor system 48 or 6300 is deployed. The retractor system, or a series of dilators, may be used to create approximately a 10 mm opening into the sacrum through which a 10 mm channel is drilled into the L5-S1 disc. The device 10 may then be withdrawn from the pre-sacral space and the surgeon may then perform the remaining steps of the AxiaLIF procedure.

Figure 55:
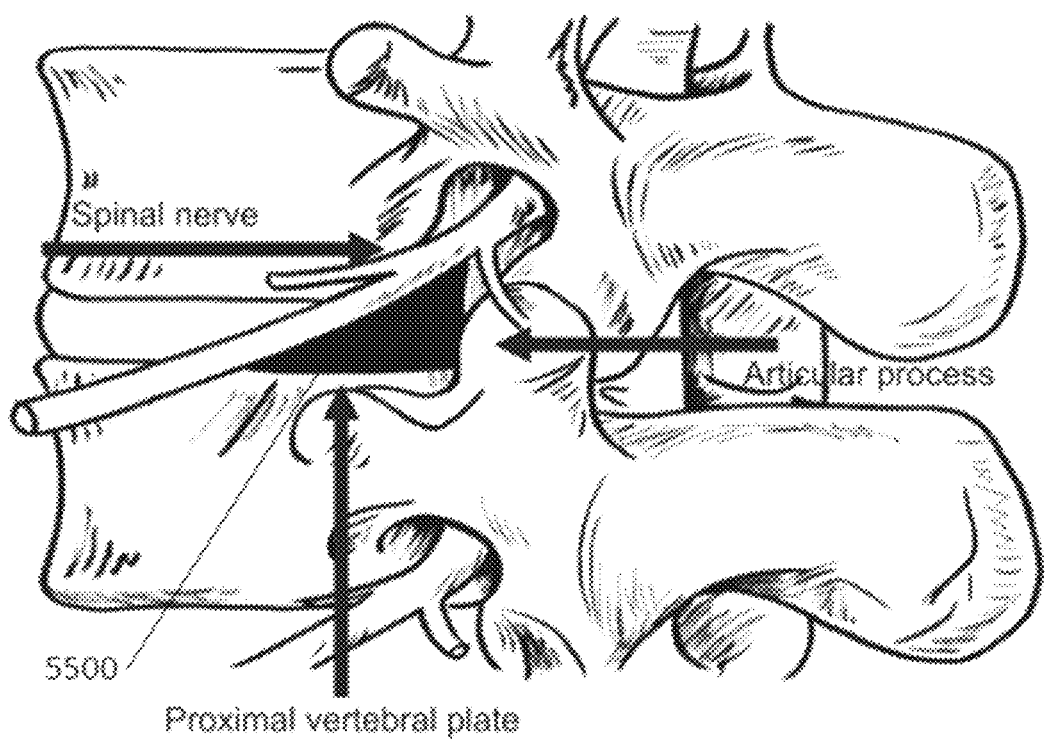
FIG. 55 depicts a visual representation of Kambin's triangle.
Figure 56:
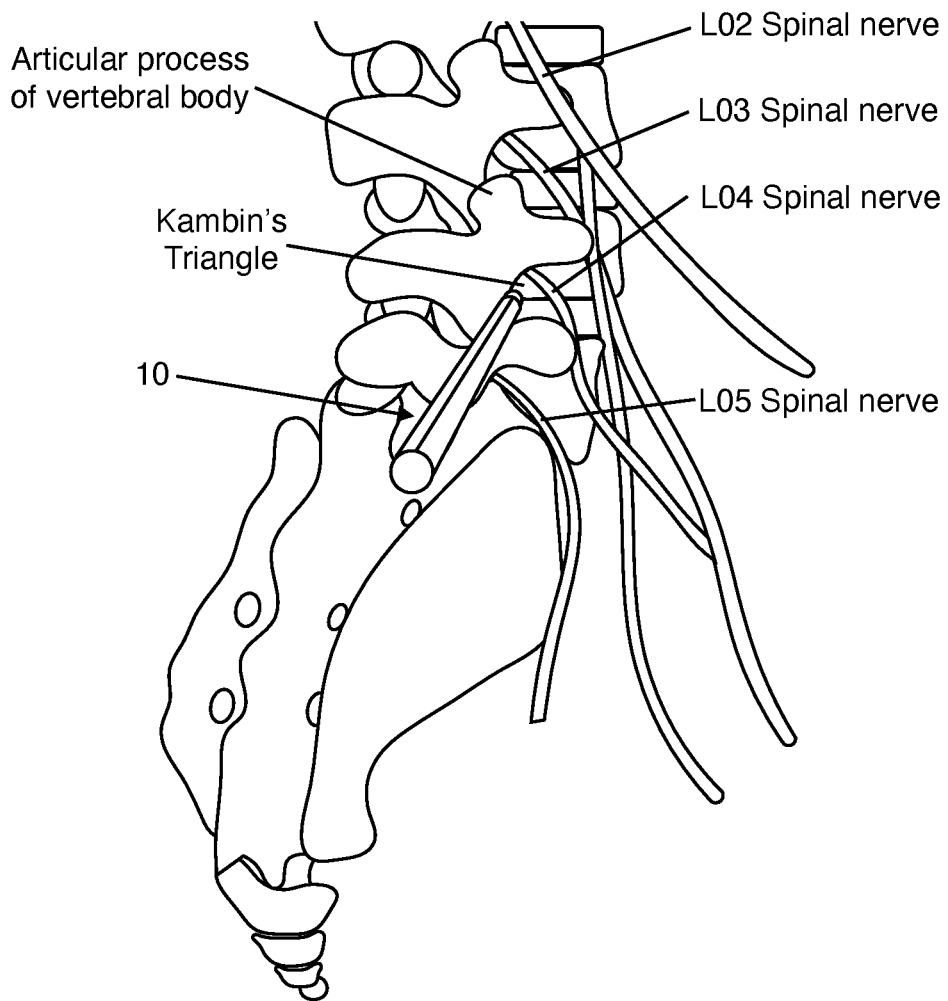
FIG. 56 depicts the device in a position targeting Kambin's triangle, as described herein.

The device 10 may also be used to allow direct access to Kambin's triangle (ExtraForaminal Lumbar Interbody Fusion). For this procedure, patients may be placed in a prone position, typically onto a Jackson Table using a radiolucent frame that allows for restoration of lumbar lordosis. Fluoroscopic imaging may be utilized to identify the epiphyseal plate of the upper and lower vertebral body by controlling the cranial-caudal angle of the image intensifier. Additionally, the fluoroscopic image may be rotated by 20-35 degrees toward the region, so that the superior articular process may be seen at the middle of the intervertebral disc. At this location, the tip 22 of the device 10 may be inserted percutaneously targeting the area commonly referred to as Kambin's triangle. Kambin's triangle is defined as the area over the dorsolateral disc. The hypotenuse is the exiting nerve root, the base (width) is the superior border of the caudal vertebra and the height is the dura/traversing nerve root. FIG. 55 depicts a visual representation of Kambin's triangle 5500. FIG. 56 shows the device 10 in a position targeting Kambin's triangle, as described above.

The device 10 may also be used to ultrasonically identify various anatomical features such as the exiting root, radicular artery, thecal sac and the disc space. A k-wire can then be place into the disc space via the conduit 36 under ultrasonic detection via the device 10 allowing for docking of the dissector/retractor system 48 or 6300. Subsequent dilation can then be performed allowing for access in the intervertebral foramen while directly visualizing neurovascular structures using the device and avoiding these structures when identified by the surgeon.

The device 10 may also be used in treatment of extraforaminal disc herniations, such as in procedures involving extraforaminal intervertebral fusion. A far lateral discectomy is a commonly performed procedure for the treatment of extraforaminal disc herniations. It is routinely done through a paramedian incision using the Wiltse plane. However, the exiting nerve root (i.e. the L04 nerve root at the L45 level, see FIG. 56) is at risk of damage with this approach, as it is normally draped over the disc. In order to decrease the risk of nerve injury, some surgeons currently use intraoperative nerve monitoring; however, intraoperative nerve monitoring relies on advanced anesthetic that may not allow for relaxation of the patient. Recently, surgeons have considered use of interbody cage in intervertebral fusion approaches through the far lateral extraforaminal approach. While there are advantages to a muscle and bone sparing approach to intervertebral fusion, the passage of an interbody cage device into the disc space increases the risk to the exiting nerve as well as the nerves that have exited from proximal levels and are running under the intertransverse membrane. In order to safely perform an extraforaminal intervertebral fusion, we disclose herein use of the device 10 for performing detection of the neurologic structures that run under the intertransverse membrane as well as the exiting nerve root as it is leaving its foramen. Once the nerve is detected, the device 10 can be safely docked on the far lateral portion of the disc, just anterior to the pars interarticularis. Dilators may then be advanced over the main body 16 of the device 10 and then a tubular retractor may be docked on the disc, just anterior to the pars interarticularis and in between the transverse processes of the two involved vertebrae. Once the retractor is safely docked, the surgeon may proceed with preparation of the disc space and endplates and safely insert the intervertebral cage for fusion.

Figure 57:
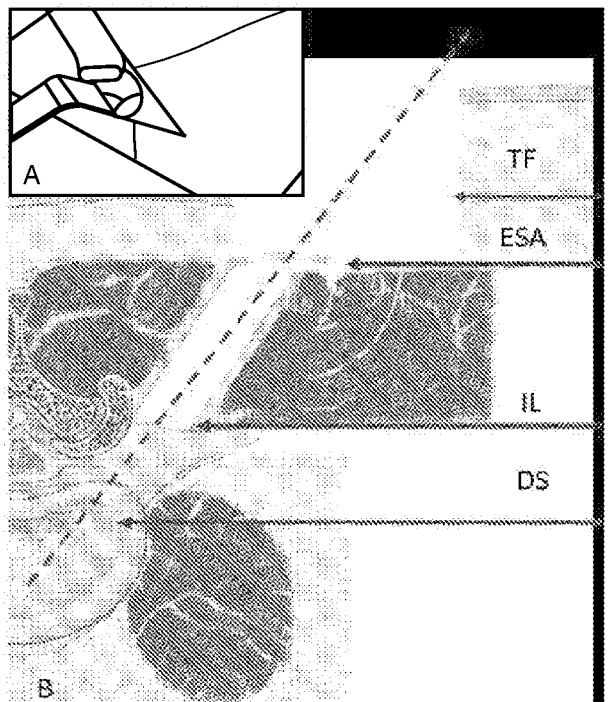
FIG. 57 depicts a surgical incision targeting access to a location on the spine.
Figure 58:
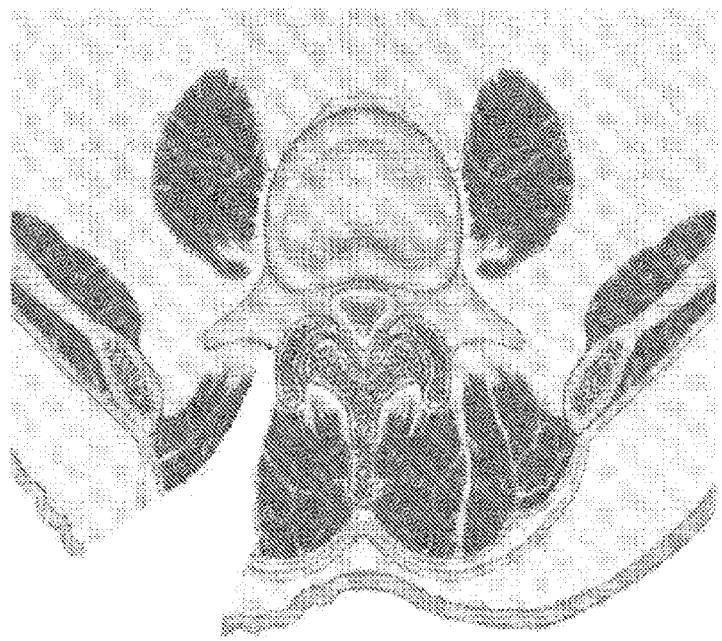
FIG. 58 depicts a surgical approach targeting a portion of the spine.

FIG. 57 depicts a skin incision made approximate 5-6 cm lateral to the midline, according to the methods disclosed herein. The incision may be centered lateral to the facet-pedicle junction. FIG. 58 shows the natural cleavage plane, between the multifidus part of the sacrospinalis and the longissimus part, as may be used for spinal approach in some embodiments. This plane allows direct access to the pars, transverse processes and facet joints with minimal soft tissue dissection and retraction. This approach is less vascular than the mid-line approach, and therefore may result in less bleeding.

In another embodiment, the device 10 may be used to direct the implementation of securing devices, such as a screw, within bone, such as a vertebral body. The device 10 may be used for the surgical implantation of a screw (Jamshidi, spinal needle, catheter, cannula, k-wire) within a vertebral body so as to cannulate the vertebral body for purposes of immobilization, restoration of vertebral height, or for delivery of medicament. The device 10 may be used to detect different characteristics of bone, such as the cortical bone, which is the dense, hard bone on the outside of bony structures, and the cancellous bone, which the soft, compliant spongy bone on the inside of the bone.

In some embodiments, bone may be modeled as a rigid frame porous solid. Cortical bone has a much lower porosity than cancellous bone, which results in a much denser and harder bone structure for cortical bone. The impedance of bone is complex, frequency dependent, and incorporates the pore structure of the bone. The bone is a locally reacting surface, which means that the reflection coefficient from the surface will be a function of the impedance at the surface location. The harder the bone, the higher the impedance mismatch between soft tissue and bone and the higher the resulting reflection coefficient.

Based on the frequency-dependent reflection coefficient, an estimate of the frequency-dependent impedance may be obtained. Similarly, the attenuation of ultrasound in the bone may be dependent on the type bone. The attenuation may be estimated by quantifying the envelope decay of ultrasound versus depth from the surface. Therefore, as will be discussed in greater detail below, bone may then be characterized from models of the bone impedance versus frequency and attenuation of ultrasound to uniquely identify if the ultrasound is from cancellous or cortical bone.

In some embodiments, the device 10 may have different settings (or different transducers) that are unique to which the medium it is scanning. For example, a first setting (or transducer) may be for detecting nerve or other blood vessels in the manner discussed above. Another setting (or transducer) may be for detecting the characteristics of bony structures, such as vertebral body. That way, an all-in-one device 10 may effectively and efficiently allow the surgeon access to the target location and allow the surgeon to scan and assess the target location (e.g., bone) to allow for future operative procedures, such as placing a screw during a pedicle screw fixation procedure.

Figure 59:
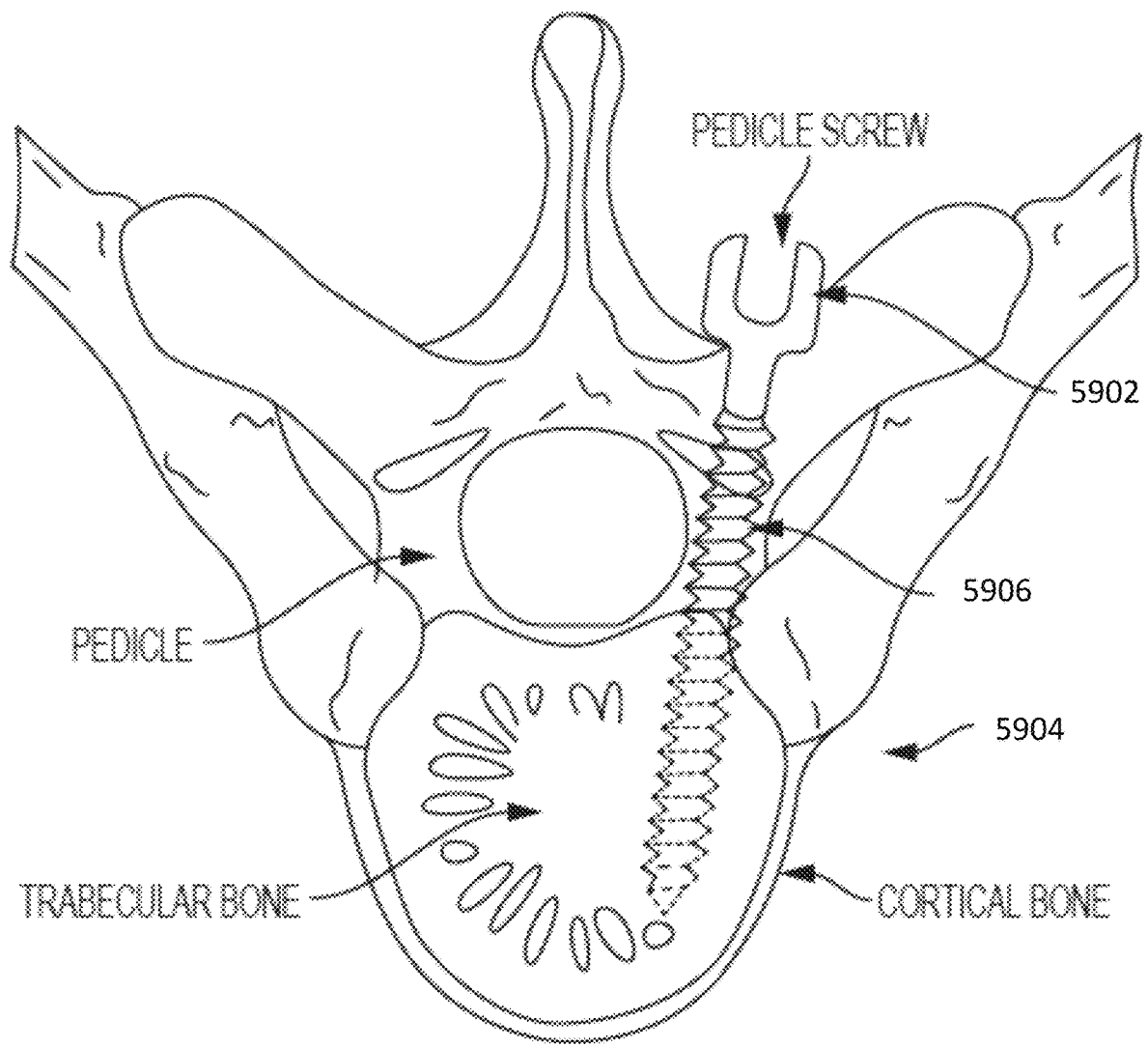
FIG. 59 depicts a pedicle screw procedure in accordance with one embodiment of the present disclosure.

While the device 10 may be used in conjunction with other procedures and to detect other characteristics of bone, application of the device 10 for a pedicle screw fixation procedure is described herein. This type of procedure requires the introduction of a screw 5902 into the vertebral body 5904 through the pedicle 5906, as shown in FIG. 59. Typically, the screw 5902 is advanced ventrally between 70% and 80% of the anterior-posterior diameter of the vertebral body 5904. Undesirable effects may result through excessive forward advancement of the screw 5902, which would result in an undesired penetration of the distal ventral cortex (outer cortex perforation). Also, the pedicle 5906 may deform or fracture if a thick screw 5902 is inserted into the pedicle. Further, proximal injury of the inner cortex perforation or lateral pedicle wall perforation can occur with excessive medial or lateral angulation of the screw 5902 with damage to the spinal cord or to the spinal nerve root.

To address these concerns, the device 10 may be used to perform at least the following functions: (1) determine the structure and physical characteristics of the bone (e.g., bone density, bone histology, the presence of any degeneration or disease, presence and quantity of any fluid, and composition of any cartilage; (2) identify a screw entry target site, which is the entry site of the screw 5902 on the surface of the vertebral body 5904, based on the bone characteristics; (3) recommend the diameter and length of the screw or implant; and (4) identify a screw pathway that extends from the exterior of the vertebral body 5904, through the pedicle, and into the trabecular bone.

With respect to functions (1) and (2), the device 10 may use the classifier to assess or characterize the type of bone, the density of the bone, and the type of bone, and make an assessment based on predetermined parameters, such as impedance and attenuation, to assess whether the bone is a good candidate for cannulation into the pedicle via a pedicle screw or other device (Jamshidi, spinal needle, k-wire). With regard to function (3), the device 10, based on an ultrasound survey of the vertebral body 5904, can recommend the length of the pedicle screw 5902 and the recommended diameter of the screw 5902. The specifications of the screw 5902 may depend on the geometry and density of the pedicle, thickness density of the cortical bone, and the length of the pedicle, for example. With respect to function (4), the device 10 and accompanying software may project the desired screw pathway and display the pathway via an attached monitor. The pathway may largely depend on the factors discussed above with respect to functions (1), (2), and (3) and also include the thickness of the trabecular bone and overall geometry of the vertebral body 5904.

In other aspects, a start point of the pedicle screw may need to be drilled in order to expose the inner cancellous bone, thereby giving contrast to the surrounding cortical bone similar to what is done intraoperatively. The device 10 may also create a circle representing the pedicle outer margins and the surgeon may then cannulate through the circle, ensuring a safe passage around the spinal canal into the vertebral body. Currently this is done via tactile feedback (cortical vs. cancellous bone as the surgeon pushes a gear shift) versus adjunct intraoperative fluoroscopic guidance (radiation exposure to the surgeon). Furthermore, the pedicle may be viewed as a cylinder of safe bone with the outer part of the cylinder being the cortical bone. The device 10 may allow the surgeon to see a circle, for example on an attached monitor, and may cannulate the circle. Outside of the medial part of the circle may be the spinal canal, outside of the lateral part may be outside the pedicle. By staying within the middle of the circle, the surgeon may be able to get into the vertebral body safely and the screw may be as long as the surgeon can make it until he/she sees cortical bone again (representing the anterior vertebral body). Staying within the medial part of the circle, e.g., in the cancellous bone, may be done by detecting the different properties of different bone based on the specific impedance and attenuation characteristics that are specific to the different types of bone.

Typically, the diameter of the pedicles range from 5-12 mm, and the cylinder may be approximately from 30-50 mm in length with the bad/critical depth occurring at 20 mm (that is the point where the medial wall of the pedicle is in contact with the spinal canal).

Steps for identifying the ideal placement of a pedicle screw are now described. First, the device 10 may scan the surface interface between soft tissue and bone. The signal reflected from this interface may be detected by quantifying the large specular reflection from the surface. The envelope of the signal just past the specular reflector may be characterized using an exponential decay function to estimate an attenuation coefficient of the bone. Bone will have high attenuation and it may be expected that the ultrasound will not propagate far into bone.

Next, the attenuation coefficient and the impedance value may be combined into a single classifier parameter to uniquely identify the bone surface as cortical or cancellous. In some embodiments, the ultrasonic array may rotate azimuthally about the bone surface to create a cylindrical image volume. From this cylindrical volume, the location of the cortical and cancellous bone may be visualized with respect to the imaging probe.

Using quantitative ultrasound technique, the system may create multiple (at least 2) shaped perimeter images, for example on an attached display, of a perpendicular plane that exists along the outer edge of the cancellous bone, where the cancellous bone and cortical bone meet within the pedicle itself. This may be done by noting the contrast of cortical bone and cancellous bone and mapping this contrast at different planes within the pedicle. Using a shape algorithm, the system may highlight the perimeter of where this contrast exists, creating a shaped perimeter.

These shaped perimeters may be created in perpendicular planes at varying distances away from the ultrasound transducer. For example, one shape perimeter image may be proximal to the probe at approximately 1 mm away, while a following perimeter image may be created at 4-5 mm and then another at 8-10 mm.

Then, the ultrasound transducer may then be able to be positioned by the user by changing the angle of the tube or surgical transducer tool. When all of the shaped perimeters at varying distances are lined up, such that a line can be drawn through them on the user interface, the correct trajectory for pedicle screw placement will have been determined.

Figure 60:
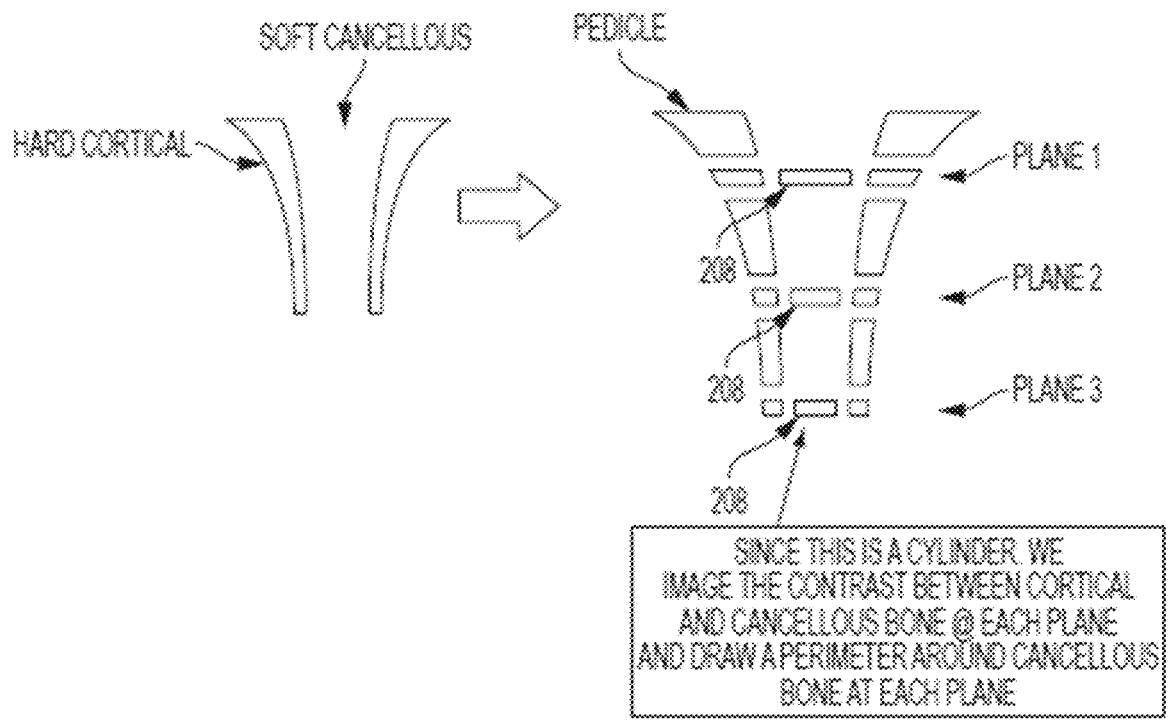
FIG. 60 is one embodiment of the device used to place a screw within the pedicle using the present invention.
Figure 60:
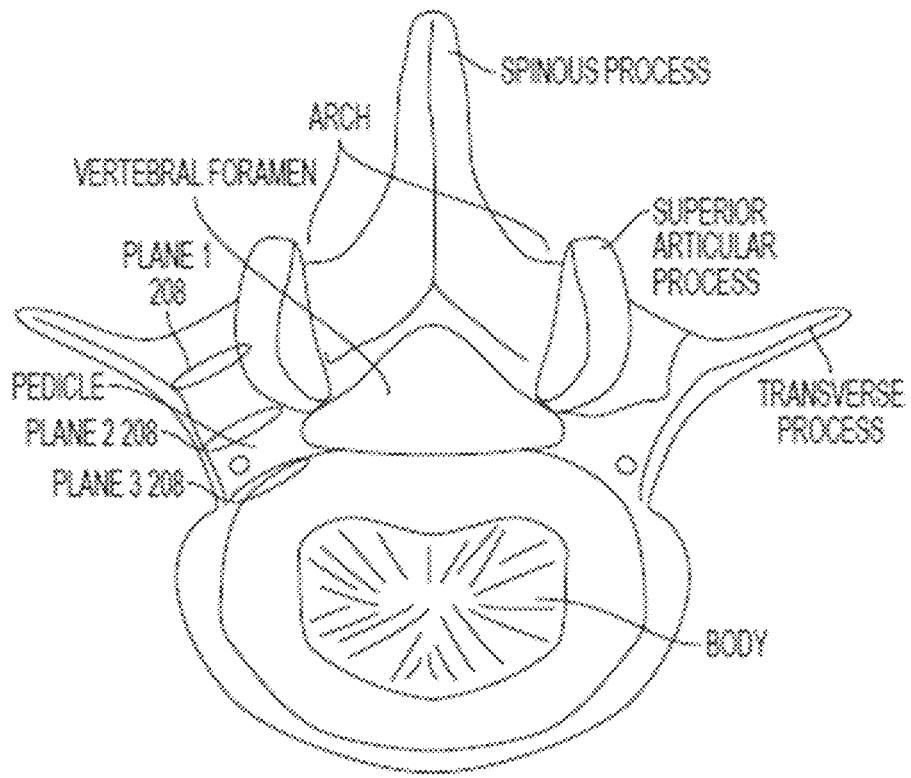

In some embodiments, the system may provide a drilling guide that may enable the safe placement of a pedicle screw into the cancellous bone. As shown in FIG. 60, device 10 may assess which portions of the bone are cancellous and cortical and may also determine the cross-sectional plane 208 depicting the boundaries between the cortical and cancellous bone. Thus, the system may calculate the regions of cancellous bone along the length of the pedicle. The plane 208 may be viewed as a cross sectional plane of the pedicle and is generally circular in nature because the cancellous bone resides within the cortical bone. The plane 208 can be taken along the length of the pedicle so as to allow a visual representation of where the planes 208 are (e.g. planes 1, 2, and 3 of FIG. 60 and planes 5 in FIGS. 61-62).

After assessing the cross-sectional planes 208 along the length of the pedicle, the system may determine a proposed screw trajectory that allows for the safe placement of the screw through the pedicle where the screw resides entirely within the cancellous bone. One way to determine the proposed screw trajectory is by aligning one or more planes 208, which will indicate that there is a path between planes that is free of cortical bone. Stated differently, the portion of the planes 208 that are aligned (i.e., overlap) with one another is the portion where only cancellous bone resides between those planes. The alignment of the planes 208 may be adjusted by articulating the device 10. The surgeon may adjust the device 10 until a sufficient overlap between the planes 208 is determined, which may be represented by the percentage of overlap, for example. Once the sufficient amount of overlap is determined, the surgeon may mark the position of the device 10 as the drill trajectory.

Figure 61:
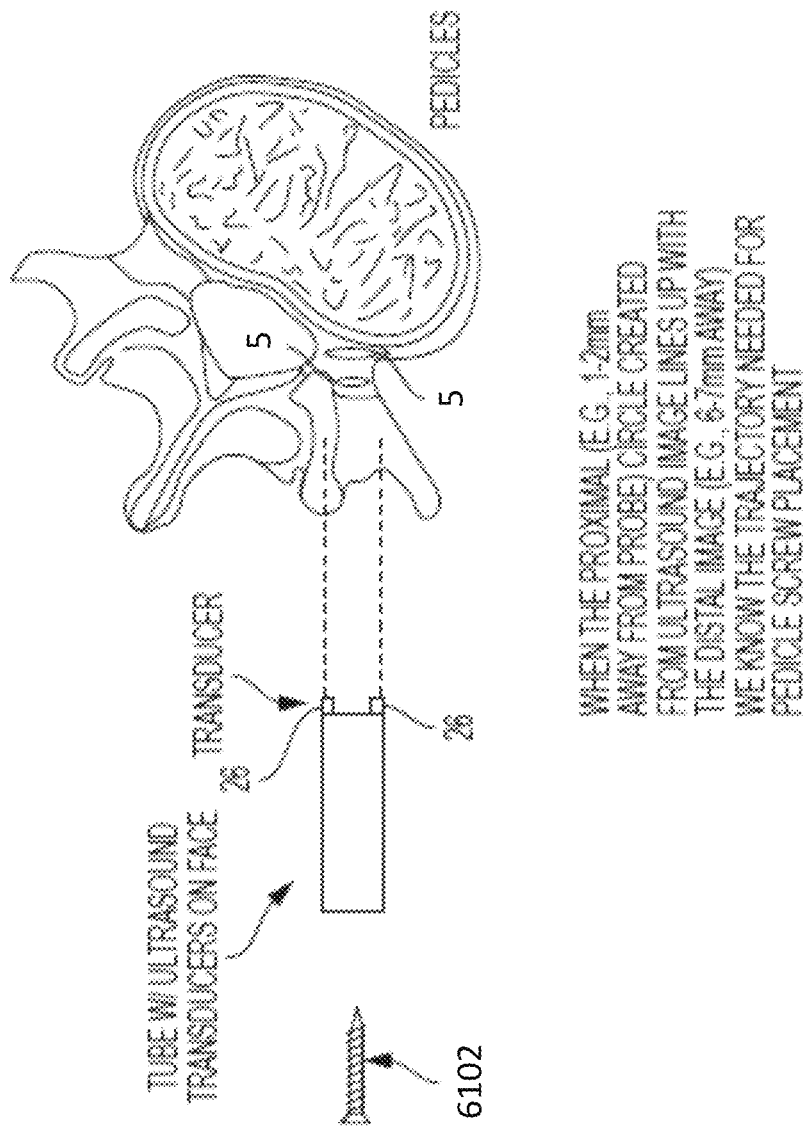
FIG. 61 is another embodiment of the device used to place a screw in the pedicle using the present invention.

As shown in FIG. 61, the device 10 may also be used to place the screw 6102 within the pedicle. In this embodiment, the transducers 26 may be placed on either side of the distal end of the device 10 so as to allow the screw 6102 to be retained between the transducers 26. The device 10 may have a hollow cannula so as to allow the screw 6102 to be passed through the device 10 such that the surgeon need not move the device 10, once the ideal drill trajectory is determined, for example the path through planes 5.

Figure 62:
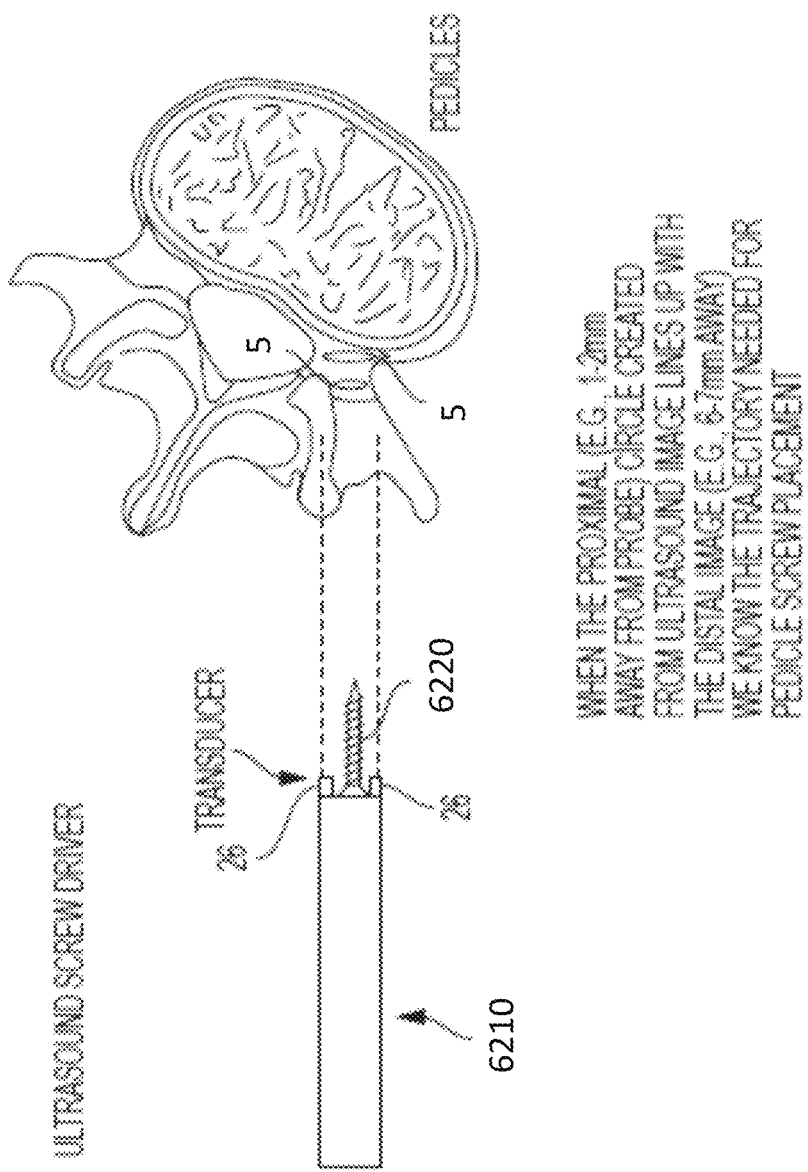
FIG. 62 is another embodiment of the device used to place a screw in the pedicle as disclosed in FIG. 61.

In another embodiment, as shown in FIG. 62, a driver 6210 may be positioned within the anatomy to insert the screw 6220 through the pedicle. In this embodiment, the driver 6210 may also include transducers 26 so to allow for confirmation that the drill trajectory has not changed during the drilling process.

It is also contemplated that the device 10 for the pedicle screw fixation procedure may be attached to a robotic assembly so as to automate at least part of the process and/or allow the surgeon control the procedure remotely. For example, the calculation of the ideal drill trajectory may be automated based on minimum threshold parameters based on the size and length of the screw, health of the bone, and other anatomical characteristics.

In some embodiments, the robotic arm may move the probe to avoid contact with undesirable structures (e.g., nerve). In some embodiments, it may use a pre-determined map of the anatomy and direct the robotic arm to penetrate through the nerve free area. In the event the probe is adjacent to a portion of the anatomy that is to be avoided, the robotic system may be used to automatically re-position, for example based on artificial intelligence created by the algorithm that told it to move left/right, etc. based on nerve location and the quickest path to the destination. In some embodiments, the robotic system may conduct two procedures simultaneously, such as, for example, one robot arm may push device 10 down first to sit atop the psoas and map the underlying anatomy, while the other robotic arm may push the probe through to arrive at the spinal canal/vertebra.

Examples of robotic systems to which the present invention may be coupled with include U.S. Pat. Nos. 8,010,181; 8,219,177; and 8,219,178, each of which is incorporated by reference herein in its entirety.

Figure 21:
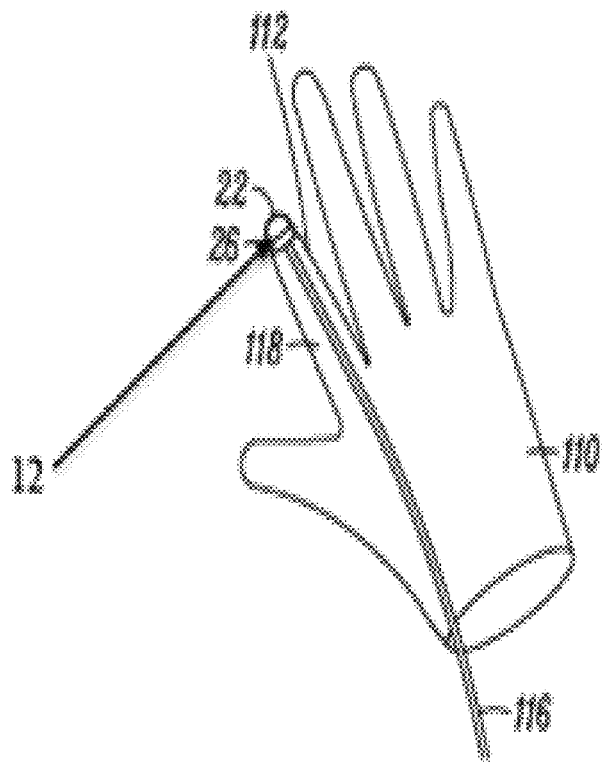
FIG. 21 is one embodiment of the present disclosure that is incorporated into a glove.

In another embodiment, shown in FIG. 21, an ultrasound imager 24 may be used in conjunction with a glove 110. In this embodiment, the operator may rely on tactile feedback provided by touch while still enabling ultrasonic imagining/ scanning of a patient's anatomy. More specifically, the glove system (or device) may allow for tactile feedback that facilitates the dissection and separation of tissue namely neurological, vascular and peritoneal structures. In general, tactile feedback allows for dissection of tissue in normal surgical procedures without the unique perspective of direct visualization that may not be permissible in some minimally invasive/percutaneous techniques.

Figure 22:
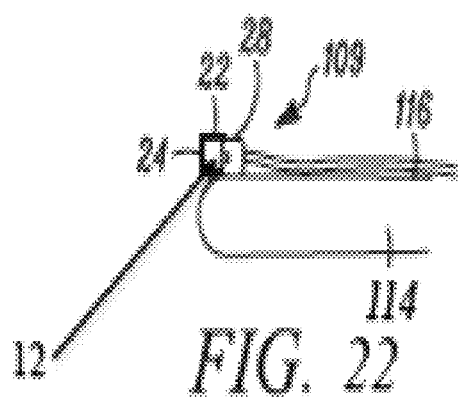
FIG. 22 is a partial side view of the embodiment disclosed in FIG. 21.

The ultrasound imager 24 may include a transducer 26 that is configured to emit sound waves may be disposed at the distal end of the glove 110. In one embodiment, the transducer 26 is located along a distal portion 114 of the index finger 112 of the glove 110. As better shown in FIG. 22, a tip 22 forms part of, or is connected to, the distal portion 114 of the index finger 112 such that the outer surface of the tip 22 does not extend beyond the very most distal part of the index finger 112. Of course, it is appreciated that the tip 22 may extend beyond the distal portion depending on the embodiment.

Connected to the transducer 26 may be a flexible conduit 116 that may carry a cable that connects the transducer 26 to a housing that contains the remaining portion of the ultrasound imager 24. The flexible conduit 116 may run along the length of the index finger 112 and a top portion 118 of the glove 110. However, it can be appreciated that the conduit 116 can run along any length or surface of the glove 110 and is application dependent. The flexible conduit 116 may also provide a channel to carry a k-wire or other instrument that can be slidingly disposed within the flexible conduit 116 (as will be further discussed below). The flexible conduit 116 may run through and may be in communication with a unit 109 such that a portion of the flexible conduit 116 provides an opening 120, as shown in FIG. 23, in the unit 109 at the distal portion 114 of the index finger 112.

Figure 23:
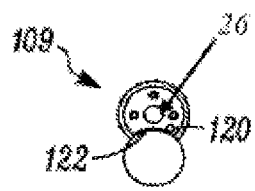
FIG. 23 is a front cross-sectional view of one embodiment of the glove embodiment disclosed in FIG. 21.
Figure 24:
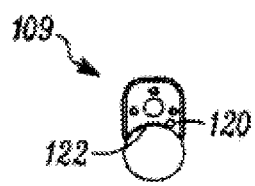
FIG. 24 is a front cross-sectional view of another embodiment of the glove embodiment disclosed in FIG. 21.
Figure 25:
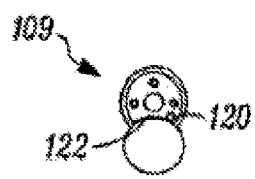
FIG. 25 is a front cross-sectional view of yet another embodiment of the glove embodiment disclosed in FIG. 21.

The unit 109 may have a bottom portion 122, as shown in FIG. 23. The bottom portion 122 may have a concave curvature so as to provide a complimentary fit once an operator's hand is placed within the glove 110. In addition, a proximal portion of the unit 109 may have a taper so as to cause minimal disruption to a patient's anatomy as the unit 109 is articulated during a procedure. Further, the unit 109 may have an overall semi-circular or cylindrical shape or the like so as to minimize any inadvertent disruption to the patient's anatomy during a procedure and to maintain a small overall profile as shown in FIGS. 24 and 25. For example, the height of the unit 109 may be less than the overall width to as to achieve a low profile. Alternatively, the outer portion of the unit 109 may not extend beyond and become collinear with the width of the index finger 112 to maintain a low profile. The external outer diameter of the unit 109 may range from 0.5 to 20 mm and outside of this range depending on the desired application. The length of the unit 109 can range from 0.5 to 10 mm but also may fall outside of this range depending on the application. It is appreciated that more than one transducer 26 may be positioned along the distal portion of a finger such that they provide side facing scans to generate a multi-directional (e.g. 180°-300°) scan of the patient's anatomy.

Transducers 26 may be side positioned (e.g. on either side of the index finger 112) so as to provide for multi-directional scanning of the patient's anatomy to detect the nerve or target anatomy. The side positioned transducers may be configured to scan the anatomy around in a circumferential direction around the index finger 112 to detect the nerve (or other target anatomy) not detected by the transducer positioned at the distal end of the main body 16. The multi-directional scanning may enable the system to generate a scan image of the patient's anatomy in multiple directions as the index finger 112 of the glove 110 is advanced through the patient's anatomy. As discussed above, the system that is in communication with the transducers may then detect the nerve even that is not captured by the forward scanning transducer.

The image capture system 200, as discussed in relation to FIGS. 29 and 30, may be used with the glove embodiment where the image capture device 201, its tip 22, sensor 206, and illumination device 216 may be placed on a distal portion 114 of the index finger 112 of the glove 110. The image capture system 200 may also be used independently of, or in conjunction with, the ultrasound imager 24 as described above in the glove embodiments.

The glove embodiment can be used in connection with minimally invasive surgery (MIS). The glove 110 may be used for a variety of MIS procedures, including but not limited to, Lateral Retroperitoneal Interbody Fusion (LLIF (e.g., eXtreme Lateral Lumbar Interbody Fusion (XLIF), Direct Lateral Interbody Fusion (DLIF)), Axial Lumbar Interbody Fusion (AxiaLif), Transforaminal Lumbar Interbody Fusion (TLIF), Posterior Lumbar Interbody Fusion (PLIF), Anterior Lumbar Interbody Fusion, Trans-thoracic lumbar interbody fusion, Retropleural Thoracic Fusion, Interbody Fusion utilizing Kambin's Triangle, and Cervical/ Thoracic/Lumbar Laminectomies, Foraminotomies and Diskectomies. The glove 110 may be used to confirm that the area is clear of other anatomical parts, such as blood vessels, abdominal/pelvic viscera, nerve roots, and spinal cord.

As described above, there can be a number of applications for which this glove 110 may be used, which may require similar steps to access the surgical site. The surgeon may rely on the image or audio queues generated by the ultrasound imager 24 to detect the presence (or absence) of a nerve thereby allowing the surgery to reposition (or continue advancing) the glove 110 through the patient's anatomy towards the surgical site 46.

Once the muscles are split and the surgical site 46 is reached, the surgeon can place a k-wire through the conduit to confirm that the surgical site 46 is reached and anchor the glove 110 with respect to the surgical site 46. A retractor tool is put into place to give the surgeon a direct surgical working conduit to the surgical site 46. Alternatively, a series of dilators may be sequentially placed over the k-wire to create the working space. Once this direct access to the spine is achieved, the surgeon is able to perform a standard discectomy (removing the intervertebral disc), corpectomy (removing the vertebral bone) or fusion (uniting two bones together) with surgical tools.

In the case of a discectomy, after the disc material is removed, the surgeon may be able to insert an implant/ spacer through the same incision from the side. This spacer (cage) will help hold the vertebrae in the proper position to make sure that the disc height (space between adjacent vertebral bodies) is correct and to make sure the spine is properly aligned. This spacer, together with a bone graft, may be designed to set up an optimal environment to allow the spine to fuse at that particular segment. The surgeon may use fluoroscopy to make sure that the spacer is in the right position. The surgeon may then remove the refractor and suture the incisions.

The glove system may also be used for performing an axial lumbar interbody fusion (AxiaLIF). At surgery, the patient may be positioned prone with maintenance of lordosis and the legs spread. A catheter may be inserted into the rectum will allow air to be injected during the procedure for visualization of the rectum. After the surgeon makes a small incision (15-18 mm) lateral to the tip of the coccyx, the distal portion of the index finger 112 and distal tip 22 is inserted through the incision and is passed into the pre-sacral space. The surgeon may use the index finger 112 to sweep and inspect the pre-sacral space to confirm that the space is clear of any offending anatomy (e.g. colon, rectum) visually and by way of ultrasonic imaging. The index finger 112 may be advanced along the anterior cortex of the sacrum and in the midline to an entry point usually close to the S1-2 junction. Once the trajectory is chosen, a sharp beveled pin may then be driven into the L5-S1 interspace, either through a conduit or after the retractor system is deployed. The retractor system 48 or 6300, or a series of dilators, may be used to create approximately a 10 mm opening into the sacrum through which a 10 mm channel is drilled into the L5-S1 disc. The index finger 112 may then be withdrawn from the pre-sacral space and the surgeon may then perform the remaining steps of the AxiaLIF procedure.

The glove system may also be used to allow direct access to Kambin's triangle (Extraforminal interbody fusion). For this procedure, patients may be placed in the prone position typically onto a Jackson Table using a radiolucent frame that allows for restoration of lumbar lordosis. Fluoroscopic imaging may be utilized to identify the epiphyseal plate of the upper and lower vertebral body by controlling the cranial-caudal angle of the image intensifier. Additionally, the fluoroscopic image may be rotated by 20-35 degrees toward the region, so that the superior articular process can be seen at the middle of the intervertebral disc. At this location, the index finger 112 can be inserted percutaneously targeting the area commonly referred to as Kambin's triangle. As discussed above, Kambin's triangle is defined as the area over the dorsolateral disc. The hypotenuse is the exiting nerve root, the base (width) is the superior border of the caudal vertebra and the height is the dura/traversing nerve root.

The glove system may be used to identify various anatomical features such as the exiting root, radicular artery, thecal sac and the disc space. A k-wire can then be place into the disc space via the conduit under ultrasonic visualization allowing for docking of the dissector/retractor system. Subsequent dilation can then be performed allowing for access in the intervertebral foramen while directly visualizing neurovascular structures using the device and avoiding these structures when identified by the surgeon.

The device 10 may also include infrared technology, which includes an infrared emitting light source and an infrared image capture device. The device 10 may include one or more infrared radiation detecting elements mounted at the distal portion 14 of the device 10. The infrared array may be sensitive at e.g. wavelengths from 2 to 14 micrometers. One embodiment of the infrared aspect of the present disclosure uses a two-dimensional array of microbolometer sensor elements packaged in an integrated vacuum package and co-located with readout electronics on the distal tip of the device 10. It is appreciated that the infrared aspect of this disclosure may be used in conjunction with, or separate from, the other embodiments discussed herein. One such infrared system that could be used with the present disclosure is disclosed in U.S. Pat. No. 6,652,452, the entirety of which is incorporated herein by reference.

The device 10 may also utilize Optical Coherence Tomography (hereinafter "OCT") technology as a stand-alone detection system or in conjunction with the other embodiments disclosed herein. OCT is an optical signal acquisition and processing method that generates images using near infrared light. By way of background, OCT performs high-resolution, cross-sectional tomographic imaging of the internal microstructure in materials and biologic systems by measuring backscattered or back-reflected light. OCT images are typically two- or three-dimensional data sets that represent the optical back-scattering in a cross-sectional plane through the tissue. Image resolutions of approximately 1 to 15 micrometers may be achieved, one to two orders of magnitude higher than conventional ultrasound. Imaging can be performed in situ and in real time.

Figure 26:
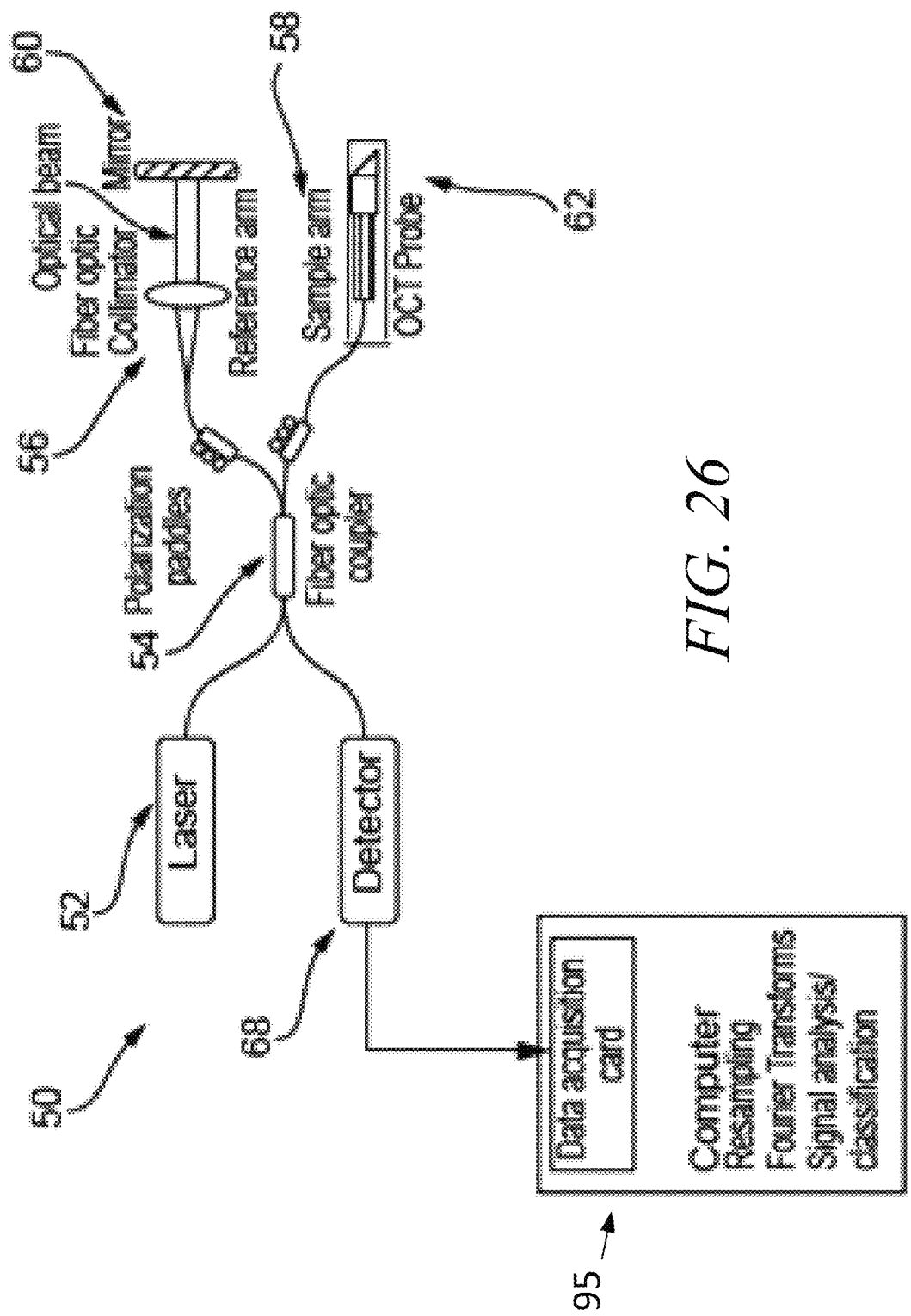
FIG. 26 is diagram of another embodiment of the present disclosure that utilizes Optical Coherence Tomography.

OCT forms depth resolved images by interferometrically detecting the light backscattered from different scatterers within the sample. In a typical OCT system 50, as shown in FIG. 26, the light from the laser 52 is split by a fiber optic coupler/beam splitter 54 into two arms i.e. the reference arm 56 and the sample arm 58. The light coupled into the reference arm 56 is reflected back from a fixed mirror 60, while in the sample arm 58 the light is projected through an OCT probe 62, which will be discussed in greater detail below.

The OCT probe 62 may be focused onto the sample of interest (e.g. tissue or the anatomy of the patient) through a focusing lens (e.g. a GRIN lens). OCT is a point by point imaging technique where the sample is illuminated by focusing the light from the laser 52 onto a small point (spot size determined by the focusing lens) on the sample. Light in the sample arm 58 travels within the tissue and is backscattered by different scatterers within the tissue and combines with the light from the reference arm 56. If the optical path lengths of the reference 56 and sample 58 arms are matched, an interferogram may be formed which may be measured by a photo detector or a spectrometer. The frequency content of the interferogram may contain information about the depth and strength of the scatterers that the beam had encountered in the sample. The resulting interferogram may be processed to form one-dimensional depth information generally known as an A-scan (a single A-scan would be a single column in the image). The optical beam may then be scanned over the sample to generate two- or three-dimensional images. The beam may be scanned using galvanometers in bench-top OCT systems or using MEMS scanners in hand-held OCT devices. This data is sent to, and processed by, the computer 95 or other processor.

Figure 27:
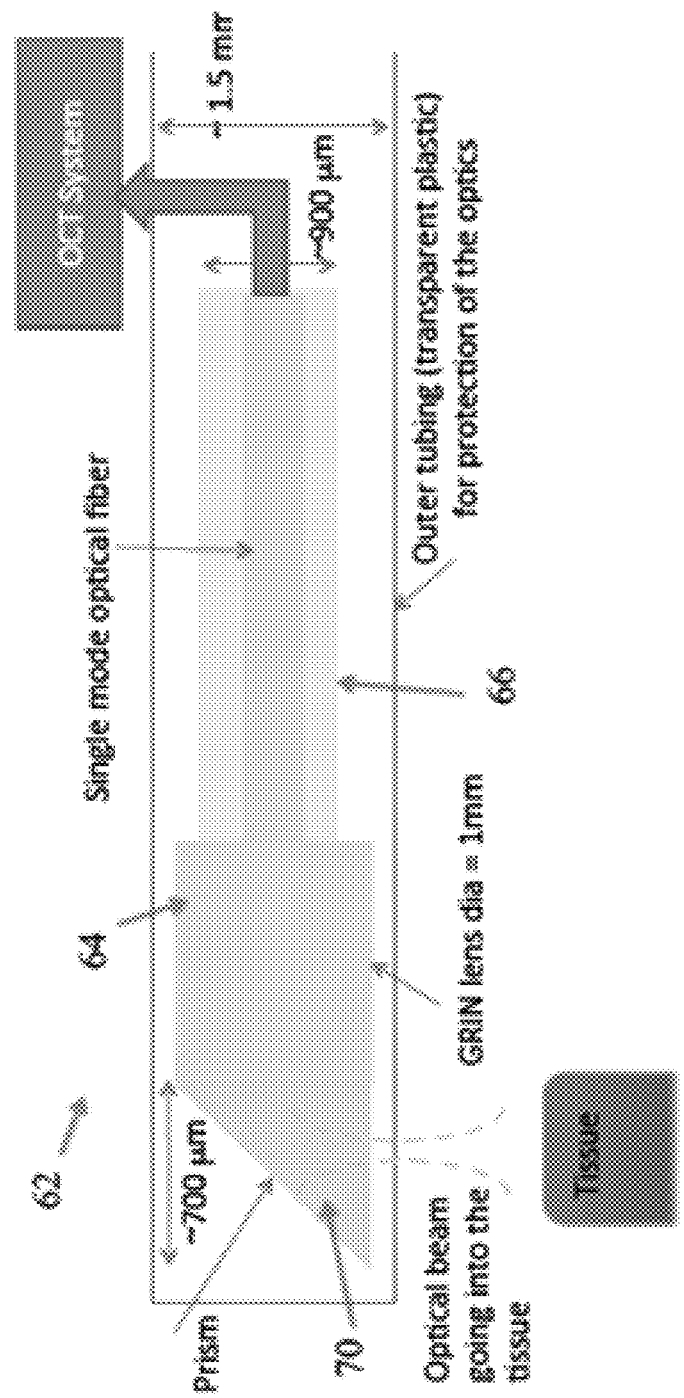
FIG. 27 is one embodiment the probe used with the embodiment disclosed in FIG. 26.

As further disclosed in FIG. 27, the OCT probe 62 may include a GRINS lens 64, the diameter of which in this embodiment is 1 mm, but which can vary depending on the intended application. A single mode optical fiber 66 is included in this embodiment that transfers the light rays between the OCT probe 62 and the remaining portion of the OCT system (e.g. the fiber optic coupler 54 or a detector 68). The single mode optical fiber 66 may have a thickness of approximately 900 micrometers and a length of approximately 1.5 m. These specifications, of course, are examples only and can vary depending on the application. Attached to the distal end of the GRINS lens 64 may be a prism 70 for deflecting the light depending on the location and orientation of the target. It can be appreciated that the prism 70 may not be necessary in situations where the surface of the target is directly in front of or substantially perpendicular to the longitudinal axis of the light ray (or beam). In this embodiment, the length of the prism is approximately 700 micrometers, but it is appreciated that the length can vary and is application dependent.

Figure 28:
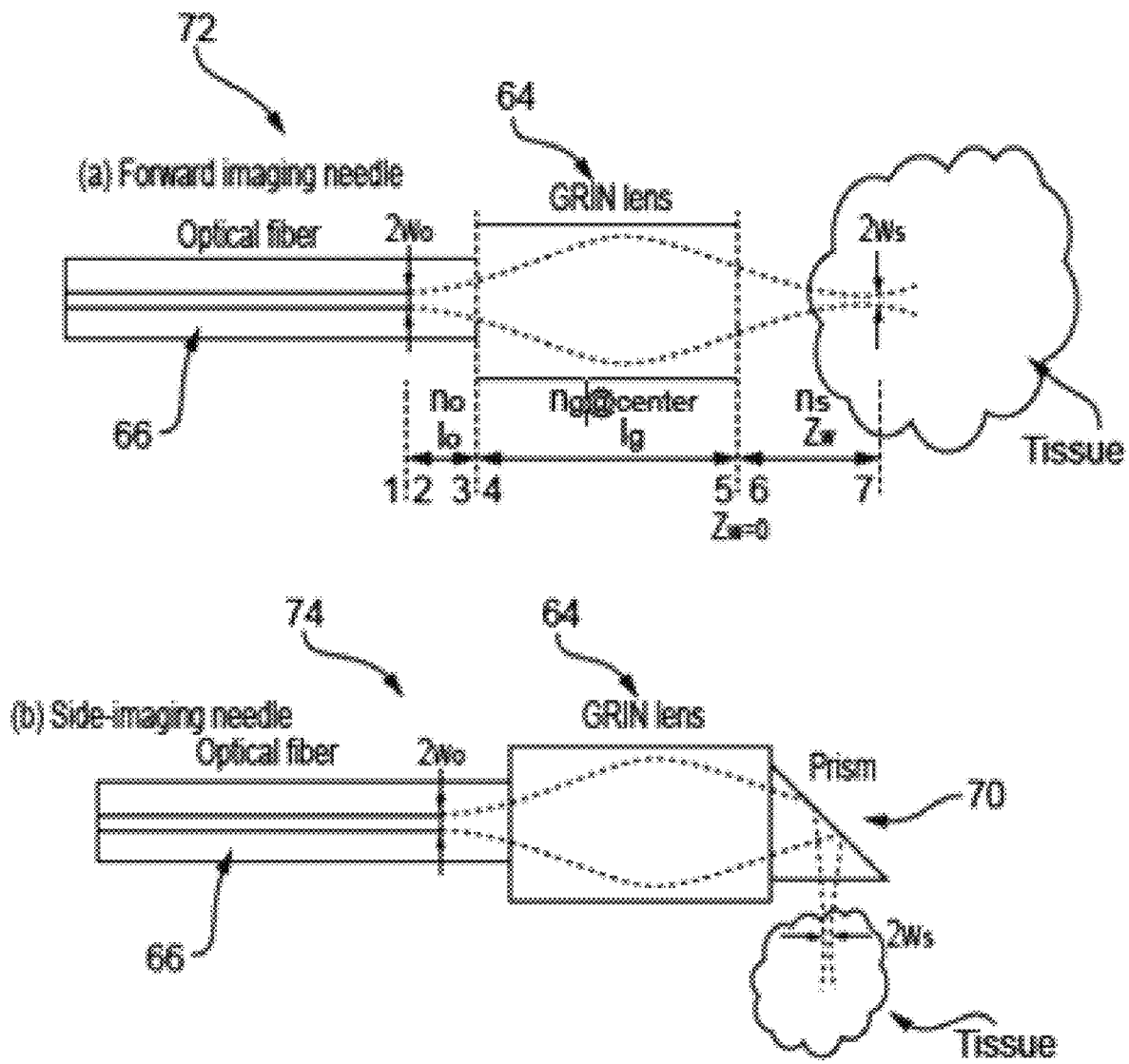
FIG. 28 depicts two embodiments of the probe used with the embodiment disclosed in FIG. 26.

Two different embodiments of the OCT probe 62 are illustrated in FIG. 28. The first embodiment is the forward image probe 72, which does not include a prism, such that the light ray (or beam) extends outward towards the front of the probe 72 to reach the target (e.g. tissue). In the second embodiment, image probe 74 contains a prism 70, which allows this embodiment to image targets that are disposed below or at an angle to the tip of the probe 74. The OCT technology may also be incorporated in to the glove 110 in a manner as discussed above with respect to the ultrasound embodiment.

Some of the parameters that may be manipulated to optimize OCT imaging include (a) the A-scan rate (the number of A-scans the system can acquire in a second), (b) the axial and transverse resolution, and (c) the imaging depth. The A-line scan rate may determine how fast an OCT system can operate. For a swept source OCT system, the imaging rate may depend on the wavelength sweeping rate of the laser, while, for a spectral domain OCT system, it is generally limited by the speed of the line scan camera used in the spectrometer. The tradeoff is that at a higher A-scan rate, the exposure time has to be reduced which can decrease the SNR of the acquired data. The axial resolution (resolution across the depth) is determined by the bandwidth and wavelength of the laser source. In general, the higher the bandwidth the better is the axial resolution. The resolution along the transverse dimensions is determined by the numerical aperture of the lens in the sample arm 58. The higher the numerical aperture, higher the transverse resolution, however, the tradeoff is a reduced depth-of-field. Moreover, with an increase in the center wavelength of the source both the axial and transverse resolutions degrade. Finally, the imaging depth is usually limited by how deeply the light can penetrate through the tissue or sample of interest. Higher wavelengths offer greater imaging depth. These and other parameters may be optimized to detect certain features of a patient's anatomy, such as nerve root.

The OCT probe 62 may be positioned at the distal portion 14 of the device 10. Alternatively, the OCT probe 62 may be positioned at the distal end of a k-wire like structure and disposed through the conduit 36. In either embodiment, the OCT probe 62 may be configured to image a portion of the patient's anatomy that is adjacent to (or in front of) the distal portion 14 of the device 10. The surgeon may insert the OCT probe 62 to image the patient's anatomy as needed to reach the surgical site. The OCT system 50 may be configured to visually and/or audibly indicate detection of select preselected portions of a patient's anatomy (e.g. nerve root). As mentioned above, it can be appreciated that the OCT system can be used independently or in combination with other detection technologies described herein.

It is also contemplated that the device 10 can be used in conjunction with a neuromonitoring system to detect certain portions of a patient's anatomy, including neural elements that include a nerve, nerve bundle, or nerve root. For the purposes of this discussion, the device 10 and neuromonitoring system will be discussed with respect to detecting a patient's spinal nerve but it is contemplated that the device 10 and neuromonitoring system may be used to detect other nerves (peripheral and central) as well as the spinal cord. One type of neuromonitoring system that may be used in conjunction with the device 10 is disclosed in U.S. Pat. No. 7,920,922, the entirety of which is incorporated by reference herein.

In one embodiment, stimulation electrodes may be placed at the distal end of the device 10, such as forming part of the tip 22, or placed at a distal end of an instrument, such as a K-wire, disposed through the conduit 36, to stimulate any nerves in the region adjacent to the distal portion 14 of the device 10. EMG (electromyography) electrodes can be placed on the skin to detect any nerve depolarization in the manner descried in U.S. Pat. No. 7,920,922. One manner in which the proximity, location, direction, physiology of the nerve is determined is also disclosed in U.S. Pat. No. 7,920,922. It is appreciated that other techniques of detecting nerves using stimulation are known in the art and any of those techniques may be used in conjunction, or integrated, with the device 10 in the manner described above.

The ultrasound imager 24 may be used in conjunction or independent of an image capture device to visualize the patient's anatomy as described herein. Steps and methods describe herein using the ultrasound imager 24 to detect certain features of a patient's anatomy may be supplemented through use of an image capture device. Specifically, the surgeon may rely on the image or audio queues generated by the ultrasound imager 24 to detect the presence (or absence) of a nerve thereby allowing the surgery to reposition (or continue advancing) the device 10 through the patient's anatomy towards the surgical site 46. The ultrasound imager 24 may also be used to confirm the image captured by the image capture device is accurate by confirming the presence or absence of a targeted anatomical feature (e.g. nerve).

Likewise, in operation, the OCT system 50 may be used in conjunction or independent of an image capture device and/or the ultrasound imager 24 to scan and identify the patient's anatomy as described herein and to access the surgical site. Steps and methods used to access the surgical site and avoid target anatomy (e.g. nerve) employing the ultrasound imager 24 may also be performed using the OCT system 50. Furthermore, steps described herein using ultrasound imager 24 may be supplemented through use of the OCT system 50. For example, the surgeon may rely on the image or audio cues generated by the OCT system 50 to detect the presence (or absence) of a nerve thereby allowing the surgery to reposition (or continue advancing) the device 10 through the patient's anatomy towards the surgical site 46. The OCT system 50 may also be used to confirm the image captured by an image capture device is accurate by confirming the presence or absence of a targeted anatomical feature (e.g. nerve).

The device 10 may be used in a variety of other medical areas outside of spinal surgery. These include: gynecologic transvaginal imaging for cervical cancer and endometrial cancer, prostate examination/prostate cancer, intra-abdominal surgery to delineate depth of penetration of a tumor within peritoneal contents (stomach, small intestine, large intestine, kidney, liver, and spleen). The device 10 may be utilized with known robotic systems, such as the Da Vinci Robotic or similar systems.

Figure 47:
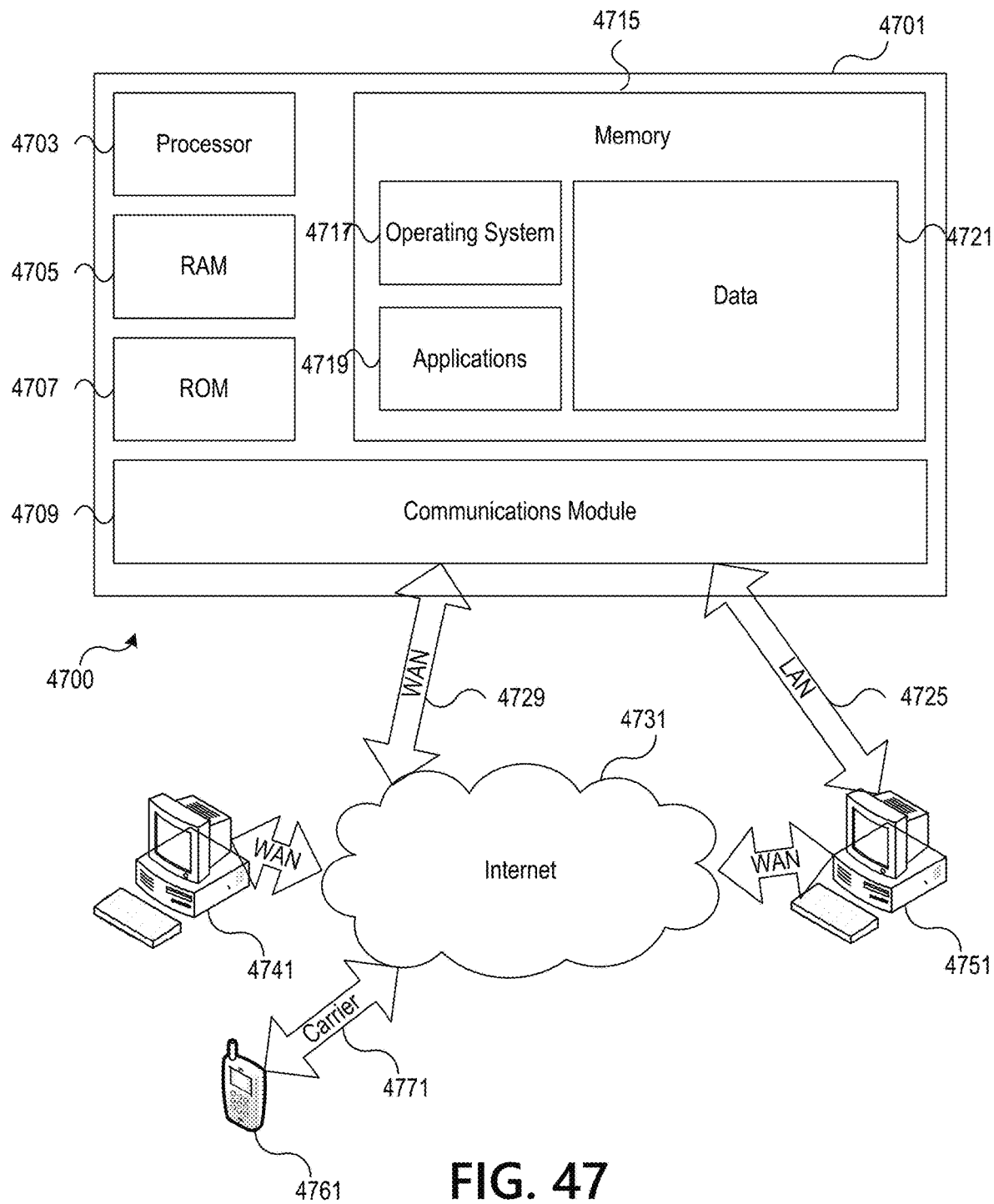
FIG. 47 illustrates a computing device in accordance with one or more aspects described herein.

FIG. 47 depicts an illustrative operating environment in which various aspects of the present disclosure may be implemented in accordance with one or more example embodiments. Referring to FIG. 47, computing system environment 4700 may be used according to one or more illustrative embodiments. Computing system environment 4700 is only one example of a suitable computing environment and is not intended to suggest any limitation as to the scope of use or functionality contained in the disclosure. Computing system environment 4700 should not be interpreted as having any dependency or requirement relating to any one or combination of components shown in illustrative computing system environment 4700.

Computing system environment 4700 may include computing device 4701 having processor 4703 for controlling overall operation of computing device 4701 and its associated components, including random-access memory (RAM) 4705, read-only memory (ROM) 4707, communications module 4709, and memory 4715. Computing device 4701 may include a variety of computer readable media. Computer readable media may be any available media that may be accessed by computing device 4701, may be non-transitory, and may include volatile and nonvolatile, removable and non-removable media implemented in any method or technology for storage of information such as computer-readable instructions, object code, data structures, program modules, or other data. Examples of computer readable media may include random access memory (RAM), read only memory (ROM), electronically erasable programmable read only memory (EEPROM), flash memory or other memory technology, compact disk read-only memory (CD-ROM), digital versatile disks (DVD) or other optical disk storage, magnetic cassettes, magnetic tape, magnetic disk storage or other magnetic storage devices, or any other medium that can be used to store the desired information and that can be accessed by computing device 4701.

Although not required, various aspects described herein may be embodied as a method, a data processing system, or as a computer-readable medium storing computer-executable instructions. For example, a computer-readable medium storing instructions to cause a processor to perform steps of a method in accordance with aspects of the disclosed embodiments is contemplated. For example, aspects of the method steps disclosed herein may be executed on a processor on computing device 4701. Such a processor may execute computer-executable instructions stored on a computer-readable medium.

Software may be stored within memory 4715 and/or storage to provide instructions to processor 4703 for enabling computing device 4701 to perform various functions. For example, memory 4715 may store software used by computing device 4701, such as operating system 4717, application programs 4719, and associated database 4721. Also, some or all of the computer executable instructions for computing device 4701 may be embodied in hardware or firmware. Although not shown, RAM 4705 may include one or more applications representing the application data stored in RAM 4705 while computing device 4701 is on and corresponding software applications (e.g., software tasks) are running on computing device 4701.

Communications module 4709 may include a microphone, keypad, touch screen, and/or stylus through which a user of computing device 4701 may provide input, and may also include one or more of a speaker for providing audio output and a video display device for providing textual, audiovisual and/or graphical output. Computing system environment 4700 may also include optical scanners (not shown). Illustrative usages include scanning and converting paper documents, e.g., correspondence, receipts, and the like, to digital files.

Computing device 4701 may operate in a networked environment supporting connections to one or more remote computing devices, such as computing devices 4741, 4751, and 4761. Computing devices 4741, 4751, and 4761 may be personal computing devices or servers that include any or all of the elements described above relative to computing device 4701. Computing device 4761 may be a mobile device (e.g., smart phone) communicating over wireless carrier channel 4771.

The network connections depicted in FIG. 47 may include local area network (LAN) 4725 and wide area network (WAN) 4729, as well as other networks. When used in a LAN networking environment, computing device 4701 may be connected to LAN 4725 through a network interface or adapter in communications module 4709. When used in a WAN networking environment, computing device 4701 may include a modem in communications module 4709 or other means for establishing communications over WAN 4729, such as Internet 4731 or other type of computer network. The network connections shown are illustrative and other means of establishing a communications link between the computing devices may be used. Various well-known protocols such as transmission control protocol/Internet protocol (TCP/IP), Ethernet, file transfer protocol (FTP), hypertext transfer protocol (HTTP) and the like may be used, and the system can be operated in a client-server configuration to permit a user to retrieve web pages from a web-based server. Any of various conventional web browsers can be used to display and manipulate data on web pages.

The disclosure is operational with numerous other general purpose or special purpose computing system environments or configurations. Examples of well-known computing systems, environments, and/or configurations that may be suitable for use with the disclosed embodiments include, but are not limited to, personal computers (PCs), server computers, hand-held or laptop devices, smart phones, multiprocessor systems, microprocessor-based systems, set top boxes, programmable consumer electronics, network PCs, minicomputers, mainframe computers, distributed computing environments that include any of the above systems or devices, and the like.

While aspects of the present disclosure have been described in terms of preferred examples, and it will be understood that the disclosure is not limited thereto since modifications may be made to those skilled in the art, particularly in light of the foregoing teachings.

The invention claimed is:

1. A method comprising:
advancing a device capable of detecting anatomical structures and comprising a proximal end, a distal end, an elongated body extending between the proximal end and the distal end, and at least one ultrasound transducer positioned at the distal end into a patient such that the distal end is positioned on a surface of a patient's muscle without penetrating the patient's muscle, wherein the patient's muscle is located between the device and a surgical site;
scanning the patient's muscle to generate a b-mode image of the patient's muscle, wherein the scanning is performed with the device positioned on the patient's muscle and without penetrating the patient's muscle;
identifying image texture and echogenicity information from a digital representation of anatomical structures in the b-mode image;
identifying at least one voltage trace associated with an anatomical tissue from at least one scan line from the digital representation of anatomical structures in the b-mode image;
comparing the at least one voltage trace to a predetermined voltage trace of a target anatomy;

determining a presence or an absence of a spectral signature of the target anatomy in the at least one voltage trace based on the comparison;

determining, based on the presence of the spectral signature, the anatomical tissue to be the target anatomy;

determining, without penetrating the patient's muscle, a trajectory between the distal end and the surgical site, wherein the trajectory passes through the patient's muscle and avoids the target anatomy; and outputting an indication of the trajectory.

2. The method of claim 1, wherein the scanning comprises scanning the patient's muscle to a depth of between 1 mm and 40 mm.

3. The method of claim 1, wherein the determining the trajectory comprises determining a path free of nerves and vasculature.

4. The method of claim 1, wherein the comparing the at least one voltage trace to the predetermined voltage trace of the target anatomy comprises comparing the at least one voltage trace to a predetermined voltage trace of a nerve or to a predetermined voltage trace of vasculature.

5. The method of claim 4, further comprising determining a location of the nerve or determining a location of the vasculature.

6. The method of claim 1, wherein the patient's muscle comprises a psoas muscle and wherein the surgical site comprises a patient's spine.

7. The method of claim 1, wherein the trajectory between the distal end and the surgical site is a linear trajectory.

8. The method of claim 1, wherein the trajectory between the distal end and the surgical site is a nonlinear trajectory.

9. The method of claim 1, wherein the outputting the indication comprises outputting the indication for display.

10. The method of claim 1, wherein the scanning comprises a first scanning of the patient's muscle at a first position, the method further comprising scanning the patient's muscle at a second position and wherein the determining the trajectory is based at least in part on the first scanning of the patient's muscle at the first position and the scanning the patient's muscle at the second position.

11. A method comprising:

advancing a device capable of detecting anatomical structures and comprising a proximal end, a distal end, an elongated body extending between the proximal end and the distal end, and at least one ultrasound transducer positioned at the distal end into a patient such that the distal end is positioned on a surface of a patient's anatomy without penetrating the patient's anatomy, wherein the patient's anatomy is located between the device and a surgical site;

scanning the patient's anatomy to generate a b-mode image of the patient's anatomy, wherein the scanning is performed with the device positioned on the patient's anatomy and without penetrating the patient's anatomy;

identifying image texture and echogenicity information from a digital representation of anatomical structures in the b-mode image;

identifying at least one voltage trace associated with an anatomical tissue from at least one scan line from the digital representation of anatomical structures in the b-mode image;

comparing the at least one voltage trace to a predetermined voltage trace of a muscle;

determining a presence or an absence of a spectral signature of the muscle in the at least one voltage trace based on the comparison;

determining, based on the presence of the spectral signature, the anatomical tissue to be the muscle;

based on a determination that a path between the distal end of the device and the surgical site does not pass through anatomy other than muscle, determining, without penetrating the patient's anatomy, that the path comprises a trajectory between the distal end and the surgical site; and outputting an indication of the trajectory.

12. The method of claim 11, wherein the patient's anatomy comprises a psoas muscle and wherein the surgical site comprises a patient's spine.

13. The method of claim 11, wherein the outputting the indication comprises outputting the indication for display.

14. A method comprising:

advancing a device capable of detecting anatomical structures and comprising a proximal end, a distal end, an elongated body extending between the proximal end and the distal end, and at least one ultrasound transducer positioned at the distal end into a patient such that the distal end is positioned on a surface of a patient's anatomy without penetrating the patient's anatomy, wherein the patient's anatomy is located between the device and a surgical site;

scanning the patient's anatomy to generate a b-mode image of the patient's anatomy, wherein the scanning is performed with the device positioned on the patient's anatomy and without penetrating the patient's anatomy;

identifying image texture and echogenicity information from a digital representation of anatomical structures in the b-mode image;

identifying at least one voltage trace associated with an anatomical tissue from at least one scan line from the digital representation of anatomical structures in the b-mode image;

comparing the at least one voltage trace to a predetermined voltage trace of a target anatomy;

determining a presence or an absence of a spectral signature of the target anatomy in the at least one voltage trace based on the comparison;

determining, based on the presence of the spectral signature, the anatomical tissue to be the target anatomy;

determining, without penetrating the patient's anatomy, a trajectory between the distal end and the surgical site, wherein the trajectory avoids the target anatomy; and outputting an indication of the trajectory.

15. The method of claim 14, wherein the predetermined voltage trace of the target anatomy comprises a predetermined voltage trace of a nerve, a predetermined voltage trace of a vasculature or a predetermined voltage trace of a psoas muscle.

16. The method of claim 14, wherein the outputting the indication comprises outputting the indication for display.

* * * * *